(12) United States Patent
Zhang et al.

(10) Patent No.: US 7,569,564 B2
(45) Date of Patent: Aug. 4, 2009

(54) CYCLOTHIOCARBAMATE DERIVATIVES AS PROGESTERONE RECEPTOR MODULATORS

(75) Inventors: Puwen Zhang, Audubon, PA (US); Andrew Fensome, Wayne, PA (US); Eugene A. Terefenko, Quakertown, PA (US); Lin Zhi, San Diego, CA (US); Todd K. Jones, Solana Beach, CA (US); James P. Edwards, San Diego, CA (US); Christopher M. Tegley, Thousand Oaks, CA (US); Jay E. Wrobel, Lawrenceville, NJ (US); Mark A. Collins, Norristown, PA (US)

(73) Assignee: Wyeth, Madison, NJ (US)

( * ) Notice: Subject to any disclaimer, the term of this patent is extended or adjusted under 35 U.S.C. 154(b) by 438 days.

(21) Appl. No.: 11/351,002

(22) Filed: Feb. 9, 2006

(65) Prior Publication Data

US 2006/0142280 A1 Jun. 29, 2006

Related U.S. Application Data

(63) Continuation of application No. 10/140,034, filed on May 6, 2002, now Pat. No. 7,081,457, which is a continuation of application No. 09/552,354, filed on Apr. 19, 2000, now Pat. No. 6,436,929.

(60) Provisional application No. 60/183,013, filed on May 4, 1999.

(51) Int. Cl.
*A61K 31/536* (2006.01)
*C07D 265/12* (2006.01)

(52) U.S. Cl. .......... 514/230.5; 544/90; 544/92

(58) Field of Classification Search .......... 514/230.5; 544/90, 92
See application file for complete search history.

(56) References Cited

U.S. PATENT DOCUMENTS

| | | | |
|---|---|---|---|
| 3,526,621 A | 9/1970 | Bernardi | |
| 3,635,941 A | 1/1972 | Weaver | |
| 3,635,964 A | 1/1972 | Skorcz | |
| 3,917,592 A | 11/1975 | Kobzina | |
| 4,093,730 A | 6/1978 | Butti | |
| 4,440,785 A | 4/1984 | Walsh | |
| 4,518,597 A | 5/1985 | Narr et al. | |
| 4,666,913 A | 5/1987 | Kuhla | |
| 4,670,566 A | 6/1987 | Walsh | |
| 4,721,721 A | 1/1988 | Kuhla | |
| 4,792,561 A | 12/1988 | Walker | |
| 4,822,794 A | 4/1989 | Spada | |
| 4,831,027 A | 5/1989 | Narr | |
| 4,853,473 A | 8/1989 | Fischer | |
| 5,007,952 A | 4/1991 | Kume | |
| 5,171,851 A | 12/1992 | Kim | |
| 5,414,088 A | 5/1995 | Von Der Saal | |
| 5,447,928 A | 9/1995 | Williams | |
| 5,453,516 A | 9/1995 | Fischer | |
| 5,475,020 A | 12/1995 | Johnson | |
| 5,519,021 A | 5/1996 | Young | |
| 5,521,166 A | 5/1996 | Grubb | |
| 5,659,046 A | 8/1997 | Kameswaran | |
| 5,681,817 A | 10/1997 | Hodgen | |
| 5,688,808 A | 11/1997 | Jones | |
| 5,688,810 A | 11/1997 | Jones | |
| 5,693,646 A | 12/1997 | Jones | |
| 5,693,647 A | 12/1997 | Jones | |
| 5,696,127 A | 12/1997 | Jones | |
| 5,696,130 A | 12/1997 | Jones | |
| 5,696,133 A | 12/1997 | Jones | |
| 5,719,136 A | 2/1998 | Chwalisz | |
| 5,733,902 A | 3/1998 | Schneider | |
| 5,808,139 A | 9/1998 | Pathirana | |
| 5,874,430 A | 2/1999 | Christ | |
| 6,077,840 A | 6/2000 | Kurihara | |
| 6,306,851 B1 | 10/2001 | Santilli | |
| 6,319,912 B1 | 11/2001 | Grubb | |
| 6,329,416 B1 | 12/2001 | Grubb | |
| 6,339,098 B1 | 1/2002 | Collins | |
| 6,355,648 B1 | 3/2002 | Fensome | |
| 6,358,947 B1 | 3/2002 | Zhi | |

(Continued)

FOREIGN PATENT DOCUMENTS

DE 3633861 4/1988

(Continued)

OTHER PUBLICATIONS

Collins et al., "Novel Pyrrole-Containing Progesterone Receptor Modulators", Bioorg. Med. Chem. Lett., 14:2185 (2004), pp. 2185-2189.

(Continued)

*Primary Examiner*—James O Wilson
*Assistant Examiner*—Tamthom N Truong
(74) *Attorney, Agent, or Firm*—Paul Carango, Esq.; Howson & Howson LLP

(57) ABSTRACT

Methods of using compounds which are progesterone receptor agonists for contraception and the treatment of progesterone-related maladies alone or in combination with an estrogen receptor agonist or progesterone receptor antagonist are provided. These compounds have the structure:

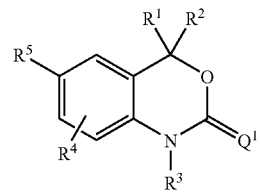

wherein $R^1$, $R^2$, $R^3$, $R^4$, $R^5$, and $Q^1$ are defined herein.

9 Claims, No Drawings

U.S. PATENT DOCUMENTS

| | | |
|---|---|---|
| 6,358,948 B1 | 3/2002 | Zhang |
| 6,369,056 B1 | 4/2002 | Zhang |
| 6,380,178 B1 | 4/2002 | Grubb |
| 6,380,235 B1 | 4/2002 | Zhang |
| 6,391,907 B1 | 5/2002 | Fensome |
| 6,399,593 B1 | 6/2002 | Grubb |
| 6,407,101 B1* | 6/2002 | Collins et al. ............ 514/230.5 |
| 6,417,214 B1 | 7/2002 | Ullrich |
| 6,423,699 B1 | 7/2002 | Grubb |
| 6,436,929 B1 | 8/2002 | Zhang |
| 6,441,019 B2 | 8/2002 | Zhang |
| 6,444,668 B1 | 9/2002 | Grubb |
| 6,462,032 B1 | 10/2002 | Grubb |
| 6,498,154 B1 | 12/2002 | Grubb |
| 6,503,939 B2 | 1/2003 | Grubb |
| 6,509,334 B1* | 1/2003 | Zhang et al. ............ 514/230.5 |
| 6,521,657 B2 | 2/2003 | Fensome |
| 6,544,970 B2 | 4/2003 | Grubb |
| 6,562,857 B2 | 5/2003 | Collins |
| 6,566,358 B2 | 5/2003 | Zhang |
| 6,566,372 B1 | 5/2003 | Zhi |
| 6,608,068 B2 | 8/2003 | Fensome |
| 6,693,103 B2 | 2/2004 | Zhang |
| 6,713,478 B2* | 3/2004 | Zhang et al. ............ 514/230.5 |
| 6,759,408 B2 | 7/2004 | Grubb |
| 6,794,373 B2 | 9/2004 | Grubb |
| 6,835,744 B2 | 12/2004 | Ullrich |
| 6,841,568 B2 | 1/2005 | Fensome |
| 6,946,454 B2 | 9/2005 | Fensome |
| 6,964,973 B2 | 11/2005 | Zhi |
| 6,982,261 B2 | 1/2006 | Collins |
| 2002/0111355 A1 | 8/2002 | Zhang |
| 2002/0115853 A1 | 8/2002 | Zhang |
| 2003/0092711 A1 | 5/2003 | Zhang |
| 2003/0220388 A1 | 11/2003 | Ullrich |
| 2004/0002535 A1 | 1/2004 | Fensome |
| 2004/0006060 A1 | 1/2004 | Fensome |
| 2004/0006122 A1 | 1/2004 | Fensome |
| 2004/0014798 A1 | 1/2004 | Fensome |
| 2004/0186101 A1 | 9/2004 | Zhang |
| 2005/0054711 A1 | 3/2005 | Fensome |
| 2005/0171186 A1 | 8/2005 | Fensome |
| 2005/0256110 A1 | 11/2005 | Collins |

FOREIGN PATENT DOCUMENTS

| | | |
|---|---|---|
| DE | 4330234 | 3/1995 |
| DE | 4344463 | 6/1995 |
| EP | 022317 | 1/1981 |
| EP | 208510 | 1/1987 |
| EP | 311135 | 4/1989 |
| EP | 0166533 | 4/1990 |
| EP | 385850 | 9/1990 |
| EP | 483077 | 9/1991 |
| EP | 454330 | 10/1991 |
| EP | 535529 | 9/1992 |
| EP | 510235 | 10/1992 |
| EP | 947507 | 10/1999 |
| EP | 978279 | 2/2000 |
| JP | 63112584 | 5/1988 |
| RU | 95107403 A1 | 11/1996 |
| RU | 2130020 C1 | 5/1999 |
| RU | 2134262 C1 | 8/1999 |
| WO | WO-86/03749 | 7/1986 |
| WO | WO-91/04974 | 4/1991 |
| WO | WO-91/06545 | 5/1991 |
| WO | WO-93/12085 | 6/1993 |
| WO | WO-94/14434 | 7/1994 |
| WO | WO-94/29272 | 12/1994 |
| WO | WO-95/11013 | 4/1995 |
| WO | WO-95/20389 | 8/1995 |
| WO | WO-95/20972 | 8/1995 |
| WO | WO-95/33746 | 12/1995 |
| WO | WO-96/15794 | 5/1996 |
| WO | WO-96/19458 | 6/1996 |
| WO | WO-96/19997 | 7/1996 |
| WO | WO-97/13767 | 4/1997 |
| WO | WO-97/49407 | 12/1997 |
| WO | WO-98/14436 | 4/1998 |
| WO | WO-98/27059 | 6/1998 |
| WO | WO-98/55116 | 12/1998 |
| WO | WO-99/10325 | 3/1999 |
| WO | WO-99/11264 | 3/1999 |
| WO | WO-99/15500 | 4/1999 |
| WO | WO-99/44608 | 9/1999 |
| WO | WO-01/15108 A2 | 3/2001 |

OTHER PUBLICATIONS

Zhang et al., "6-Aryl-1,4-dihydro-benzo[d][1,3]oxazin-2-ones: A Novel Class of Potent, Selective, and Orally Active Nonsteroidal Progesterone Receptor Antagonists", J. Med. Chem., 45(20):4379 (Aug. 27, 2002), pp. 4379-4382.

R. Evans, "The Steroid and Thyroid Hormone Receptor Superfamily", Science, 240:889 (May 13, 1988).

A. Ulmann et al, "Clinical Uses of Mifepristone (MFP)", Ann. N.Y. Acad. Sci., 261:248 (Jun. 12, 1995).

R. Kekkonen et al, "Sequential Regiment of the Antiprogesterone RU486 and Synthetic Progestin for Contraception", Fertility and Sterility, 60(4):610 (Oct. 1993).

K. Horwitz et al, "Progestin, Progesterone Receptors, and Breast Cancer", Horm. Cancer, publisher: Birkhaeuser, Boston, Mass., ed. Vedeckis, pp. 283-306 (1996) (abstract only).

A. Murphy et al, "Regression of Uterine Leiomyomata in Response to the Antiprogesterone RU486", J. Clin. Endo. Metab., 76(2):513 (Feb. 1993).

L. Kettel et al, "Endocrine Responses to Long-Term Administration of the Antiprogesterone RU486 in Patients with Pelvic Endometriosis", Fertility and Sterility, 56(3):402 (Sep. 1991).

H. Michna et al, "Differentiation Therapy with Progesterone Antagonists", Ann. N.Y. Acad. Sci., 761:224 (Jun. 1995).

L. Zhi et al, "5-Aryl-1,2-Dihydrochromeno[3,4-f]quinolines: A Novel Class of Nonsteroidal Human Progesterone Receptor Agonists", J. Med. Chem., 41(3):291 (Oct. 22, 1998).

D. Combs et al, "Nonsteroidal Progesterone Receptor Ligands. 2. High-Affinity Ligands with Selectivity for Bone Cell Progesterone Receptors", J. Med. Chem., 38:4880 (Dec. 8, 1995).

K. Perlman et al, "20-Oxopregnacalciferols: Vitamin D Compounds that Bind the Progesterone Receptor", Tet. Letters, 35(15):2295 (1994).

L. Hamann et al, "Synthesis and Biological Activity of Novel Nonsteroidal Progesterone Receptor Antagonists", Ann. N.Y. Acad. Sci., 761:383 (Jun. 12, 1995).

R. Chen et al, "Synthesis and SAR of a Novel Series of Spirobenzothlzaepine Derivatives with Antiprogestin Activity", POI-37, 16th Int. Cong. Het. Chem., Montana (1997).

B. Narr et al, "Preparation, Testing, and Formulation of Imidazobenzoxazinones as Cardiotonics", Chemical Abstracts, 109:22973 (1988).

R. Hartmann et al, "Effects of Brofoxine, A New Anxiolytic on Experimentally Induced Conflict in Rats", Proc. West. Pharmacol. Soc., 21:51-55 (1978).

B. Singh et al, "Novel cAMP PDE III Inhibitor" Imidazo[4,5-b]pyridin-2(3H)-ones and Thiazolo[4,5-b]pyridin-2(3H)-ones and their Analogs, J. Med. Chem., 37:248 (Jan. 21, 1994).

A. Andreani et al, "Potential Antitumor Agents XVII (1). Cytotoxic Agents from Indole Derivatives and their Intermediates", Acta. Pharm. Nord., 2(6):407 (1990).

Sakata et al, "Silver Halide Photographic Materials Useful for Platemaking", Chemical Abstracts, 123:301431 (1993).

P. Pflegel et al, "Polarografie con 7-Chlor-5-phenyl-2-thioxo-1H-2,3-dihydro-1,3,4-benzotriazepinen", Pharmazie, 37(10):714-717 (1982).

E. Barengolts et al, "Progesterone Antagonist RU486 has Bone-Sparing Effects in Ovariectomized Rats", Bone, 17(1):21 (Jul. 1995).

E. Gromachevskaya et al, "Studies of 4H-3, 1-Benzoxazines", Chem. Heterocycl. Cmpds., 33(10):1209-1214 (1997).

D. Chiarino et al, "2,1-Benzisothiazoline 2,2-Dioxide and Derivatives", J. Heterocycl. Chem., 23(6):1645-1649 (Nov.-Dec. 1986).

A. Turck et al, "On the Metabolism of 3-Substituted and 3,6-Disubstituted Pyridazines", Tetrahedron, 49(3):599-606 (1993).

V. Kumar et al, "Synthesis of 7-Azaindole and 7-Azaoxindole Derivatives through a Palladium-Catalyzed Cross-Coupling Reaction", J. Org. Chem., 57(25):6995-6998 (1992).

P. Canonne et al, "Spirocyclization of 1-(o-Aminophenyl)cycloalkanols and 1-(2'-Amino-3'-pyridinyl)cycloalkanols", J Heterocyclic Chem., 26:113 (Jan.-Feb. 1989).

M-C. Forest et al, "A Novel Class of Cardiotonic Agents: Synthesis and Biological Evaluation of 5-Substituted 3,6-Dihydrothiadiazin-2-ones with Cyclic AMP Phosphodiesterase Inhibiting and Myofibrillar Calcium Sensitizing Properties", J. Med. Chem., 35:163-172 (Jan. 1992).

D. Combs et al, "Heteroatom Analogues of Bemoradan: Chemistry and Cardiotonic Activity of 1,4-Benzothiazinylpyridazinones", J. Med. Chem., 35:172-176 (Jan. 1992).

Kurihari et al., "Synthesis of (±)-PF1092A, B, and C; New Nonsteroidal Progesterone Receptor Ligands", J. Antibiotics, 50(4):360 (Apr. 1997).

A. Kende et al., "Regioselective C-3 Alkylation of Oxindole Dianion", Synth. Commun. 12(1):1 (1982).

T. Tucker et al., "Synthesis of a Series of 4-(Arylethylnyl)-6-Chloro-4-Cyclopropyl-3,4-dihydroquinazolin-2(1H)-ones as Novel Non-Nucleoside HIV-1 Reverse Transcriptase Inhibitors", J. Med. Chem., 37:2347-2444 (Jul. 22, 1994).

J. Edwards et al., "5-Aryl-1,2-Dihydro-5H-Chromeno[3,4-f]Quinolines as Potent, Orally Active, Nonsteroidal Progesterone Receptor Agonists: The Effect of D-Ring Substituents", J. Med. Chem., 41:303-310 (Jan. 29, 1998).

Nakao, "New Imidazo-Pyridine Derivatives—Useful as Platelet Agglutination Inhibitor, Antiallergic, Antiinflammatory Sedative, Cardiac, and Cardiovascular Vasodilators", Derwent WPI abstract of JP 63112584 (May 17, 1988).

N. Bru-Magniez, "Benzimidazole and Azabenzimidazole(s)-Having Cardiotonic, Vasodilating, Anti-Hypertensive, Anti-Aggregation, and Anti-Ulcer Activity", Derwent WPI Abstract of EP 385,850 (Sep. 5, 1990).

F. Arndt, "New Heterocycle substituted Benzo-Fused Azine and Azole Derivatives-Useful as Selective Herbicides for Pre or Post-Emergence Application", Derwent WPI Abstract of EP 311,135 (Apr. 12, 1989).

K. Horwitz et al., "Progestin, Progesterone Receptors, and Breast Cancer", "Hormones and Cancer", publisher: Birkhaeuser, Boston, Mass., ed. Vedeckis, p. 283-306 (1996).

V. Mamaev et al., "Synthesis of 4H-Thieno [3,2-B] Pyrrol-5(6H)-One" Bulletin of the Academy of Sciences of the USSR. Division of Chemical Science, US, Consultants Bureau. New York. vol. 9, p. 1549-1553, (1966).

K. Chwalisz et al. "Female Contraceptive Method Comprises Gestation Treatment with Intermittent Progesterone Antagonist Administration.", Derwent WPI Abstract of DE 4,330,234 (Mar. 9, 1995).

K. Chwalisz et al. "Contraceptive Pack for Implantation Inhibition—Contains Competitive Progesterone Antagonist and Gestagen for Sequential Oral Administration.", Derwent WPI Abstract of DE 4,344,463 (Jun. 29, 1995).

K. Kolasa et al., "Preliminary Pharmacological Studies of the Central Action of Phenyl and Piperidinomethyl Derivatives of 2-Benzoxazolone", Chemical Abstracts, vol. 99, No. 1, Abst. No. 157a (Jul. 4, 1983).

N. Meanwell et al., "Regiospecific Functionalization of 1,3-dihydro-2H-Benzimidazol-2-One and Structurally Related Cyclic Urea Derivatives", J. Organic Chem., 60(6):1565-82 (Mar. 24, 1995).

B. Singh et al., "An Efficient and Novel Synthesis of Fused Thiazol-2(3H)-ones" Heterocycles, 36(1):133-134, p. 136, compounds 16a, 18a (Jan. 1993).

G. Vernin et al., "Etude Dans la Serie des Radicaux Heterocycliques. Partie XV. Decomposition aprotique de 1' amino-6-ethyl-2-benzothiazole dans des substrats aromatiques et heteroaromatiques: preparation des mesityl-6-et furyl-6-ethyl-2-benzothiazoles, des sels quaternaires et des spiropyrannes correspondants", Helvetica Chimica Acta, 62(1/3):21-30 (Jan. 24, 1979).

Wolters Kluwer Co., "Drug Facts and Comparison", 1995 Ed., St. Louis, MO, pp. 388, 395, and 396.

Fensome et al., "Synthesis and Structure-Activity Relationship of Novel 6-Aryl-1,4-dihydrobenzo[d][1,3]oxazine-2-thiones as Progesterone Receptor Modulators Leading to the Potent and Selective Nonsteroidal Progesterone Receptor Agonist Tanaproget", J. Med. Chem., 48: 5092-5095 (Aug. 11, 2005).

Zhang et al., "Novel 6-Aryl-1,3-dihydrobenzo[d][1,3]oxazine-2-thiones as Potent, Selective, and Orally Active Nonsteroidal Progesterone Receptor Agonists", Bioorg. Med. Chem. Lett., 13:1313-1316 (Apr. 7, 2003).

Winneker et al., "Nonsteroidal Progesterone Receptor Modulators: Structure Activity Relationships", Sem. Reprod. Med., 23(1): 46 (Feb. 2005).

Zhang et al., "Potent Nonsteroidal Progesterone Receptor Agonists: Synthesis and SAR study of 6-Aryl Benzoxazines", Bioorg. Med. Chem. Lett., 12: 787-790 (Mar. 11, 2002).

English translation of the Search Report issued in counterpart Hungarian Patent Application No. P0200993 (Apr. 8, 2003).

English translation of a Search Report issued in counterpart Georgian Patent Application No. AP 22000 004535 (Jul. 26, 2001).

English translation of a Search Report issued in counterpart Georgian Patent Application No. AP 2000 004535 (Jan. 22, 2003).

English translation of a First Office Action issued in counterpart Chinese Patent Application No. 00807099.7 (Jan. 31, 2003).

Examination Report issued in counterpart European Patent Application No. 00930266.2 (Jan. 7, 2005).

English translation of a Notification issued in counterpart Eurasian Patent Application No. 200101181 (Jan. 20, 2003).

English translation of a Notification issued in counterpart Vietnamese Patent Application No. 1-2001-01170 (Dec. 5, 2003).

Official Action and English translation thereof prepared by foreign associate issued in counterpart Norwegian Patent Application No. 20015381 (Feb. 8, 2005).

English translation prepared by foreign associate of a first Substantive Report issued in counterpart Chilean Patent Application No. 1103-2000.

English translation prepared by foreign associate of a second Decision issued in counterpart Taiwanese Patent Application No. 89108475 (Feb. 15, 2006).

Kameswaran, "Method Preparing 2-Perfluoroalkyl-3-oxazolin-5-one, and Intermediate Products", English abstract of RU-2134262-C1 (Aug. 10, 1999).

Jang, "Benzoxazinone Compounds, Pharmaceutical Compositions, Methods of Inhibition of Reverse Transcriptase, Prophylaxis and Treatment, Synergistic Combination and Method of Synthesis of (-)-6-Chloro-4-Cyclopropylethynyl-4-trifluoromethyl-1,4-dihydro-2H-3,1-Benzoxazine-2-one", English abstract of RU-95107403-A1 (Nov. 20, 1996).

Williams, "Derivatives of Benzoxazine, Methods of Their Synthesis, A Pharmaceutical Preparation", English abstract of RU-2130020-C1 (May 10, 1999).

* cited by examiner

CYCLOTHIOCARBAMATE DERIVATIVES AS PROGESTERONE RECEPTOR MODULATORS

CROSS-REFERENCE TO RELATED APPLICATIONS

This application is a continuation of U.S. patent application Ser. No. 10/140,034, filed May 6, 2002, now U.S. Pat. No. 7,081,457, issued Jul. 25, 2006, which is a continuation of U.S. patent application Ser. No. 09/552,354, filed Apr. 19, 2000, now U.S. Pat. No. 6,436,929, issued Aug. 20, 2002, which claims the benefit of the priority of U.S. Provisional Patent Application No. 60/183,013, filed May 4, 1999, now abandoned.

BACKGROUND OF THE INVENTION

This invention relates to compounds which are agonists of the progesterone receptor, their preparation and utility. This invention also provides methods of using these compounds in the inducement of contraception and the treatment and/or prevention of dysfunctional bleeding, uterine leiomyomata, endometriosis, polycystic ovary syndrome, and carcinomas and adenocarcinomas of the endometrium, ovary, breast, colon, and prostate.

Intracellular receptors (IR) form a class of structurally related gene regulators known as "ligand dependent transcription factors" (R. M. Evans, *Science*, 240, 889, 1988). The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and protein encoded by that gene.

A compound that binds to an IR and mimics the action of the natural hormone is termed an agonist, whilst a compound which inhibits the effect of the hormone is an antagonist.

PR agonists (natural and synthetic) are known to play an important role in the health of women. PR agonists are used in birth control formulations, typically in the presence of an ER agonist, alternatively they may be used in conjunction with a PR antagonist. ER agonists are used to treat the symptoms of menopause, but have been associated with a proliferative effect on the uterus which can lead to an increased risk of uterine cancers. Co-administration of a PR agonist reduces/ablates that risk.

Jones, et al describe in U.S. Pat. No. 5,688,810 the PR antagonist dihydroquinoline 1.

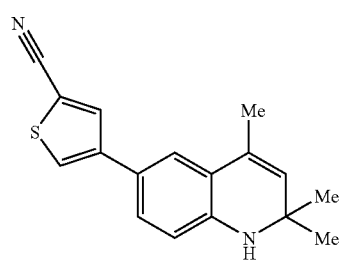

1

Jones, et al, described the enol ether 2 (U.S. Pat. No. 5,693,646) as a PR ligand.

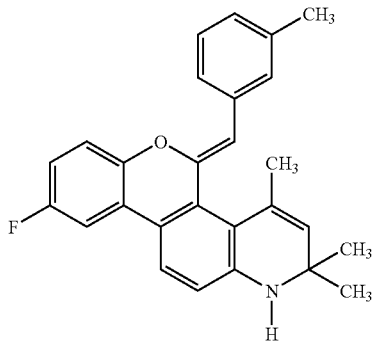

2

Jones, et al, described compound 3 (U.S. Pat. No. 5,696,127) as a PR ligand.

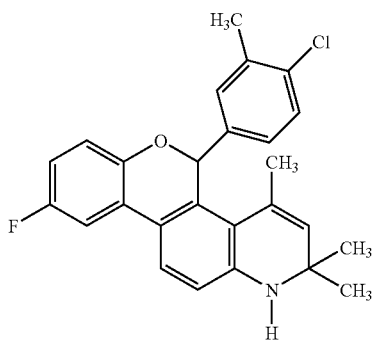

3

Zhi, et al, described lactones 4, 5 and 6 as PR antagonists (J. Med. Chem., 41, 291, 1998).

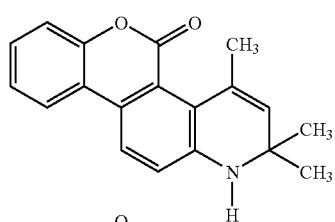

4

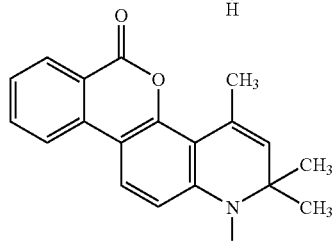

5

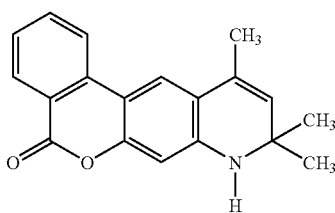

6

Zhi, et al, described the ether 7 as a PR antagonist (J. Med. Chem., 41, 291, 1998).

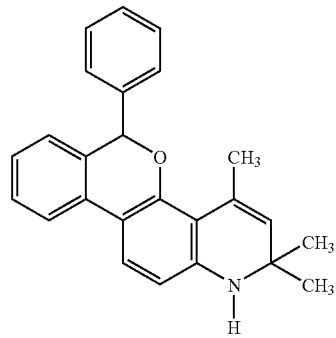

7

Combs, et al., disclosed the amide 8 as a ligand for the PR (J. Med. Chem., 38, 4880, 1995).

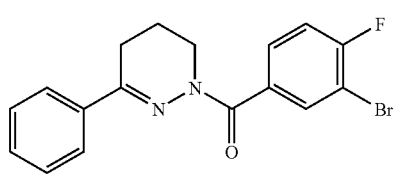

8

Perlman, et. al., described the vitamin D analog 9 as a PR ligand (Tet. Letters, 35, 2295, 1994).

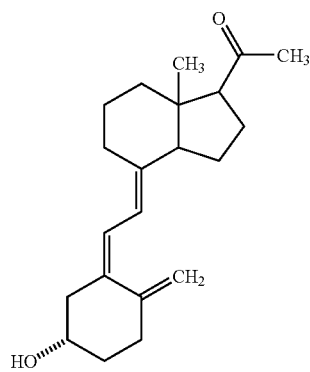

9

Hamann, et al, described the PR antagonist 10 (Ann. N.Y. Acad. Sci., 761, 383, 1995).

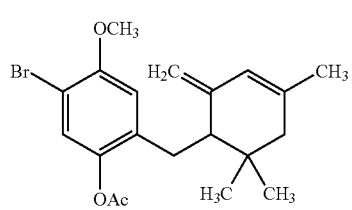

10

Chen, et al, described the PR antagonist 11 (Chen, et al, POI-37, 16$^{th}$ Int. Cong. Het. Chem., Montana, 1997).

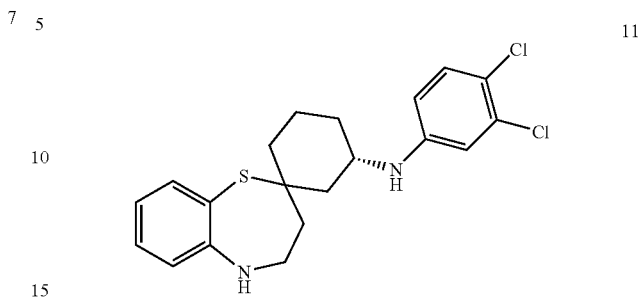

11

Kurihari, et. al., described the PR ligand 12 (J. Antibiotics, 50, 360, 1997).

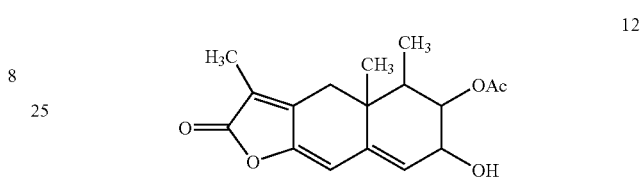

12

Sakata et al. (JP 07159917, CA 123:301431) teach that certain benzoxazin-2-thione compounds such as compound A can be used as photographic materials. Kim et al. disclose that some imidazole substituted benzothiazines, such as compound B, can be used as cardiotonics (U.S. Pat. No. 5,171,851 and EP 510,235). More recently, Young et al. (WO95/20389) and Christ et al. (WO98/14436) claimed benzoxazin-2-thiones such as compound C as inhibitors of HIV reverse transcriptase.

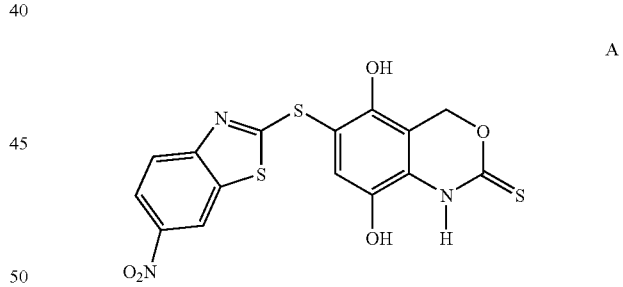

A

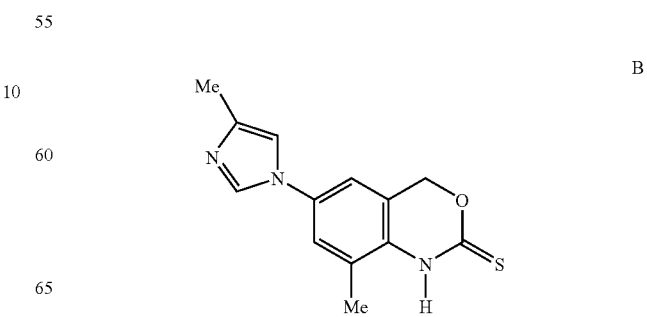

B

-continued

C

Pflegel et al. (Pharmazie, 37(10), 714-717 (1982)) disclosed quinazolin-2-thiones such as compound D in their study of polarography of heterocyclics, but disclosed no activity for compound D.

D

DETAILED DESCRIPTION OF THE INVENTION

This invention provides compounds of the formula:

wherein:

$R_1$ and $R_2$ are independent substituents selected from the group of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;

or $R^1$ and $R^2$ are fused to form a spirocyclic ring selected from a), b) or c), below, each spirocyclic ring being optionally substituted by from 1 to 3 substituents selected from H or $C_1$-$C_3$ alkyl:

a) a 3 to 8 membered spirocyclic alkyl ring, preferably a 3 to 6 membered spirocyclic alkyl ring; or b) a 3 to 8 membered spirocyclic alkenyl ring, preferably a 3 to 6 membered spirocyclic alkenyl ring; or c) a 3 to 8 membered spirocyclic ring containing one to three heteroatoms selected from O, S and N, preferably a 3 to 6 membered spirocyclic ring containing one to three heteroatoms;

$R^A$ is selected from H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, amino, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R^3$ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, substituted alkynyl, or $COR^C$;

$R^C$ is selected from H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^4$ is selected from H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;

$R^5$ is selected from groups a), b), or c) below:

a) $R^5$ is a trisubstituted benzene ring containing the substituents X, Y and Z as shown below:

X is selected from the group including halogen CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring containing 1 to 3 heteroatoms, $COR^D$, $OCOR^D$, or $NR^E COR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independent substituents selected from the group of H, halogen, CN, $NO_2$, $C_1$ to $C_3$ alkoxy, $C_1$ to $C_3$ alkyl, or $C_1$ to $C_3$ thioalkoxy; or b) $R^5$ is a five or six membered heterocyclic ring with 1, 2, or 3 ring heteroatoms selected from the group of O, S, S(O), $S(O_2)$ or $NR^6$ and containing one or two independent substituents from the group of H, halogen, CN, $NO_2$ and $C_1$ to $C_3$ alkyl, $C_1$ to $C_3$ alkoxy, $C_1$ to $C_3$ aminoalkyl, $COR^F$, or $NR^G$-$COR^F$;

$R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^G$ is H, $C_1$ to $C_3$ alkyl, or substituted $C_1$ to $C_3$ alkyl;

$R^6$ is H, or $C_1$ to $C_3$ alkyl; or c) $R^5$ is a six membered ring with the structure:

wherein:

$X^1$ is N or $CX^2$, $X^2$ is halogen, CN, or $NO_2$, $Q^1$ is S, $NR^7$, or $CR^8R^9$;

$R_7$ is selected from the group of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, or substituted heterocyclic, $SO_2CF_3$, OR or $NR^{11}R^{12}$;

$R^8$ and $R^9$ are independent substituents selected from the group of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN, or $CO_2R^{10}$;

$R^{10}$ is $C_1$ to $C_3$ alkyl;

or $CR^8R^9$ comprise a six membered ring as shown by the structure below:

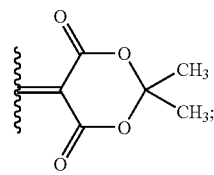

$Q^2$ is selected from the moieties:

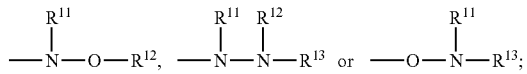

$R^{11}$, $R^{12}$ and $R^{13}$ are independently selected from H, $C_1$ to $C_6$ alkyl, substituted $C_1$ to $C_6$ alkyl, aryl, substituted aryl, heteroaryl, substituted heteroaryl, acyl or sulfonyl; or a pharmaceutically acceptable salt thereof.

A preferred list of substituents represented by $R^{11}$, $R^{12}$ and $R^{13}$ in groups of the compounds described herein are H, $C_1$ to $C_6$ alkyl, substituted $C_1$ to $C_6$ alkyl, —C(O)—($C_1$ to $C_6$ alkyl), —S(O)$_2$—($C_1$ to $C_6$ alkyl), phenyl or benzyl.

Among the preferred compounds of this invention are those of the formula:

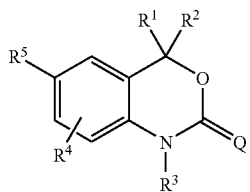

wherein:

$R^1$ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^B\text{-}COR^A$;

$R^2$ is H, $C_1$ to $C_6$ alkyl, substituted $C_1$ to $C_6$ alkyl, $C_2$ to $C_6$ alkenyl, substituted $C_2$ to $C_6$ alkenyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$;

or $R^1$ and $R^2$ are fused to form:

a) a 3 to 8 membered spirocyclic alkyl ring optionally substituted by from 1 to 3 substituents selected from H or $C_1$ to $C_3$ alkyl; or b) a 3 to 8 membered spirocyclic alkenyl ring optionally substituted by from 1 to 3 substituents selected from H or $C_1$ to $C_3$ alkyl; or c) a 3 to 8 membered spirocyclic ring containing one to three heteroatoms selected from the group of O, S and N, the ring being optionally substituted by from 1 to 3 substituents selected from H or $C_1$ to $C_3$ alkyl;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R^3$ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, substituted alkynyl, or $COR^C$;

$R^C$ is H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_4$ aminoalkyl, or substituted $C_1$ to $C_4$ aminoalkyl;

$R^4$ is H, halogen, CN, $NO_2$, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;

$R^5$ is a trisubstituted benzene ring containing the substituents X, Y and Z as shown below:

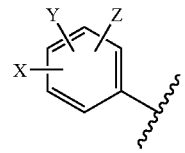

X is taken from the group including halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, $C_1$ to $C_3$ aminoalkyl, substituted $C_1$ to $C_3$ aminoalkyl, $NO_2$, $C_1$ to $C_3$ perfluoroalkyl, 5 membered heterocyclic ring containing 1 to 3 heteroatoms, $COR^D$, $OCOR^D$, or $NR^ECOR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independent substituents taken from the group of H, halogen, CN, $NO_2$, $C_1$ to $C_3$ alkoxy, $C_1$ to $C_3$ alkyl, or $C_1$ to $C_3$ thioalkoxy; or $R^5$ is a five or six membered ring with 1, 2, or 3 heteroatoms from the group including O, S, SO, $SO_2$ or $NR^6$ and containing one or two independent substituents from the group including H, halogen, CN, $NO_2$ and $C_1$ to $C_3$ alkyl, $C_1$ to $C_3$ alkoxy, $R^6$ is H, or $C_1$ to $C_3$ alkyl, $Q^1$ is S, $NR^7$, or $CR^8R^9$;

$R^7$ is selected from CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $SO_2CF_3$, $OR^{11}$ or $NR^{11}R^{12}$;

$R^8$ and $R^9$ are independent substituents from the group including H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN or $CO_2R^{10}$;

$R^{10}$ is $C_1$ to $C_3$ alkyl;

or $CR^8R^9$ comprise a six membered ring as shown by the structure below:

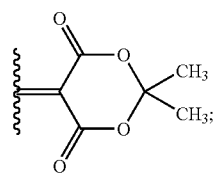

$Q^2$ is selected from the moieties:

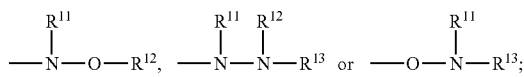

$R^{11}$, $R^{12}$ and $R^{13}$ are independently selected from H, $C_1$ to $C_6$ alkyl, substituted $C_1$ to $C_6$ alkyl, aryl, substituted aryl, heteroaryl, substituted heteroaryl, acyl or sulfonyl; or a pharmaceutically acceptable salt thereof.

Other preferred compounds are those of Formula I wherein:

$R^1$ and $R^2$ and are independently selected from the group of $C_1$ to $C_3$ alkyl, substituted $C_1$ to $C_3$ alkyl, or spirocyclic alkyl constructed by fusing $R^1$ and $R^2$ to form a 3 to 6 membered spirocyclic ring;

$R^3$ is H, OH, $NH_2$, $C_1$ to $C_6$ alkyl, substituted $C_1$ to $C_6$ alkyl, or $COR^C$;

$R^C$ is H, $C_1$ to $C_4$ alkyl, or $C_1$ to $C_4$ alkoxy;

$R^4$ is H, halogen, $NO_2$, $C_1$ to $C_3$ alkyl, or substituted $C_1$ to $C_3$ alkyl;

$R^5$ is a disubstituted benzene ring containing the substituents X, and Y as shown below:

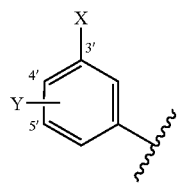

X is selected from the group of halogen, CN, $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms, or $C_1$ to $C_3$ thioalkoxy;

Y is a substituent selected from the group of H, halogen, CN, $NO_2$, $C_1$ to $C_3$ alkoxy, $C_1$ to $C_4$ alkyl, or $C_1$ to $C_3$ thioalkoxy; or $R^5$ is a five membered ring with the structure shown below:

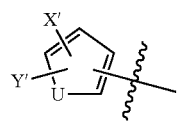

U is O, S, or $NR^6$;

$R^6$ is H, or $C_1$ to $C_3$ alkyl, or $C_1$ to $C_4$ $CO_2$alkyl;

X' is selected from the group including halogen, CN, $NO_2$, $C_1$ to $C_3$ alkyl or $C_1$ to $C_3$ alkoxy;

Y' is selected from the group of H and $C_1$ to $C_4$ alkyl; or $R^5$ is a six membered ring with the structure:

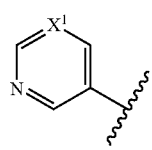

wherein:

$X^1$ is N or $CX^2$, $X^2$ is halogen, CN, or $NO_2$;

Q is S, $NR^7$, or $CR^8R^9$;

$R^7$ is selected from the group of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, or $SO_2CF_3$;

$R^8$ and $R^9$ are independent substituents selected from the group of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN or $CO_2R^{10}$;

$R^{10}$ is $C_1$ to $C_3$ alkyl;

$CR^8R^9$ a six membered ring as shown by the structure below:

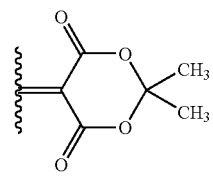

or a pharmaceutically acceptable salts thereof.

Further preferred compounds are those of the formula:

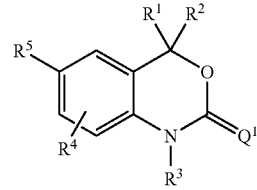

wherein:

$R^1$ and $R^2$ and are independently selected from the group of $CH_3$ and spirocyclic alkyl constructed by fusing $R^1$ and $R^2$ to form a 6 membered spirocyclic ring;

$R^3$ is H, OH, $NH_2$, $CH_3$, substituted methyl, or $COR^C$;

$R^C$ is H, $C_1$ to $C_3$ alkyl, or $C_1$ to $C_4$ alkoxy;

$R^4$ is H, halogen, or $C_1$ to $C_3$ alkyl;

$R^5$ is a disubstituted benzene ring containing the substituents X and Y as shown below:

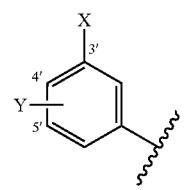

X is selected from the group of halogen, CN, methoxy, $NO_2$, or 2-thiazole;

Y is a substituent selected from H and F; or $R^5$ is a five membered ring with the structure:

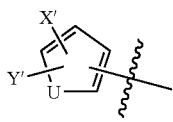

U is O, S, or NH;
X is selected from the group of halogen, CN, $NO_2$;
Y is from the group of H and $C_1$ to $C_4$ alkyl;
$Q^1$ is selected from S, $NR^7$, or $CR^8R^9$;
$R^7$ is selected from the group of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, or $SO_2CF_3$;
$R^8$ and $R^9$ are independent substituents selected from the group of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN or $CO_2R^{10}$;
$R^{10}$ is $C_1$ to $C_3$ alkyl;
or $CR^8R^9$ comprise a six membered ring of the structure below:

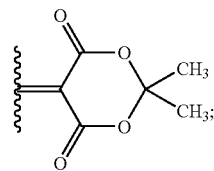

or a pharmaceutically acceptable salt thereof.

Another preferred subgroup of this invention comprises compounds of the formula:

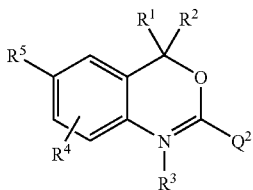

wherein:
$R^1$ and $R^2$ and are independently selected from the group of $CH_3$ and spirocyclic alkyl constructed by fusing $R^1$ and $R^2$ to form a 6 membered spirocyclic ring;
$R^3$ is H, OH, $NH_2$, $CH_3$, substituted methyl, or $COR^C$;
$R^C$ is H, $C_1$ to $C_3$ alkyl, or $C_1$ to $C_4$ alkoxy;
$R^4$ is H, halogen, or $C_1$ to $C_3$ alkyl;
$R^5$ is a disubstituted benzene ring containing the substituents X and Y as shown below:

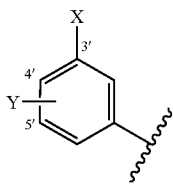

X is selected from the group of halogen, CN, methoxy, $NO_2$, or 2-thiazole;
Y is a substituent selected from H and F; or
$R^5$ is a five membered ring with the structure:

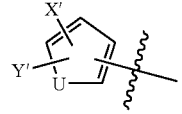

U is O, S, or NH;
X is selected from the group of halogen, CN, $NO_2$;
Y is from the group of H and $C_1$ to $C_4$ alkyl;
$Q^2$ is selected from the moieties:

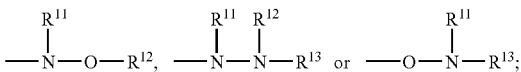

$R^{11}$, $R^{12}$ and $R^{13}$ are independently selected from H, $C_1$ to $C_6$ alkyl, substituted $C_1$ to $C_6$ alkyl, aryl, substituted aryl, heteroaryl, substituted heteroaryl, acyl or sulfonyl; or a pharmaceutically acceptable salt thereof.

The compounds of this invention have been shown to act as competitive inhibitors of progesterone binding to the PR and act as agonists in functional models, either/or in-vitro and in-vivo. These compounds may be used for contraception, in the treatment of fibroids, endometriosis, breast, uterine, ovarian and prostate cancer, and post menopausal hormone replacement therapy.

The compounds of this invention may contain an asymmetric carbon atom and some of the compounds of this invention may contain one or more asymmetric centers and may thus give rise to optical isomers and diastereomers. While shown without respect to the stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

The term "alkyl" is used herein to refer to both straight- and branched-chain saturated aliphatic hydrocarbon groups having one to eight carbon atoms, preferably one to six carbon atoms; "alkenyl" is intended to include both straight- and branched-chain alkyl groups with at least one carbon-carbon double bond and two to eight carbon atoms, preferably one to six carbon atoms; "alkynyl" group is intended to cover both straight- and branched-chain alkyl groups with at least one carbon-carbon triple bond and two to eight carbon atoms, preferably two to six carbon atoms. The terms "substituted alkyl", "substituted alkenyl", and "substituted alkynyl" refer to alkyl, alkenyl, and alkynyl as just described having one or more substituents from the group including halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, and arylthio. These substituents may be attached to any carbon of an alkyl, alkenyl, or alkynyl group provided that the attachment constitutes a stable chemical moiety. The term "aryl" is used herein to refer to an aromatic system which may be a single ring or multiple aromatic rings fused or linked together as such that at least one part of the fused or linked rings forms the conjugated aromatic system. The aryl groups include, but are not limited to, phenyl, naphthyl, biphenyl, anthryl, tetrahydronaphthyl, and phenanthryl. The term "substituted aryl" refers to aryl as just defined having one to four substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, or arylthio. The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S atoms may be oxidized. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl. The term "substituted heterocyclic" is used herein to describe the heterocyclic group just defined having one or more substituents selected from the group which includes halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, or arylthio. The term "alkoxy" is used herein to refer to the OR group, where R is alkyl or substituted alkyl. The term "aryloxy" is used herein to refer to the OR group, where R is aryl or substituted aryl. The term "alkylcarbonyl" is used herein to refer to the RCO group, where R is alkyl or substituted alkyl. The term "alkylcarboxy" is used herein to refer to the COOR group, where R is alkyl or substituted alkyl. The term "aminoalkyl" refers to both secondary and tertiary amines wherein the alkyl or substituted alkyl groups, containing one to eight carbon atoms, which may be either same or different and the point of attachment is on the nitrogen atom. The term "halogen" refers to Cl, Br, F, and I elements.

The compounds of this invention can be prepared following the Schemes illustrated below:

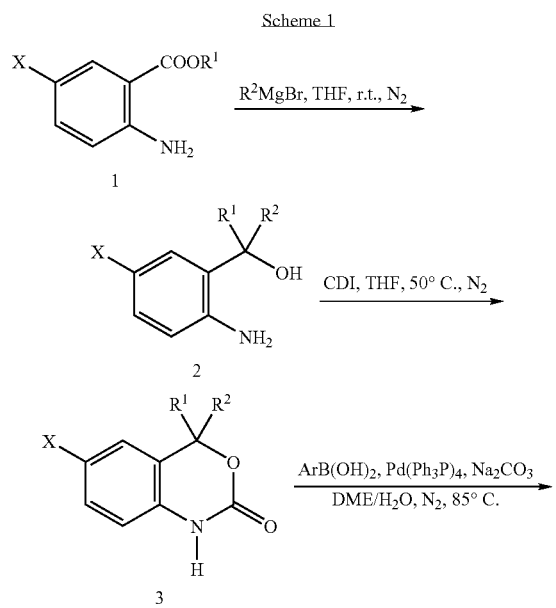

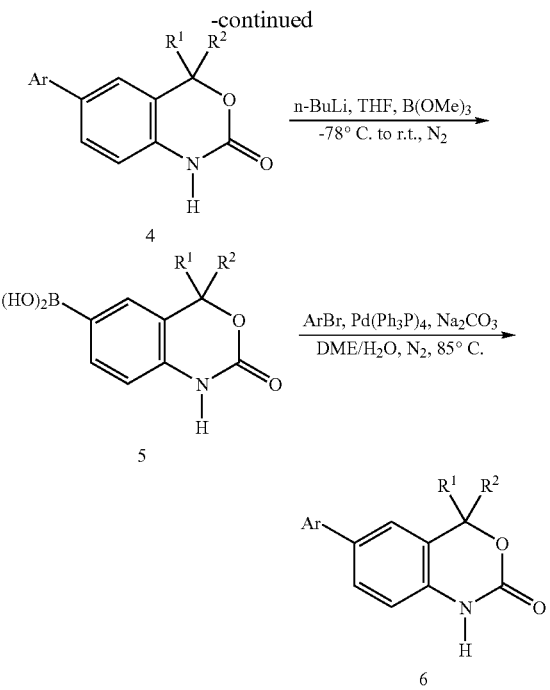

As demonstrated in Scheme I, the compounds of this invention are generally prepared by employing the suitable coupling reaction as a final step. An appropriately substituted ortho-amino benzoic acid or its derivatives such as ethyl ester (X=Br, I, Cl, or a latent coupling precursor such as alkoxy group which can be converted into a OTf group suitable in the coupling reaction) was treated with a suitable organo metallic reagent, e.g. Grignard reagent, in appropriate nonprotic solvents which include, but are not limited to, THF or ether to give ortho-amino carbinol 2 under an inert atmosphere such as argon or nitrogen at −78° C. to room temperature. Ring closure of carbinol 2 to yield benzoxazin-2-ones 3 is commonly effected by a condensing agent such as carbonyldiimidazole, phosgene, dimethylcarbonate, or diethylcarbonate in a suitable nonprotic solvent such as THF at temperatures ranging from room temperature to 65° C. The arylation of benzoxazin-2-ones 3 to yield 4 can be effected by various coupling reactions including Suzuki, Stille reactions. These reactions are commonly performed in the presence of transition metallic catalyst, e.g., palladium or nickel complex often with phosphino ligands, e.g., $Ph_3P$, dppf, dppe or palladium acetate. Under this catalytic condition, an appropriately substituted nucleophilic reagent, e.g., aryl boronic acid, arylstannane, or aryl zinc compound, is coupled with benzoxazinones 3 to give 4. If a base is needed in the reaction, the commonly used bases include, but are not limited to, sodium bicarbonate, sodium carbonate, potassium phosphate, barium carbonate, or potassium acetate. The most commonly used solvents in these reactions include benzene, DMF, isopropanol, ethanol, DME, ether, acetone, or a mixture of above solvents and water. The coupling reaction is generally executed under an inert atmosphere such as nitrogen or argon at temperatures ranging from room temperature to 95° C.

Benzoxazinones 3 can be converted into a nucleophile such as boronic acid which can be coupled with an appropriate electrophile, e.g., aryl bromide or aryl iodide, to yield 4 employing the coupling reaction condition as described above. The transformation of 3 into 5 can be effected by treating 3 with an organo metallic reagent, e.g., n-BuLi, in a nonprotic solvent such as THF or ether followed by quenching the reaction solution with a suitable electrophile, such as trimethyl borate, triisopropyl borate, or zinc chloride at temperatures ranging from −78° C. to room temperature under an inert atmosphere such as argon or nitrogen.

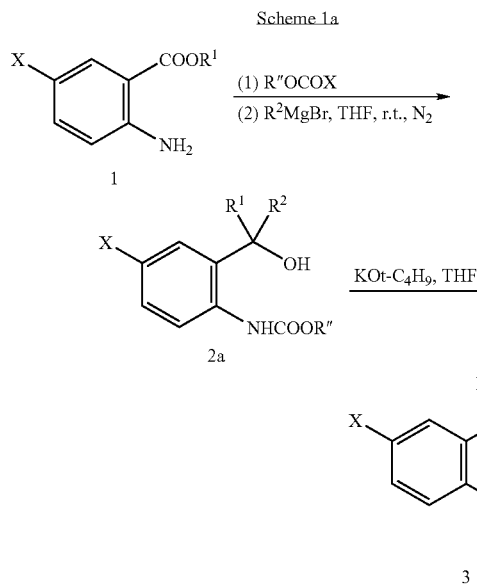

Scheme Ia illustrates an alternative approach leading to the benzoxazinones 3. Thus, an appropriate aniline 1 is protected with a suitable alkoxy carbonyl protective group including but not limited to allenoxy carbonyl, t-butoxy carbonyl, benzoxy carbonyl, ethoxy carbonyl, or methoxy carbonyl in a suitable solvent such as THF, acetonitrile, with or without presence of a base either as a catalyst or as an acid scavenger. The protected aniline is then treated with a suitable organo metallic reagent such as organo lithium agent or Grignard reagent in the same fashion as to prepare compound 2 to give the carbinol 6. The treatment of 2a with a suitable base such as potassium t-butoxide, n-butyl lithium, potassium hydroxide in an appropriate solvent such as toluene, THF, alcohol under an inert atmosphere such as nitrogen or argon at the temperature ranging from room temperature to the boiling point of the relevant solvent affords benzoxazinones 3.

Scheme II describes the procedures to prepare benzoxazinones bearing two different substituents at position-4. The Weinreb amide 8 can be prepared from an appropriately substituted isatoic anhydride 7 when treated with N-, O-dimethylhydroxyl-amine hydrochloride salt in a protic solvent such as ethanol, isopropanol at reflux under an inert atmosphere such as argon or nitrogen. Coupling of amide 8 with an aryl electrophile such as aryl boronic acid or arylstannane to give 9 can be effected by employing a typical coupling reaction such as Suzuki, Stille coupling procedure in a similar fashion as described for the preparation of benzoxazinones 4. Treatment of Weinreb amide 9 with organo metallic compounds, e.g., alkyllithium, alkynyllithium, aryllithium, or their Grignard counterpart in a nonprotic solvent such as THF or ether under an inert atmosphere such as argon or nitrogen at −78° C. to room temperature affords amino ketone 10. Conversion of ketone 10 to carbinol 11 can be effected by treatment of 10 with an organo metallic reagent such as alkyl, alkynyl, or aryl Grignard compound in a nonprotic solvent such as THF or ether under an inert atmosphere such as argon or nitrogen at −78° C. to room temperature. Conversion of ketone 10 to carbinol 11 can also be effected by reduction of ketone group of 10 to the carbinol moiety of 11 using an appropriate reducing reagent such as lithium aluminum hydride, sodium borohydride in a suitable solvent such as THF, ether, or anhydrous alcohol under an inert atmosphere in the temperature range from 0° C. to the boiling point of the solvent. Ring closure of carbinol 11 to produce the compounds of this invention can be accomplished with condensing agents such as carbonyldiimidazole, phosgene, dimethylcarbonate, or diethylcarbonate in a suitable nonprotic solvent such as THF at temperatures ranging from room temperature to 65° C.

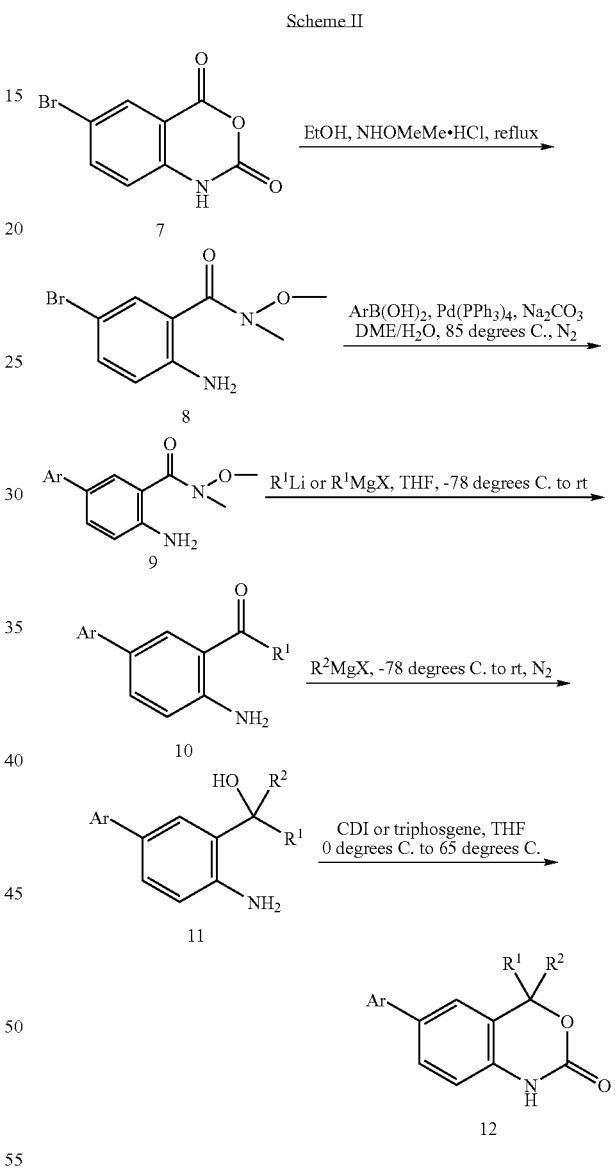

Alternatively, ortho-amino ketone 10 can be prepared by treatment of ortho-amino benzonitrile 14 with an organo metallic compound such as organo lithium reagent or Gringard reagent in a suitable solvent such as THF or ether under an inert atmosphere such as argon or nitrogen at temperatures ranging from −78° C. to room temperature as illustrated in Scheme III. Benzonitrile 14 can be readily prepared from an appropriately substituted benzonitrile such as bromobenzonitrile 13 using a suitable coupling reaction such as Stille or Suzuki protocol carried out in a similar fashion as described for the preparation of the Weinreb amide 9.

Scheme III

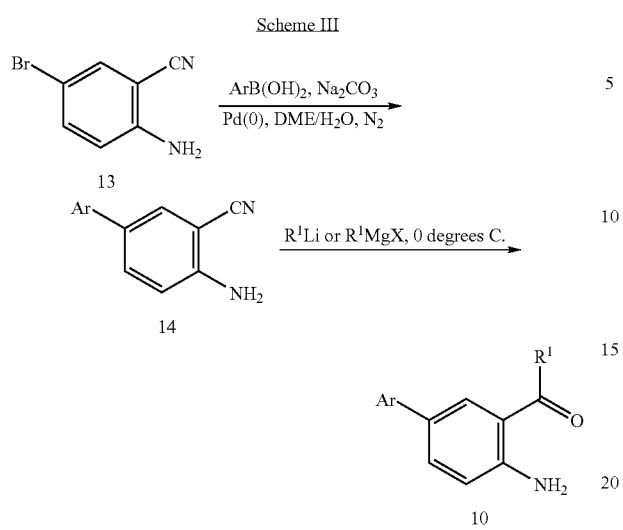

Scheme IV depicts an approach to prepare benzoxazinones with a low perfluoroalkyl substituent at position-4, e.g. R6 is trifluoromethyl group. An appropriately substituted chloroaniline 15 was protected with a suitable protective group such as pivaloyl chloride or di-tert-butyl pyrocarbonate to give protected aniline 16 in a suitable solvent such as acetonitrile, acetone, THF, methylene chloride, or a mixture of solvent such as methylene chloride and water under an inert atmosphere such as argon or nitrogen at temperatures ranging from 0° C. to 70° C. A suitable base such as sodium carbonate, sodium bicarbonate, or potassium carbonate may be needed when the reaction produces an acid as a side-product such as hydrochloride. Treatment of 16 with an appropriate alkyllithium such as n-butyllithium or s-butyllithium followed by reaction with a low perfluorocarboxy derivatives, e.g., trifluoroacetyl chloride, 1-(trifluoroacetyl)-imidazole, or ethyl trifluoroacetate in a nonprotic solvent such as ether or THF under an inert atmosphere such as argon or nitrogen at −78° C. to ambient temperature gives the protective ortho-amino ketones. Subsequent removal of the protecting group can be effected by reaction of protected amino ketones with a suitable acid such as TFA, 3N aqueous hydrochloride solution in a suitable solvent such as methylene chloride or water at 0° C. to boiling point of the solvent to afford ortho-amino ketone 17.

Scheme IV

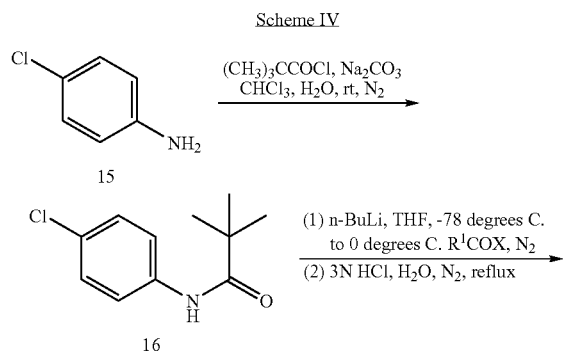

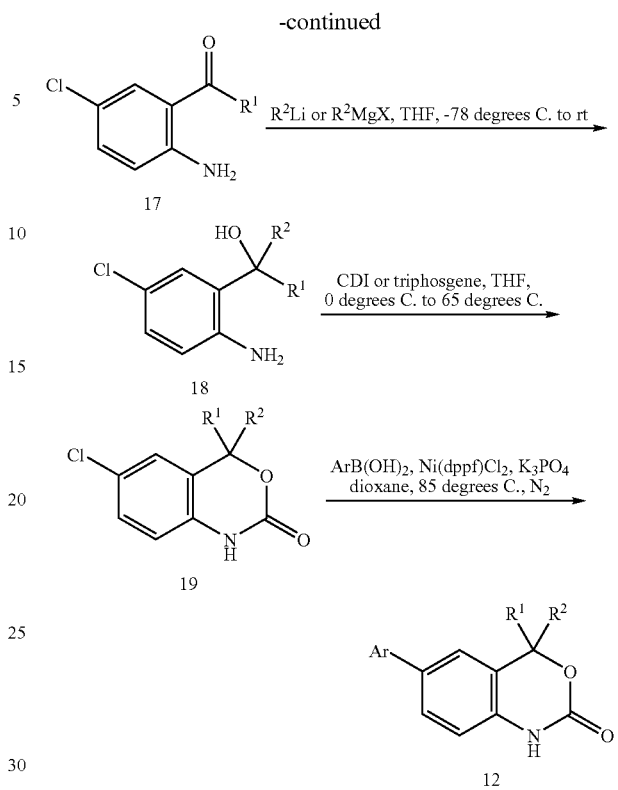

The preparation of 6-chlorobenzoxazinones 19 from 17 can be accomplished in the same fashion as described for the synthesis of benzoxazinone 12 from ketone 10. Coupling of 19 with an aryl group to yield 12 can be effected by a nickel complex catalyzed coupling reaction. The palladium catalysts proved not to be an efficient catalyst in this coupling process. The coupling reaction of 19 with an appropriate aryl boronic acid can be accomplished in the presence of a suitable base such as potassium phosphate and a catalyst of nickel (0 or II) complex, e.g. a nickel complex of 1,2-bis(diphenylphosphino)ethane, 1,1′-bis(diphenylphosphino)ferrocene, or triphenylphosphine. The most commonly used solvents in the reaction include dioxane or THF. The coupling reaction is generally executed under an inert atmosphere such as nitrogen or argon at temperatures ranging from ambient temperature to 95° C.

As described in Scheme V, the conversion of benzoxazin-2-ones 3 or 12 into benzoxazin-2-thiones 20 or 21 can be accomplished by treatment of 3 or 12 with a suitable sulfur reagent such as Lawesson's reagent in a nonprotic solvent such as o-xylene, chlorobenzene, or toluene under an inert atmosphere such as argon or nitrogen at reflux.

Scheme V

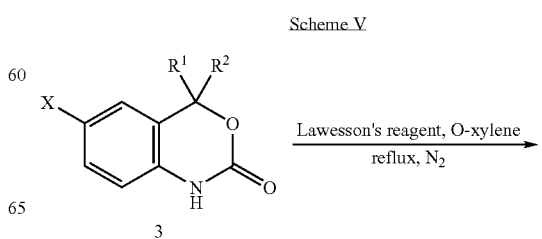

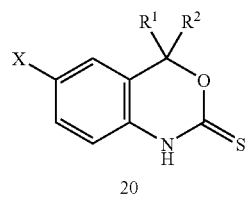

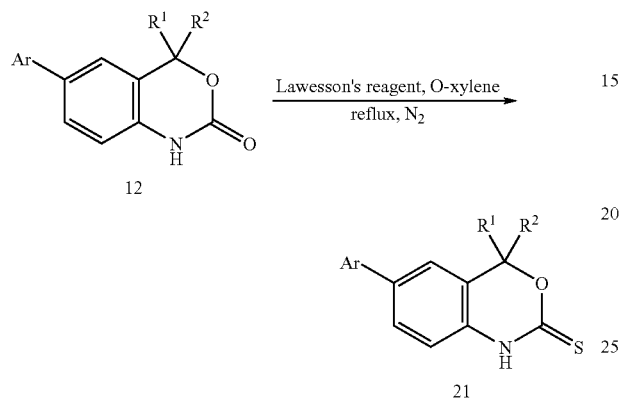

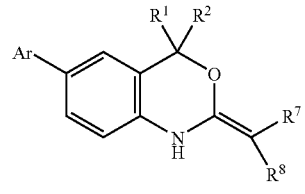

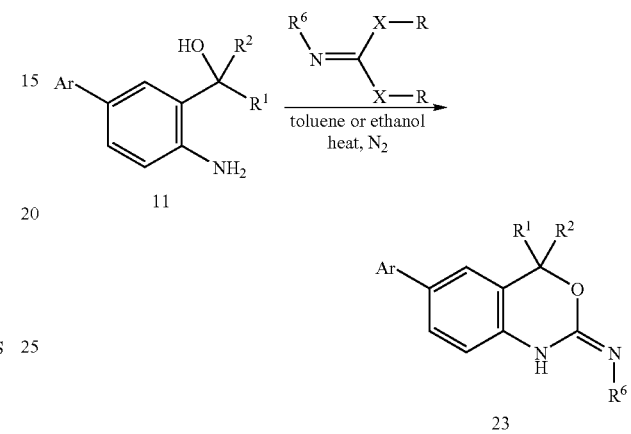

Schemes VI and VII describe the synthesis of other benzoxazinone bioisosteres. Using a similar procedure reported by Kondo et al. (Kondo, et al. *J. Med. Chem.* 33(7), 2012-2015 (1990)) compound 22 can be formed by treatment of amino carbinol 11 with an appropriate ketene-S,S-acetals (at least one of $R_{16}$ or $R_{17}$ is an electron withdrawing group) in a suitable solvent such as toluene or anhydrous ethanol under an inert atmosphere such as nitrogen or argon at reflux. In a similar fashion, compound 23 can be formed by reaction of amino carbinol 11 with an appropriate imino-S,S-acetals or imino-acetals ($R_{18}$ is an electron withdrawing group) employing a procedure similar to that of Evers, et al. (Evers, et al. *I. Prakt. Chem.* 333(5), 699-710 (1991)) or Haake et al. (Haake et al. *Synthesis-Stuttgart* 9, 753-758 (1991)) in a suitable solvent such as ethanol under an inert atmosphere such as argon or nitrogen at reflux. Other procedures (e.g. Wrobel et al. *J. Med. Chem.* 32, 2493(1989)) potentially leading to compounds 22 or 23 from 20 or 21 is illustrated in scheme VIIa. Thus, compound 20 or 21 is alkylated with an appropriate alkylating agent such as the Meerwein reagent in a suitable solvent such as methylene chloride. This is then followed by a nucleophilic replacement of an appropriate nucleophile such as carbon anion or a amine base to give compounds 22 or 23, which may produce either tautomeric form of compounds 22 or 23.

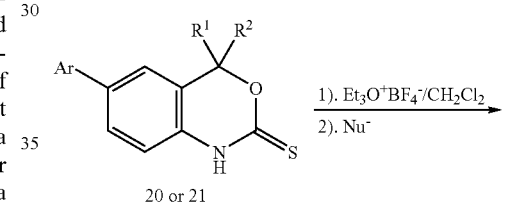

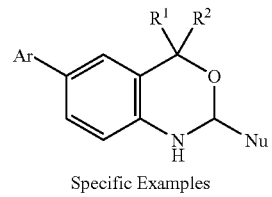

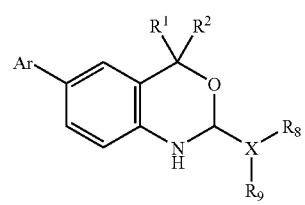

Scheme VIIa

As illustrated in Scheme VIII, the compound 21 can be further derivatized at position-1 via numerous approaches leading to a variety of the novel cyclothiocarbamate derivatives including 1-alkyl, substituted 1-alkyl, 1-carbonyl, substituted 1-carbonyl, 1-carboxy, substituted 1-carboxy derivatives. For example, alkyl or substituted alkyl derivatives 24 can be formed by treatment of thiocarbamate 12 or 6 with a suitable base such as sodium hydride in suitable solvent such as DMF under an inert atmosphere, such as argon or nitrogen, followed by addition of an appropriate electrophile such as alkyl or substituted alkyl bromide, iodide, or triflate. Such a Scheme VI

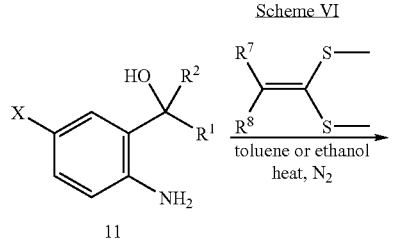

transformation of 21 at position-1 can also be effected using a biphasic condition as indicated in Scheme VIII in which alkylation is executed using a biphasic catalyst such as tributylammonium bromide in a suitable solvent such as acetonitrile. A further example of such a modification includes, but is not limited to, heating 21 with triethyl orthoformate to afford 1-substituted derivatives 24. (Scheme VIII)

The acylation or carboxylation of the compound 21 at position-1 to give compound 25 can be readily effected by treatment of 12 or 6 with a suitable acylating or carboxylating reagent such as di-t-butyl dicarbonate in the presence of a suitable basic catalyst such as DMAP in a suitable solvent such as acetonitrile under an inert atmosphere such as argon or nitrogen. The amination of position-1 of compound 21 to give compound 26 can be furnished using a suitable aminating reagent such as chloroamine in the presence of a suitable base such as sodium hydride in a suitable solvent such as THF or diethyl ether following the literature procedure (Metlesics et al. *J. Org. Chem.* 30, 1311(1965)).

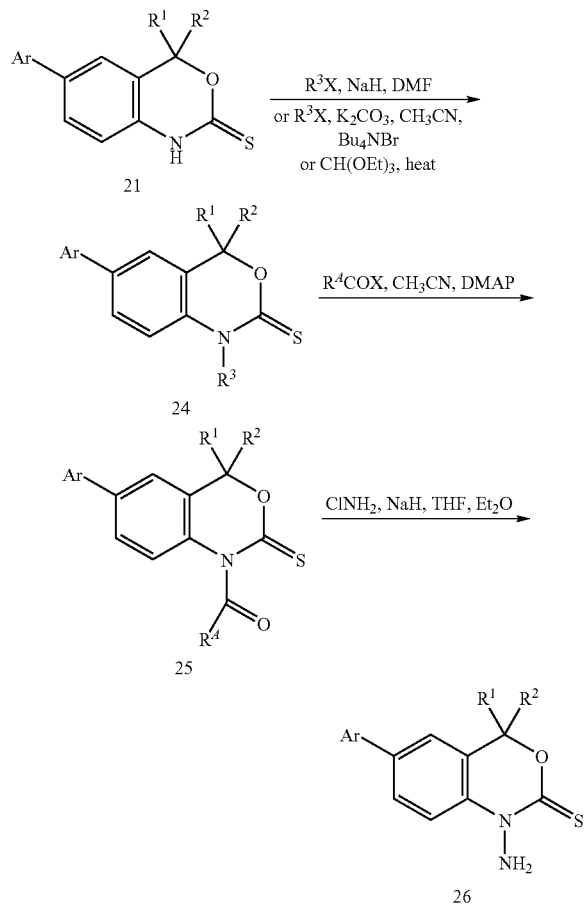

The compounds of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "pro-drug" forms, which, when administered in such form, convert to the active moiety in vivo.

This invention includes pharmaceutical compositions and treatments which comprise administering to a mammal a pharmaceutically effective amount of one or more compounds as described above as agonists of the progesterone receptor.

The progesterone receptor agonists of this invention, used alone or in combination, can be utilized in methods of contraception and the treatment and/or prevention of dysfunctional bleeding, uterine leiomyomata, endometriosis, polycystic ovary syndrome, and carcinomas and adenocarcinomas of the endometrium, ovary, breast, colon, and prostate. Additional uses of the invention include stimulation of food intake.

This invention also includes pharmaceutical compositions utilizing the compounds herein, preferably in combination with a pharmaceutically acceptable carrier or excipient. When the compounds are employed for the above utilities, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals, the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvents customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The following examples illustrate preparation of compounds of the invention.

EXAMPLE 1

2-(2-Amino-5-bromophenyl)propan-2-ol

A solution of 2-amino-5-bromobenzoic acid (10 g, 46 mmol) in dry THF (200 mL) was treated at −78° C. under nitrogen with a solution of methylmagnesium bromide in ether (3.0 M, 90 mL, 270 mmol). The reaction mixture was slowly warmed to ambient temperature, kept stirring for 48 hours under nitrogen and then poured into a cold 0.5 N aqueous hydrochloride solution (300 mL). The mixture was neutralized with aqueous 1 N sodium hydroxide solution and ethyl acetate (300 mL) was added. The organic layer was separated and aqueous layer was extracted with ethyl acetate (3×100 mL). The combined organic layers were washed with brine and dried (MgSO$_4$). After removal of solvent in vacuo, the residue was purified by a silica gel flash chromatography (hexane:ethyl acetate/3:2) to give 2-(2-amino-5-bromophenyl)propan-2-ol as an off-white solid (6 g, 57%): mp 62-63° C.; $^1$H-NMR (CDCl$_3$) δ 7.19 (d, 1H, J=2.3 Hz), 7.12 (dd, 1H, J=8.4, 2.3 Hz), 6.51 (d, 1H, J=8.4 Hz), 4.70 (s, 2H), 1.82 (s, 1H), 1.65 (s, 6H).

EXAMPLE 2

6-Bromo-4,4-dimethyl-1,4-dihydro-benzo[d][1,3]oxazin-2-one

To a solution of 2-(2-amino-5-bromophenyl)propan-2-ol (18 g, 78 mmol) in dry THF (150 mL) was added 1,1'-carbonyldiimidazole (15.5 g, 94 mmol) under nitrogen. The reaction solution was heated at 50° C. overnight. The solvent was removed in vacuo and the residue was dissolved in ethyl acetate (100 mL). The solution was washed with 1N aqueous hydrochloride solution (2×40 mL), brine (20 mL), and dried with MgSO$_4$. After removal of solvent in vacuo, 6-bromo-4,4-dimethyl-1,4-dihydro-benzo[d][1,3]-oxazin-2-one was obtained as a white solid (20 g, 100%): mp 199-200° C.; $^1$H-NMR (DMSO-d$_6$) δ 10.32 (s, 1H, D$_2$O exchangeable), 7.48 (d, 1H, J=2.1 Hz), 7.43 (dd, 1H, J=8.5, 2.1 Hz), 6.84 (d, 1H, J=8.4 Hz), 1.61 (s, 6H).

EXAMPLE 3

(1,4-Dihydro-4,4-dimethyl-2-oxo-2H-3,1-benzoxazin-6-yl)boronic acid

To a solution of 6-bromo-4,4-dimethyl-1,4-dihydro-benzo[d][1,3]oxazin-2-one (2 g, 7.8 mmol) in anhydrous THF (60 mL) was added a solution of n-BuLi in hexane (10 M, 2.4 mL, 24 mmol) at −78° C. under nitrogen. After stirring at −78° C. for 30 minutes, a slurry was obtained and treated with triisopropyl borate (6.5 mL, 28 mmol). The reaction solution was slowly warmed to ambient temperature and quenched with 1N aqueous hydrochloric acid solution (60 mL). Ethyl acetate (100 mL) was added, the organic layer was separated, and the aqueous layer was extracted with ethyl acetate (3×60 mL). The combined organic layer was washed with brine and dried with MgSO$_4$. The solvent was removed in vacuo and the residue was purified by a silica gel flash chromatography (ethyl acetate:hexane/2:1) to afford (1,4-dihydro-4,4-dimethyl-2-oxo-2H-3,1-benzoxazin-6-yl)boronic acid as a white solid (1.4 g, 81%): mp 249-250° C.; $^1$H-NMR (DMSO-d$_6$) δ 10.21 (s, 1H, D$_2$O exchangeable), 7.90-7.95 (br s, 2H, D$_2$O exchangeable), 7.67 (m, 2H), 6.79 (d, 1H, J=7.8 Hz), 1.61 (s, 6H); MS (ESI) m/z 222 ([M+H]$^+$, 87%).

EXAMPLE 4

6-(3-Chlorophenyl)-4,4-dimethyl-1,4-dihydrobenzo[d][1,3]oxazin-2-one

Procedure A

A mixture of 6-bromo-4,4-dimethyl-1,4-dihydro-benzo[d][1,3]oxazin-2-one (1.5 g, 5.9 mmol), 3-chlorophenyl boronic acid (1.83 g, 11.7 mmol), tetrakis(triphenylphosphine)-palladium (0) (0.35 g, 0.3 mmol), and sodium carbonate (2.48 g, 23.4 mmol) in a mixture of DME and water (40 mL/10 mL) was degassed to remove the oxygen and then heated at 85° C. under a blanket of nitrogen for 3 hours. The reaction mixture was cooled to ambient temperature and quenched with a saturated aqueous ammonium chloride solution (20 mL). Ethyl acetate (50 mL) was added and the organic layer was separated. The aqueous layer was extracted with ethyl acetate (3×15 mL). The combined organic layers were washed with brine and dried with MgSO$_4$. The solvent was removed in vacuo and the residue was purified by silica gel flash chromatography (hexane:ethyl acetate/2:1) to afford 6-(3-chlorophenyl)-4,4-dimethyl-1,4-dihydrobenzo[d][1,3]oxazin-2-one as a yellowish solid (1.4 g, 82%): mp 158-159° C.; $^1$H-NMR (DMSO-d$_6$) δ 10.31 (s, 1H, D$_2$O exchangeable), 7.75 (s, 1H), 7.61 (m, 3H), 7.46 (t, 1H, J=7.9 Hz), 7.39 (dd, 1H, J=7.0, 1.1 Hz), 6.96 (d, 1H, J=8.6 Hz), 1.68 (s, 6H); Anal. Calcd. For C$_{16}$H$_{14}$ClNO$_2$.0.1 H$_2$O: C, 66.37; H, 4.94; N, 4.84. Found: C, 66.14; H, 4.61; N, 4.71.

EXAMPLE 5

6-(3-Bromo-5-fluorophenyl)-4,4-dimethyl-1,4-dihydrobenzo[d][1,3]oxazin-2-one

Procedure B

A mixture of (1,4-dihydro-4,4-dimethyl-2-oxo-2H-3,1-benzoxazin-6-yl)boronic acid (2.22 g, 10 mmol), 1,3-dibromo-5-fluorobenzene (3.05 g, 12 mmol), tetrakis(triphenylphosphine)palladium (0) (0.6 g, 0.52 mmol), and sodium carbonate (2.2 g, 21 mmol) in a mixture of DME and water (70 mL/15 mL) was degassed to remove the oxygen and then heated at 85° C. under a blanket of nitrogen for 3 hours. The reaction mixture was cooled to ambient temperature and quenched with a saturated aqueous ammonium chloride solution (20 mL). Ethyl acetate (100 mL) was added and organic layer was separated. The aqueous layer was extracted with ethyl acetate (3×30 mL). The combined organic layers were washed with brine and dried with $MgSO_4$. The solvent was removed in vacuo and the residue was purified by a silica gel flash chromatography (hexane:ethyl acetate/1:1) to give 6-(3-bromo-5-fluorophenyl)-4,4-dimethyl-1,4-dihydrobenzo[d][1,3]oxazin-2-one as a white solid (1.4 g, 40%): mp 182-183° C.; $^1$H-NMR (DMSO-$d_6$) δ 10.36 (s, 1H, $D_2O$ exchangeable), 7.78 (s, 1H), 7.58-7.65 (m, 3H), 7.49 (dd, 1H, J=8.3, 1.8 Hz), 6.96 (d, 1H, J=8.5 Hz), 1.69 (s, 6H); $^{19}$F-NMR (DMSO-$d_6$) δ-112.46 (m, 1F); MS (CI) m/z 352 ([M+H]$^+$, 78%), 350 ([M+H]$^+$, 75%). Anal. Calcd. For $C_{16}H_{13}BrFNO_2$: C, 54.88; H, 3.74; N, 4.00. Found: C, 54.83; H, 3.82; N, 3.95.

EXAMPLE 6

3-(4,4-Dimethyl-2-oxo-1,4-dihydro-2H-benzo[d][1,3]oxazin-6-yl)-5-fluorobenzonitrile A mixture of 6-(3-bromo-5-fluorophenyl)-4,4-dimethyl-2H-benz[d][1,3]oxazin-2-one (1 g, 2.8 mmol), zinc cyanide (0.2 g, 1.7 mmol), and tetrakis(triphenylphosphine)-palladium (0) (0.2 g, 0.17 mmol) in dry DMF (20 mL) was degassed to remove oxygen and was then heated at 85° C. under a blanket of nitrogen for 6.5 hours. The reaction solution was cooled to room temperature and poured onto a cold saturated aqueous ammonium chloride solution (100 mL). The white precipitate appeared and was collected on a filter. The white solid was washed with distilled water (3×20 mL) and dissolved in a mixture of ethyl acetate (10 mL) and methanol (10 mL). The solution was applied on a pad of silica gel and eluted with a mixture of ethyl acetate and hexane (1:1). After solvent was removed, 3-(4,4-dimethyl-2-oxo-1,4-dihydro-2H-benzo[d][1,3]oxazin-6-yl)-5-fluorobenzonitrile was obtained as a white solid (0.7 g, 84%): mp 253-254° C.; $^1$H-NMR (DMSO-$d_6$) δ 10.4 (s, 1H, $D_2O$ exchangeable), 8.13 (s, 1H), 7.92 (m, 1H), 7.82 (m, 1H), 7.73 (m, 2H), 6.98 (d, 1H, J=8.2 Hz), 1.68 (s, 6H); $^{19}$F-NMR (DMSO-$d_6$) δ-112.25 (m, 1F); MS (EI) m/z 296 (M$^+$, 65%); Anal. Calcd. For $C_{17}H_{13}FN_2O_2$: C, 68.91; H, 4.42; N, 9.45. Found: C, 68.85; H, 4.58; N, 9.14.

EXAMPLE 7

4-(4,4-Dimethyl-2-oxo-1,4-dihydro-2H-benzo[d][1,3]oxazin-6-yl)-thiophene-2-carbonitrile The product was prepared, from (1,4-dihydro-4,4-dimethyl-2-oxo-2H-3,1-benzoxazin-6-yl)boronic acid and 4-bromo-2-thiophenecarbonitrile according to the procedure outlined in Example 5, as a yellowish solid: mp 230-231° C. (decomposed); $^1$H-NMR (CDCl$_3$) δ 8.32 (s, 1H, $D_2O$ exchangeable), 7.83 (d, 1H, J=1.5 Hz), 7.61 (d, 1H, J=1.4 Hz), 7.43 (dd, 1H, J=8.2, 1.9 Hz), 7.29 (d, 1H, J=1.8 Hz), 6.85 (d, 1H, J=8.2 Hz), 1.78 (s, 6H); MS (EI) m/z 283 ([M−H]$^-$, 100%); Anal. Calcd. For $C_{15}H_{12}N_2O_2S.0.2H_2O$: C, 62.57; H, 4.34; N, 9.73. Found: C, 62.48; H, 4.31; N, 9.64.

EXAMPLE 8

6-(3-Chlorophenyl)-4,4-dimethyl-1,4-dihydro-benzo[d][1,3]oxazin-2-thione

A mixture of 6-(3-chlorophenyl)-4,4-dimethyl-1,4-dihydro-benzo[d]-[1,3]oxazin-2-one (0.15 g, 0.5 mmol) and Lawesson's reagent (0.24 g, 0.6 mmol) in anhydrous o-xylene was heated at reflux under nitrogen for 3 hours. The solvent was removed and the residue was purified by a flash chromatography (silica gel, hexane:ethyl acetate/6:1) to afford the title compound as a white solid (80 mg, 52%): mp 183-184° C.; $^1$H-NMR (DMSO-$d_6$) δ 12.25 (s, 1H, $D_2O$ exchangeable), 7.78 (t, 1H, J=1.7 Hz), 7.63-7.70 (m, 3H), 7.49 (t, 1H, J=7.8 Hz), 7.42 (d, 1H, J=8.1 Hz), 7.12 (d, J=8.8 Hz), 1.72 (s, 6H); MS (EI) m/z 303 (M$^+$, 100%), 305 (M$^+$, 32%); Anal. Calcd. For $C_{16}H_{14}ClNOS$: C, 63.26; H, 4.64; N, 4.61. Found: C, 63.37; H, 4.62; N, 4.54.

EXAMPLE 9

4-(4,4-Dimethyl-2-thioxo-1,4-dihydro-2H-benzo[d][1,3]oxazin-6-yl)-thiophene-2-carbonitrile A mixture of 4-(4,4-dimethyl-2-oxo-1,4-dihydro-2H-benzo[d][1,3]oxazin-6-yl)-thiophene-2-carbonitrile (0.23 g, 0.8 mmol) and Lawesson's reagent (0.38 g, 0.96 mmol) in anhydrous o-xylene was heated to reflux under nitrogen for 3 hours. The solvent was removed in vacuo and the residue was purified by a flash chromatography (silica gel, hexane:ethyl acetate/3:1) to afford the title compound as a yellow solid (85 mg, 35%): mp 242-243° C.; $^1$H-NMR (DMSO-$d_6$) δ 12.22 (s, 1H, $D_2O$ exchangeable), 8.50 (d, 1H, J=1.2 Hz), 8.37 (d, 1H, J=1.0 Hz), 7.71 (m, 2H), 7.09 (d, 1H, J=8.0 Hz), 1.69 (s, 6H); MS (APCI) m/z 301 ([M+H]$^+$, 100%); Anal. Calcd. For $C_{15}H_{12}N_2OS_2$: C, 59.97; H, 4.03; N, 9.33. Found: C, 59.67; H, 3.85; N, 9.14.

EXAMPLE 10

6-Bromo-4,4-dimethyl-1,4-dihydro-benzo[d][1,3]oxazin-2-thione

The product was prepared, from 6-bromo-4,4-dimethyl-1,4-dihydro-benzo[d][1,3]oxazin-2-one and Lawesson's reagent using the procedure of Example 9, as a white solid: mp 221-222.5° C.; $^1$H-NMR (CDCl$_3$) δ 9.38 (s, 1H, $D_2O$ exchangeable), 7.42 (dd, 1H, J=8.5, 2.1 Hz), 7.29 (d, 1H, J=2.0 Hz), 6.76 (d, 1H, J=8.4 Hz), 1.76 (s, 6H); MS (EI) m/z 272 ([M+H]$^+$, 94%), 274 ([M+H]$^+$, 100%).

EXAMPLE 11

3-(4,4-Dimethyl-2-thioxo-1,4-dihydro-2H-benzo[d][1,3]oxazin-6-yl)-5-fluorobenzonitrile The product was prepared, from 3-(4,4-dimethyl-2-oxo-1,4-dihydro-2H-benzo[d][1,3]oxazin-6-yl)-5-fluorobenzonitrile and Lawesson's reagent using the procedure of Example 9, as a yellow solid: 248-249° C.; $^1$H-NMR (DMSO-$d_6$) δ 12.3 (s, 1H), 8.15 (bs, 1H), 8.02 (d, 1H, J=10.48 Hz), 7.85-7.78 (m, 3H), 7.13 (d, 1H, J=8.92 Hz), 1.71 (s, 6H); MS (APCI) m/z 313 ([M+H]$^+$, 100%); Anal. Calcd. For $C_{17}H_{13}FN_2OS$: C, 65.37; H, 4.19; N, 8.97. Found: C, 65.26; H, 4.31; N, 8.61.

EXAMPLE 12

3-(4,4-Dimethyl-2-oxo-1,4-dihydro-2H-benzo[d][1,3]oxazin-6-yl)-benzonitrile

A mixture of (1,4-dihydro-4,4-dimethyl-2-oxo-2H-3,1-benzoxazin-6-yl)boronic acid (2.22 g, 10 mmol), 3-bromobenzonitrile (2.18 g, 12 mmol), tetrakis(triphenylphosphine)palladium (0) (0.6 g, 0.52 mmol), and sodium carbonate (2.2 g, 21 mmol) in a mixture of DME and water (70 mL/15 mL) was degassed to remove the oxygen and then heated at 85° C. under a blanket of nitrogen for 3 hours. The reaction mixture was cooled to ambient temperature and quenched with a saturated aqueous ammonium chloride solution (20 mL). Ethyl acetate (100 mL) was added and the organic layer was separated. The aqueous layer was extracted with ethyl acetate (3×30 mL). The combined organic layers were washed with brine and dried with $MgSO_4$. The solvent was removed in vacuo and the residue was purified by a silica gel flash chromatography (hexane:ethyl acetate/1:1) to give 3-(4,4-dimethyl-2-oxo-1,4-dihydro-2H-benzo[d][1,3]oxazin-6-yl)-benzonitrile as an off-white solid (0.7 g, 25%): mp 236-237° C.; $^1$H-NMR (DMSO-$d_6$) δ 10.34 (s, 1H, $D_2O$ exchangeable), 8.21 (s, 1H), 8.02 (d, 1H, J=8.1 Hz), 7.79 (d, 1H, J=7.7 Hz), 7.60-7.70 (m, 3H), 6.98 (d, 1H, J=8.2 Hz), 1.71 (s, 6H); Anal. Calcd. For $C_{17}H_{14}N_2O_2$·0.1 $H_2O$: C, 72.89; H, 5.11; N, 10.00. Found: C, 72.75; H, 5.05; N, 9.65.

EXAMPLE 13

3-(4,4-Dimethyl-2-thioxo-1,4-dihydro-2H-benzo[d][1,3]oxazin-6-yl)-benzonitrile

A mixture of 3-(4,4-dimethyl-2-oxo-1,4-dihydro-2H-benzo[d][1,3]oxazin-6-yl)-benzonitrile (1 g, 3.6 mmol) and Lawesson's reagent (1.8 g, 4.3 mmol) in o-xylene (30 mL) was heated at reflux overnight. The reaction mixture was cooled to room temperature, poured into ethyl acetate (50 mL) and washed with 1 N HCl (2×20 mL). The organic layer was dried over sodium sulfate and concentrated. The residue was purified via flash chromatography (silica gel, 20% ethyl acetate/hexane) to give 3-(4,4-dimethyl-2-thioxo-1,4-dihydro-2H-benzo[d][1,3]oxazin-6-yl)-benzonitrile (0.21 g, 20%) as a white solid: mp 236-237° C.; 1H-NMR (DMSO-$d_6$) δ 12.3 (s, 1H), 8.24 (s, 1H), 8.05 (d, 1H, J=8.07 Hz), 7.82 (d, 1H, J=7.68 Hz), 7.74-7.64 (m, 3H), 7.14 (d, 1H, J=8.78 Hz), 1.71 (s, 6H); MS (APCI) m/z 295 ([M+H]$^+$, 100%); Anal. Calcd. For $C_{17}H_{14}N_2OS$: C, 69.36; H, 4.79; N, 9.52. Found: C, 68.35; H, 4.91; N, 9.07

EXAMPLE 14

Potency in the Relevant Assays

The compounds of this invention were tested in the relevant assay as described below and their potency are in the range of 0.01 nM to 5 μM in the in vitro assays and 0.001 to 300 mg/kg in the in vivo assays. The selected examples are listed in Table 1 below.

TABLE 1

| Compound | $R_1$ | $R_2$ | $R_3$ | HPR CV-1 $EC_{50}$ (nM) | Ovulation Inhibition $ED_{100}$ (mg/kg) |
|---|---|---|---|---|---|
| 1 | 3-chlorophenyl | Me | Me | 0.65 | ND* |
| 2 | 4-(2-cyanothio-phene) | Me | Me | 0.3 | 1 |
| 3 | 3-cyano-5-fluoro-phenyl | Me | Me | 5.1 | ND |
| 4 | 3-cyanophenyl | Me | Me | 0.4** | |

*ND, not determined;
**alkaline phosphatase data.

(1) T47D Cell Proliferation Assay

The objective of this assay is the determination of progestational and antiprogestational potency by using a cell proliferation assay in T47D cells. A compound's effect on DNA synthesis in T47D cells is measured. The materials and methods used in this assay are as follows.

a. Growth Medium: DMEM:F12 (1:1) (GIBCO, BRL) supplemented with 10% (v/v) fetal bovine serum (not heat-inactivated), 100 U/ml penicillin, 100 mg/ml streptomycin, and 2 mM GlutaMax (GIBCO, BRL).

b. Treatment Medium: Minimum Essential Medium (MEM) (#51200-038GIBCO, BRL) phenol red-free supplemented with 0.5% charcoal stripped fetal bovine serum, 100 U/ml penicillin, 200 mg/ml streptomycin, and 2 mM GlutaMax (GIBCO, BRL).

c. Cell Culture: Stock T47D cells are maintained in growth medium. For BrdU incorporation assay, cells are plated in 96-well plates (Falcon, Becton Dickinson Labware) at 10,000 cells/well in growth medium. After overnight incubation, the medium is changed to treatment medium and cells are cultured for an additional 24 hr before treatment. Stock compounds are dissolved in appropriate vehicle (100% ethanol or 50% ethanol/50% DMSO), subsequently diluted in treatment medium and added to the cells. Progestin and antiprogestin reference compounds are run in full dose-response curves. The final concentration of vehicle is 0.1%. In control wells, cells receive vehicle only. Antiprogestins are tested in the presence of 0.03 nM trimegestone, the reference progestin agonist. Twenty-four hours after treatment, the medium is discarded and cells are labeled with 10 mM BrdU (Amersham Life Science, Arlington Heights, Ill.) in treatment medium for 4 hr.

d. Cell Proliferation Assay

At the end of BrdU labeling, the medium is removed and BrdU incorporation is measured using a cell proliferation ELISA kit (#RPN 250, Amersham Life Science) according to manufacturer's instructions. Briefly, cells are fixed in an ethanol containing fixative for 30 min, followed by incubation in a blocking buffer for 30 min to reduce background. Peroxidase-labeled anti-BrdU antibody is added to the wells and incubated for 60 min. The cells are rinsed three times with PBS and incubated with 3,3',5,5'-tetramethylbenzidine (TMB) substrate for 10-20 min depending upon the potency of tested compounds. Then 25 μl of 1 M sulfuric acid is added to each well to stop color reaction and optical density is read in a plate reader at 450 nm within 5 min.

e. Analysis of Results

Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the transformed values. JMP software (SAS Institute, Inc.) is used for both one-way analysis of variance and non-linear dose response analyses in both single does and dose response studies.

f. Reference Compounds: Trimegestone and medroxyprogesterone acetate (MPA) are reference progestins and RU486 is the reference antiprogestin. All reference compounds are run in full dose-response curves and the $EC_{50}$ or $IC_{50}$ values are calculated.

TABLE 2

Estimated $EC_{50}$, standard error (SE), and 95% confidence intervals (CI) for individual studies

| Compound | Exp | $EC_{50}$ (nM) | SE | 95% CI lower | 95% CI upper |
|---|---|---|---|---|---|
| Trimegestone | 1 | 0.017 | 0.003 | 0.007 | 0.040 |
| | 2 | 0.014 | 0.001 | 0.011 | 0.017 |
| | 3 | 0.019 | 0.001 | 0.016 | 0.024 |
| MPA | 1 | 0.019 | 0.001 | 0.013 | 0.027 |
| | 2 | 0.017 | 0.001 | 0.011 | 0.024 |

TABLE 3

Estimated $IC_{50}$, standard error, and 95% confident interval for the antiprogestin, RU486

| Compound | Exp | $IC_{50}$ (nM) | SE | 95% CI lower | 95% CI upper |
|---|---|---|---|---|---|
| RU486 | 1 | 0.011 | 0.001 | 0.008 | 0.014 |
| | 2 | 0.016 | 0.001 | 0.014 | 0.020 |
| | 3 | 0.018 | 0.001 | 0.014 | 0.022 |

$EC_{50}$: Concentration of a compound that gives half-maximal increase in BrdU incorporation with SE; $IC_{50}$: Concentration of a compound that gives half-maximal decrease in 0.1 trimegestone induced BrdU incorporation with SE (2) Rat Decidualization Assay The objective of this procedure is used to evaluate the effect of progestins and antiprogestins on rat urine decidualization and compare the relative potencies of various test compounds. The materials and methods used in this assay are as follows.

a. Methods: Test compounds are dissolved in 100% ethanol and mixed with corn oil (vehicle). Stock solutions of the test compounds in oil (Mazola™) are then prepared by heating (~80° C.) the mixture to evaporate ethanol. Test compounds are subsequently diluted with 100% corn oil or 10% ethanol in corn oil prior to the treatment of animals. No difference in decidual response was found when these two vehicles were compared.

b. Animals (RACUC protocol #5002: Ovariectomized mature female Sprague-Dawley rats (~60-day old and 230 g) are obtained from Taconic (Taconic Farms, N.Y.) following surgery. Ovariectomy is performed at least 10 days prior to treatment to reduce circulating sex steroids. Animals are housed under 12 hr light/dark cycle and given standard rat chow and water ad libitum.

c. Treatment: Rats are weighed and randomly assigned to groups of 4 or 5 before treatment. Test compounds in 0.2 ml vehicle are administered by subcutaneous injection in the nape of the neck or by gavage using 0.5 ml. The animals are treated once daily for seven days. For testing antiprogestins, animals are given the test compounds and a $EC_{50}$ dose of progesterone (5.6 mg/kg) during the first three days of treatment. Following decidual stimulation, animals continue to receive progesterone until necropsy four days later.

d. Dosing: Doses are prepared based upon mg/kg mean group body weight. In all studies, a control group receiving vehicle is included. Determination of dose-response curves is carried out using doses with half log increases (e.g. 0.1, 0.3, 1.0, 3.0 mg/kg).

e. Decidual Induction: Approximately 24 hr after the third injection, decidualization is induced in one of the uterine horns by scratching the antimesometrial luminal epithelium with a blunt 21 G needle. The contralateral horn is not scratched and serves as an unstimulated control. Approximately 24 hr following the final treatment, rats are sacrificed by $C_{02}$ asphyxiation and body weight measured. Uteri are removed and trimmed of fat. Decidualized (D-horn) and control (C-horn) uterine horns are weighed separately.

f. Analysis of Results:

The increase in weight of the decidualized uterine horn is calculated by D-horn/C-horn and logarithmic transformation is used to maximize normality and homogeneity of variance. The Huber M-estimator is used to down weight the outlying transformed observations for both dose-response curve fitting and one-way analysis of variance. JMP software (SAS Institute, Inc.) is used for both one-way ANOVA and non-linear dose-response analyses.

g. Reference Compounds: All progestin reference compounds were run in full dose-response curves and the $EC_{50}$ for uterine wet weight were calculated.

TABLE 4

Estimated $EC_{50}$, standard error (SE), and 95% confidence intervals for individual studies

| Compound | Exp | $EC_{50}$ (mg/kg, s.c.) | SE | 95% CI lower | 95% CI upper |
|---|---|---|---|---|---|
| Progesterone | 1 | 5.50 | 0.77 | 4.21 | 7.20 |
| | 2 | 6.21 | 1.12 | 4.41 | 8.76 |
| 3-Ketodesogestrel | 1 | 0.11 | 0.02 | 0.07 | 0.16 |
| | 2 | 0.10 | 0.05 | 0.11 | 0.25 |
| | 3 | 0.06 | 0.03 | 0.03 | 0.14 |
| Levonorgestrel | 1 | 0.08 | 0.03 | 0.04 | 0.16 |
| | 2 | 0.12 | 0.02 | 0.09 | 0.17 |
| | 3 | 0.09 | 0.02 | 0.06 | 0.13 |
| | 4 | 0.09 | 0.02 | 0.06 | 0.14 |
| MPA | 1 | 0.42 | 0.03 | 0.29 | 0.60 |
| | 2 | 0.39 | 0.05 | 0.22 | 0.67 |
| | 3 | 0.39 | 0.04 | 0.25 | 0.61 |

TABLE 5

Estimated average $EC_{50}$, standard error, and 95% confidence intervals for dose-response curves of 3 reference compounds

| Compound | $EC_{50}$ (mg/kg, s.c.) | SE | 95% CI lower | 95% CI upper |
|---|---|---|---|---|
| Progesterone | 5.62 | 0.62 | 4.55 | 7.00 |
| 3-Ketodesogestrel | 0.10 | 0.02 | 0.07 | 0.14 |
| Levonorgestrel | 0.10 | 0.01 | 0.08 | 0.12 |

TABLE 6

Estimated $EC_{50}$, standard error, and 95% confident interval for the antiprogestin, RU 486

| Compound | Exp. | $IC_{50}$ (mg/kg, p.o.) | SE | 95% CI lower | 95% CI upper |
|---|---|---|---|---|---|
| RU 486 | 1 | 0.21 | 0.07 | 0.05 | 0.96 |
| | 2 | 0.14 | 0.02 | 0.08 | 0.27 |

Concentration: Compound concentration in assay (default-mg/kg body weight)

Route of administration: Route the compound is administered to the animals

Body weight: Mean total animal body weight (default-kg)

D-horn: Wet weight of decidualized uterine horn (default-mg)

C-horn: Wet weight of control uterine horn (default-mg)

Decidual response: $[(D-C)/C] \times 100\%$

Progestational activity: Compounds that induce decidualization significantly ($p<0.05$) compared to vehicle control are considered active Antiprogestational activity: Compounds that decrease $EC_{50}$ progesterone induced decidualization significantly ($p<0.05$)

$EC_{50}$ for uterine weight: Concentration of compound that gives half-maximal increase in decidual response (default-mg/kg)

$IC_{50}$ for uterine weight: Concentration of compound that gives half-maximal decrease in $EC_{50}$ progesterone induced decidual response (default-mg/kg)

(3) PRE-Luciferase Assay in CV-1 Cells

The object of this assay is to determine a compound's progestational or antiprogestational potency based on its effect on PRE-luciferase reporter activity in CV-1 cells co-transfected with human PR and PRE-luciferase plasmids. The materials methods used in the assay are as follows.

a. Medium: The growth medium was as follows: DMEM (BioWhittaker) containing 10% (v/v) fetal bovine serum (heat inactivated), 0.1 mM MEM non-essential amino acids, 100 U/ml penicillin, 100 mg/ml streptomycin, and 2 mM GlutaMax (GIBCO, BRL). The experimental medium was as follows: DMEM (BioWhittaker), phenol red-free, containing 10% (v/v) charcoal-stripped fetal bovine serum (heat-inactivated), 0.1 mM MEM non-essential amino acids, 100 U/ml penicillin, 100 mg/ml streptomycin, and 2 mM GlutaMax (GIBCO, BRL).

b. Cell Culture, Transfection, Treatment, and Luciferase Assay

Stock CV-1 cells are maintained in growth medium. Co-transfection is done using $1.2 \times 10^7$ cells, 5 mg pLEM plasmid with hPR-B inserted at SphI and BamHI sites, 10 mg pGL3 plasmid with two PREs upstream of the luciferase sequence, and 50 mg sonicated calf thymus DNA as carrier DNA in 250 ml. Electroporation is carried out at 260 V and 1,000 mF in a Biorad Gene Pulser II. After electroporation, cells are resuspended in growth medium and plated in 96-well plate at 40,000 cells/well in 200 µl. Following overnight incubation, the medium is changed to experimental medium. Cells are then treated with reference or test compounds in experimental medium. Compounds are tested for antiprogestational activity in the presence of 3 nM progesterone. Twenty-four hr. after treatment, the medium is discarded, cells are washed three times with D-PBS (GIBCO, BRL). Fifty µl of cell lysis buffer (Promega, Madison, Wis.) is added to each well and the plates are shaken for 15 min in a Titer Plate Shaker (Lab Line Instrument, Inc.). Luciferase activity is measured using luciferase reagents from Promega.

c. Analysis of Results:

Each treatment consists of at least 4 replicates. Log transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear response analyses.

d. Reference Compounds: Progesterone and trimegestone are reference progestins and RU486 is the reference antiprogestin. All reference compounds are run in full dose-response curves and the $EC_{50}$ or $IC_{50}$ values are calculated.

TABLE 8

Estimated $EC_{50}$, standard error (SE), and 95% confidence intervals (CI) for reference progestins from three individual studies

| Compound | Exp. | $EC_{50}$ (nM) | SE | 95% CI lower | 95% CI upper |
|---|---|---|---|---|---|
| Progesterone | 1 | 0.616 | 0.026 | 0.509 | 0.746 |
|  | 2 | 0.402 | 0.019 | 0.323 | 0.501 |
|  | 3 | 0.486 | 0.028 | 0.371 | 0.637 |
| Trimegestone | 1 | 0.0075 | 0.0002 | 0.0066 | 0.0085 |
|  | 2 | 0.0081 | 0.0003 | 0.0070 | 0.0094 |
|  | 3 | 0.0067 | 0.0003 | 0.0055 | 0.0082 |

TABLE 9

Estimated $IC_{50}$, standard error (SE), and 95% confident interval (CI) for the antiprogestin, RU486 from three individual studies

| Compound | Exp. | $IC_{50}$ (nM) | SE | 95% CI lower | 95% CI upper |
|---|---|---|---|---|---|
| RU486 | 1 | 0.028 | 0.002 | 0.019 | 0.042 |
|  | 2 | 0.037 | 0.002 | 0.029 | 0.048 |
|  | 3 | 0.019 | 0.001 | 0.013 | 0.027 |

Progestational activity: Compounds that increase PRE-luciferase activity significantly ($p<0.05$) compared to vehicle control are considered active. Antiprogestational activity: Compounds that decrease 3 nM progesterone induced PRE-luciferase activity significantly ($p<0.05$). $EC_{50}$: Concentration of a compound that gives half-maximal increase PRE-luciferase activity (default-nM) with SE.

$IC_{50}$: Concentration of a compound that gives half-maximal decrease in 3 nM progesterone induced PRE-luciferase activity (default-nM) with SE.

EXAMPLE 15

6-(3-fluorophenyl)-4-methyl-1,4-dihydro-2H-3,1-benzoxazine-2-thione

4-Amino-3'-fluoro[1,1'-biphenyl]-3-carbonitrile was prepared from 3-fluorophenyl boronic acid and 2-amino-5-bromobenzonitrile according to the procedure of Example 4. A solution of 4-amino-3'-fluoro[1,1'-biphenyl]-3-carbonitrile (6.65 g, 31.3 mmol) in anhydrous THF (100 mL) was treated drop wise at room temperature under nitrogen with methylmagnesium bromide (3.0 M in ether, 21 mL, 63 mmol). The reaction mixture was then heated at gentle reflux for 1.5 hours, cooled to room temperature, and treated with 3N aqueous hydrogen chloride solution (30 mL). The resulted mixture was heated at reflux for 3 hours, cooled to ambient temperature, and adjusted to a pH of 5-6 by the addition of a saturated aqueous sodium carbonate solution. Ethyl acetate (100 mL) was added, the organic layer was separated and the aqueous layer was extracted with ethyl acetate (3×50 mL). The combined organic layers were dried (MgSO₄) and evaporated. The residue was purified by a silica gel chromatography (hexane:ethyl acetate/3:1) to afford 1-(4-amino-3'-fluoro[1,1'-biphenyl]-3-yl)ethanone (3.1 g, 43%): mp 156-157° C.

A solution of 1-(4-amino-3'-fluoro[1,1'-biphenyl]-3-yl)ethanone (3 g, 13 mmol) in anhydrous methanol (60 mL) was then treated at room temperature under nitrogen with sodium borohydride in a portion wise manner. After addition, the reaction mixture was stirred for 4 hours, treated with a saturated solution of aqueous ammonium sulfate (50 mL) and ethyl acetate (100 mL). The organic layer was separated, dried (MgSO$_4$), and evaporated in vacuo. The residue was purified on a silica gel chromatography (hexane:ethyl acetate/ 3:1) to yield 1-(4-amino-3'-fluoro[1,1'-biphenyl]-3-yl)etha- nol as a white solid (2 g, 67%): mp 136-137° C.

A mixture of the above alcohol (0.2 g, 0.87 mmol) and triphosgene in anhydrous THF (20 mL) was stirred at room temperature under nitrogen. After 15 minutes, the mixture was treated with a saturated aqueous sodium bicarbonate solution (30 mL) and ethyl acetate (40 mL). The organic layer was separated, dried (MgSO$_4$), and evaporated to give 6-(3-fluorophenyl)-4-methyl-1,4-dihydro-2H-3,1-benzoxazin-2-one as a white solid (0.18 g, 81%): mp 160-161° C.; $^1$H-NMR (DMSO-d$_6$) δ 10.31 (s, 1H), 7.62 (dd, 1H, J=8.2, 1.9 Hz), 7.57 (s, 1H), 7.44-7.53 (m, 3H), 7.13-7.20 (m 1H), 6.97 (d, 1H, J=8.2 Hz), 5.57 (q, 1H, J=6.6 Hz), 1.63 (d, 3H, J=6.6 Hz). MS (ESI) m/z 256 [M−H]$^-$.

A solution of 6-(3-fluorophenyl)-4-methyl-1,4-dihydro-2H-3,1-benzoxazin-2-one (0.15 g, 0.58 mmol) in toluene was treated with Lawesson's reagent according to the procedure in example 9 to yield 6-(3-fluorophenyl)-4-methyl-1,4-dihydro-2H-3,1-benzoxazin-2-thione (0.08 g, 50%) as an off-white solid (0.08 g, 50%): mp 173-174° C.; $^1$H-NMR (DMSO-d$_6$) δ 12.27 (s, 1H), 7.70 (dd, 1H, J=8.2, 2.0 Hz), 7.62 (s, 1H), 7.46-7.56 (m, 3H), 7.15-7.22 (m, 1H), 7.11 (d, 1H, J=8.3 Hz), 5.64 (q, 1H, J=6.6 Hz), 1.67 (d, 3H, J=6.6 Hz); MS (ESI) m/z 272 [M−H]$^-$.

EXAMPLE 16

5-(4,4-Dimethyl-2-thioxo-1,4-dihydro-2H-3,1-benzoxazin-6-yl)-4-methylthiophene-2-carbonitrile 5-(4, 4-Dimethyl-2-oxo-1,4-dihydro-2H-benzo[d][1,3] oxazin-6-yl)-4-methyl-thiophene-2-carbonitrile was prepared, according to the procedure in Example 5 using (1,4-dihydro-4,4-dimethyl-2-oxo-2H-3,1-benzoxazin-6-yl) boronic acid and 5-bromo-4-methyl-2-thiophenecarbonitrile, as an off-white solid: mp 195-200° C.; $^1$H-NMR (DMSO-d$_6$) δ 10.2 (s, 1H), 8.32 (s, 1H), 7.41-7.44 (m, 2H), 7.01 (d, 1H, J=8.8 Hz), 2.28 (s, 3H), 1.64 (s, 6H); MS (APCI) m/z 299 [M+H]$^+$; Anal. Calcd. For C$_{16}$H$_{14}$N$_2$O$_2$S; C, 64.41; H, 4.75; N, 8.89. Found: C, 64.64; H, 4.62; N, 9.39.

To a solution of 5-(4,4-dimethyl-2-oxo-1,4-dihydro-2H-3, 1-benzoxazin-6-yl)-4-methylthiophene-2-carbonitrile (5 g, 16.7 mmol) in anhydrous toluene was added, at room temperature under a blanket of nitrogen, Lawesson's reagent (6 g, 14.8 mmol). The reaction mixture was heated at reflux for 2 hrs, allowed to cool to room temperature, and solvent was removed in vacuo. The residue was purified by a silica gel column chromatography (THF:hexane/1:3) to yield the title compound as a yellowish solid (2.4 g, 46%): mp 211-212° C.; $^1$H-NMR (DMSO-d$_6$) δ 12.3 (s, 1H), 7.88 (s, 1H), 7.46-7.52 (m, 2H), 7.16 (d, 1H, J=8.3 Hz), 2.30 (s, 3H), 1.68 (s, 6H); MS (ESI) m/z 313 [M−H]$^-$; Anal. Calcd. For C$_{16}$H$_{14}$N$_2$OS$_2$; C, 61.12; H, 4.49; N, 8.91. Found: C, 60.91; H, 4.48; N, 8.66.

EXAMPLE 17 tert-Butyl 2-cyano-5-(4,4-dimethyl-2-thioxo-1,4-dihydro-2H-3,1-benzoxazin-6-yl)-1H-pyrrole-1-carboxylate 2-(4,4-Dimethyl-2-oxo-1,4-dihydro-2H-benzo[d][1,3]oxazin-6-yl)-5-cyano-pyrrole-1-carboxylic acid tert-butyl ester (1 g, 2.7 mmol) was placed in a 25 mL round bottomed flask stoppered with a rubber septum and equipped with nitrogen inlet and a needle to allow gaseous outflow. A vigorous flow of nitrogen was maintained as the flask was placed in an oil bath and heated to 160° C. After 20 min at this temperature, the flask was removed from the oil bath and allowed to cool. The yellow residue was washed into a larger flask with dichloromethane/ethyl acetate and adsorbed onto a small amount of silica gel. Purification by flash column chromatography on silica gel (40% ethyl acetate/hexane) gave 5-(4,4-dimethyl-2-oxo-1,4-dihydro-2H-3,1-benzoxazin-6-yl)-1H-pyrrole-2-carbonitrile (340 mg, 47%) as a yellow powder: mp 241-242° C.; $^1$H NMR (d$_6$-DMSO, 300 MHz) δ 1.65 (s, 6H), 6.67 (d, 1H, J=3.9 Hz), 6.91 (d, 1H, J=8.3 Hz), 6.98 (d, 1H, J=3.9 Hz), 7.61 (dd, 1H, J=1.8, 8.3 Hz), 7.65 ('d', 1H, J=1.6 Hz), 10.32 (s, 1H), 12.54 (bs, 1H); MS (EI) m/z 267 M$^+$; Anal. Calcd. For C$_{15}$H$_{13}$N$_3$O$_2$: C, 67.41; H, 4.90; N, 15.72. Found: C, 67.19; H, 4.96; N, 15.35.

To a solution of 2-(4,4-dimethyl-2-oxo-1,4-dihydro-2H-benzo[d][1,3]oxazin-6-yl)-pyrrole-1-carboxylic acid tert-butyl ester (2.0 g, 5.8 mmol) in THF (anhydrous, 50 mL) at −78° C. was added chlorosulfonyl isocyanate (0.66 mL, 6.7 mmol). After 90 min, DMF (9 mL, 116 mmol) was added and the reaction was allowed to warm to room temperature. The reaction mixture was poured into water (50 mL) and the product was extracted with ethyl acetate (2×50 mL). The organic layers were combined, washed with brine (50 mL), dried over magnesium sulfate, filtered and concentrated in vacuo. Purification via flash column chromatography on silica gel (30% ethyl acetate/hexane) gave 2-(4,4-dimethyl-2-oxo-1,4-dihydro-2H-benzo[d][1,3]oxazin-6-yl)-5-cyano-pyrrole-1-carboxylic acid tert-butyl ester (1.1 g, 52%) as a white powder, mp 165-167° C.; $^1$H NMR (DMSO-d$_6$) δ 1.36 (s, 9H), 1.61 (s, 6H), 6.44 (d, 1H, J=3.7 Hz), 6.92 (d, 1H, J=8.2 Hz), 7.27-7.32 (m, 2H), 7.36 ('d', 1H, J=1.5 Hz), 10.36 (s, 1H); MS (EI) m/z 367 [M]$^+$.

To 2-(4,4-dimethyl-2-oxo-1,4-dihydro-2H-benzo[d][1,3] oxazin-6-yl)-5-cyano-pyrrole-1-carboxylic acid tert-butyl ester (1.3 g, 35 mmol, 1 eq) in toluene (130 mL) was added Lawesson's reagent (1.58 g, 3.9 mmol, 1.1 eq) and the reaction mixture was heated to 80° C. for 2 h. The solvent was removed in vacuo and the residue was dissolved in acetone/ dichloromethane and adsorbed onto silica gel. Purification by flash column chromatography (10% ethyl acetate/hexane) gave the product (0.51 g, 38%) as yellow crystals. $^1$H NMR (DMSO-d$_6$) δ 1.35 (s, 9H), 1.64 (s, 6H), 6.47 (d, 1H, J=3.6 Hz), 7.07 (d, 1H, J=8.1 Hz), 7.32 (d, 1H, J=3.6 Hz), 7.37 (dd, 1H, J=1.8, 8.1 Hz), 7.43 (d, 1H, J=1.8 Hz), 12.28 (s, 1H); MS (ESI) [M−H]$^-$=382; Anal. Calcd. For C$_{20}$H$_{21}$N$_3$O$_3$S: C, 62.64; H, 5.52; N, 10.96. Found: C, 62.53; H, 5.6; N, 10.87.

EXAMPLE 18

5-(4,4-Dimethyl-2-thioxo-1,4-dihydro-2H-3,1-benzoxazin-6-yl)-1H-pyrrole-2-carbonitrile To a solution of tert-butyl 2-cyano-5-(4,4-dimethyl-2-thioxo-1,4-dihydro-2H-3,1-benzoxazin-6-yl)-1H-pyrrole-1-carboxylate (0.5 g, 1.3 mmol, 1 eq) in THF (5 mL) was added NaOEt (0.27 g, 3.9 mmol, 3 eq) in EtOH (5 mL) and the reaction was heated to 80° C. for 2 h. The solvents were removed in vacuo and the residue partitioned between ethyl acetate (100 mL) and water (100 mL). The layers were separated and the aqueous layer was extracted with ethyl acetate (100 mL). The organic layers were combined, washed with brine (50 mL), dried over magnesium sulfate, filtered and concentrated in vacuo. Purification by flash column chromatography (10% ethyl acetate/hexane) gave the title compound (0.27 g, 73%) as a brown powder, mp 261-262° C. $^1$H NMR (DMSO-d$_6$) δ 1.68 (s, 6H), 6.72-6.73 (m, 1H), 6.99-7.01 (m, 1H), 7.06 (d, 1H, J=7.9 Hz), 7.66-7.70 (m, 2H), 12.26 (s, 1H), 12.62 (s, 1H); MS (ESI) [M−H]$^-$=282; Anal. Calcd. For C$_{15}$H$_{13}$N$_3$OS: C, 63.58; H, 4.62; N, 14.83. Found: C, 63.25; H, 4.78; N, 15.11.

EXAMPLE 19

[6-(4,4-dimethyl-2-thioxo-1,4-dihydro-2H-3,1-benzoxazin-6-yl)pyridin-2-yl]acetonitrile

[6-(4,4-dimethyl-2-oxo-1,4-dihydro-2H-3,1-benzoxazin-6-yl)pyridin-2-yl]acetonitrile was prepared, according to the procedure of Example 5 using (1,4-dihydro-4,4-dimethyl-2-oxo-2H-3,1-benzoxazin-6-yl)boronic acid and (6-bromo-2-pyridyl)acetonitrile (*J. Org. Chem.* 1988, 53, 786-790), as an off-white solid: mp 210-212.5° C.; $^1$H NMR (DMSO-d$_6$) δ 1.68 (s, 6H), 4.27 (s, 2H), 7.00 (d, 1H, J=8.3 Hz), 7.34 (d, 1H, J=7.1 Hz), 7.89-7.96 (m, 2H), 8.00-8.05 (m, 2H), 10.42 (s, 1H); MS (ESI) [M−H]$^-$=292; Anal. Calcd. For C$_{17}$H$_{15}$N$_3$O$_2$: C, 69.61; H, 5.15; N, 14.33. Found: C, 68.49; H, 5.19; N, 13.74.

To [6-(4,4-dimethyl-2-oxo-1,4-dihydro-2H-3,1-benzoxazin-6-yl)pyridin-2-yl]acetonitrile (80 mg, 0.27 mmol, 1 eq) in p-xylene (10 mL) was added Lawesson's reagent (55 mg, 0.14 mmol, 0.5 eq) and the reaction was heated to reflux for 2 hours. The reaction was cooled to room temperature and adsorbed onto silica gel. Purification by flash column chromatography (50% ethyl acetate/hexane) on silica gel gave the title compound (40 mg, 48%) as an off-white solid: mp 215-217° C.; $^1$H NMR (d$_6$-DMSO, 300 MHz) δ 1.71 (s, 6H), 4.28 (s, 2H), 7.15 (d, 1H, J=8.3 Hz), 7.36 (d, 1H, J=7.3 Hz), 7.89-7.99 (m, 2H), 8.04-8.11 (m, 2H), 12.32 (s, 1H); MS (ESI) [M−H]$^-$=308; Anal. Calcd. for C$_{17}$H$_{15}$N$_3$OS: C, 66.00; H, 4.89; N, 13.58. Found: C, 64.43; H, 4.65; N, 12.95.

EXAMPLE 20

5-(4,4-Dimethyl-2-thioxo-1,4-dihydro-2H-3,1-benzoxazin-6-yl-1-methyl-1H-pyrrole-2-carbonitrile 2-(4,4-Dimethyl-2-oxo-1,4-dihydro-2H-benzo[d][1,3]oxazin-6-yl)-5-cyano-pyrrole-1-carboxylic acid tert-butyl ester (1 g, 2.7 mmol) was placed in a 25 mL round bottomed flask stoppered with a rubber septum and equipped with nitrogen inlet and a needle to allow gaseous outflow. A vigorous flow of nitrogen was maintained as the flask was placed in an oil bath and heated to 160° C. After 20 min at this temperature, the flask was removed from the oil bath and allowed to cool. The yellow residue was washed into a larger flask with dichloromethane/ethyl acetate and adsorbed onto a small amount of silica gel. Purification by flash column chromatography on silica gel (40% ethyl acetate/hexane) gave of 5-(4,4-dimethyl-2-oxo-1,4-dihydro-2H-3,1-benzoxazin-6-yl)-1H-pyrrole-2-carbonitrile (340 mg, 47%) as a yellow powder: mp 241-242° C.; $^1$H NMR (d$_6$-DMSO, 300 MHz) δ 1.65 (s, 6H), 6.67 (d, 1H, J=3.9 Hz), 6.91 (d, 1H, J=8.3 Hz), 6.98 (d, 1H, J=3.9 Hz), 7.61 (dd, 1H, J=1.8, 8.3 Hz), 7.65 ('d', 1H, J=1.6 Hz), 10.32 (s, 1H), 12.54 (bs, 1H); MS (EI) m/z 267 M$^+$; Anal. Calcd. For C$_{15}$H$_{13}$N$_3$O$_2$: C, 67.41; H, 4.90; N, 15.72. Found: C, 67.19; H, 4.96; N, 15.35.

To a solution of 5-(4,4-dimethyl-2-oxo-1,4-dihydro-2H-3,1-benzoxazin-6-yl)-1H-pyrrole-2-carbonitrile (1 eq, 71 mg, 0.27 mmol) in dimethylformamide (0.5 mL) was added potassium carbonate (5 eq, 0.18 g, 0.1.35 mmol). After 10 min, iodomethane (3 eq, 0.05 mL, 0.81 mmol) was added and the suspension was stirred for 2 hours, poured into water (5 mL) and the product was extracted with ethyl acetate (3×5 mL). The layers were then separated, the aqueous layer extracted with ethyl acetate (3×10 mL) and the combined organic layer was washed with brine, dried over MgSO$_4$ and purified by flash column chromatography on silica gel eluting with 30% ethyl acetate/hexane to give 5-(4,4-dimethyl-2-oxo-1,4-dihydro-2H-3,1-benzoxazin-6-yl)-1-methyl-1H-pyrrole-2-carbonitrile (30 mg, 41%) as a white solid; MS (ES) m/z 280 (M−H)$^-$; Anal. Calcd. For C$_{16}$H$_{15}$N$_3$O$_2$: C, 68.3; H, 5.37; N, 14.9. Found, C, 68.4; H, 5.51; N, 14.6.

To a solution of 5-(4,4-dimethyl-2-oxo-1,4-dihydro-2H-3,1-benzoxazin-6-yl)-1-methyl-1H-pyrrole-2-carbonitrile (6.0 g, 22 mmol, 1 eq) in toluene (600 mL) was added Lawesson's reagent (5.9 g, 15 mmol, 0.65 eq) and the reaction was heated to 80° C. for 2 hours. The reaction was cooled to room temperature, poured into water (200 mL) and extracted with ethyl acetate (2×200 mL). The organic layers were combined, washed with brine (50 mL), dried over magnesium sulfate, filtered and concentrated in vacuo. Purification by flash column chromatography (5-10% ethyl acetate/hexane) gave the title compound (2.0 g, 31%) as a slightly yellow solid: mp 225-228° C. $^1$H NMR (d$_6$-DMSO, 300 MHz) δ 1.67 (s, 6H), 3.72 (s, 3H), 6.37 (dd, 1H, J=0.8, 4.1 Hz), 7.04 (dd, 1H, J=0.8, 4.1 Hz), 7.13 (m, 1H), 7.47 (m, 2H), 12.30 (s, 1H); MS (ESI) [M−H]$^-$=296; Anal. Calcd. for C$_{16}$H$_{15}$N$_3$OS: C, 64.62; H, 5.08; N, 14.13. Found: C, 64.7; H, 5.12; N, 14.17.

EXAMPLE 21

5-(4,4-dimethyl-2-thioxo-1,4-dihydro-2H-3,1-benzoxazin-6-yl)-1H-pyrrole-2-carbothiamide To 4,4-dimethyl-6-(5-cyano-1H-pyrrol-2-yl)-1,4-dihydrobenzo[d][1,3]oxazin-2-one (6.0 g, 22.5 mmol) in p-xylene (100 mL) was added Lawesson's reagent (5.9 g, 14.6 mmol, 0.65 eq) and the reaction was heated to reflux for 3 hours. The reaction was cooled to room temperature, concentrated in vacuo, and adsorbed onto silica gel. Purification by flash column chromatography (30% ethyl acetate/hexane) on silica gel gave the title compound (1.2 g, 17%) as a yellow powder: $^1$H NMR (DMSO-d$_6$) δ 1.69 (s, 6H), 6.65 (dd, 1H, J=2.2, 3.8 Hz), 6.98 (dd, 1H, J=2.2, 3.8 Hz), 7.03 (d, 1H, J=8.2 Hz), 7.69 (dd, 1H, J=1.6, 8.2 Hz), 7.81 (d, 1H, J=1.6 Hz), 8.92 (s, 1H), 9.09 (s, 1H), 11.19 (s, 1H), 12.22 (s, 1H); MS (ESI) [M+H]$^+$= 318, [M−H]$^-$=316; Anal. Calcd. for C$_{15}$H$_{15}$N$_3$OS$_2$: C, 56.76; H, 4.76; N, 13.24. Found: C, 56.78; H, 4.87; N, 12.54.

EXAMPLE 22

5-(4,4-Dimethyl-2-thioxo-1,4-dihydro-2H-benzo[d][1,3]oxazin-6-yl) thiophene-3-carbonitrile 5-(4,4-Dimethyl-2-oxo-1,4-dihydro-2H-benzo[d][1,3]oxazin-6-yl)-thiophene-3-carbonitrile was prepared, according to the procedure in Example 5 using (1,4-dihydro-4,4-dimethyl-2-oxo-2H-3,1-benzoxin-6-yl)boronic acid and 2-bromo-4-thiophenecarbonitrile, as an off-white solid: mp 255-260° C.; $^1$H-NMR (DMSO-d$_6$) δ 10.36 (s, 1H), 8.48 (d, 1H, J=1.1 Hz),7.88-7.87 (d, 1H J=1.3 Hz), 7.63 (d, 1H J=1.9 Hz), 7.56-7.54 (dd, 1H, J=8.0, 2.0 Hz), 6.93 (d, 1H, J=8.1 Hz),1.64 (s, 6H); MS (-ESI) m/z 283 (M−H)$^-$.

The title compound was prepared in a manner similar to Example 16 using 5-(4,4-dimethyl-2-oxo-1,4-dihydro-2H-benzo[d][1,3]oxazin-6-yl) thiophene-3-carbonitrile and Lawesson's reagent. The product was obtained in the form of yellow crystals: m.p. 258-259° C. $^1$H NMR (DMSO-d$_6$) δ 12.3 (s, 1H), 8.54 (d, 1H, J=0.9 Hz), 7.96 (s, 1H), 7.69-7.62 (m, 2H), 7.11-7.08 (d, 1H, J=8.3 Hz), 1.69 (s, 6H); MS (ESI) m/z 299 [M−H]$^-$; Anal. Calcd. For C$_{15}$H$_{12}$N$_2$OS$_2$·½ H$_2$O: C, 58.0; H, 4.24; N, 9.05. Found: C, 58.33; H, 3.85; N, 8.39.

EXAMPLE 23

5-(4,4-dimethyl-2-thioxo-1,4-dihydro-2H-3,1-benzoxazin-6-yl)-1-ethyl-1H-pyrrole-2-carbonitrile To a solution of 5-(4,4-dimethyl-2-oxo-1,4-dihydro-2H-3,1-benzoxazin-6-yl)-1H-pyrrole-2-carbonitrile (1.3 g, 5 mmol) in dimethylformamide (25 ml) was added potassium carbonate (1 g, 7.5 mmol), and iodomethane (0.4 ml, 5.1 mmol), and the mixture was stirred at room temperature for 3 hours. The mixture was triturated with ethyl acetate/water, and the ethyl acetate layer was separated, dried over magnesium sulfate, and concentrated in vacuo. The residue was recrystallized from ethyl acetate/hexane to afford 5-(4,4-dimethyl-2-oxo-1,4-dihydro-2H-3,1-benzoxazin-6-yl)-1-ethyl-1H-pyrrole-2-carbonitrile (0.4 g, 27%): m.p. 200-202° C.; $^1$H-NMR (DMSO-$d_6$) δ 1.25 (t, J=7.2 Hz, 3H), 1.64 (s, 6H), 4.07 (q, J=7.2 Hz, 2H), 6.29 (d, J=4.1 Hz, 1H), 7.0 (d, J=8 Hz, 1H), 7.05 (d, J=4.1 Hz, 1H), 7.34 (m, 2H), 10.42 (s, 1H); MS (ESI) m/z 2 94 (M−H)$^-$.

The title compound was prepared according to the procedure for Example 16 from 5-(4,4-dimethyl-2-oxo-1,4-dihydro-2H-3,1-benzoxazin-6-yl)-1-ethyl-1H-pyrrole-2-carbonitrile and Lawesson's reagent. The product was obtained in the form of white needles: mp 212-213° C.; $^1$H-NMR (DMSO-$d_6$) δ 1.25 (t, 3H, J=7 Hz), 1.68 (s, 6H), 4.07 (q, J=7 Hz, 2H), 6.32 (d, J=3.9 Hz, 1H), 7.07 (d, J=3.9 Hz, 1H), 7.15 (d, J=9 Hz, 1H), 7.42 (m, 2H), 12.33 (s, 1H); MS (ESI) m/z 310 (M−H)$^-$.

EXAMPLE 24

4-(1,2-Dihydro-2-thioxospiro[4H-3,1-benzoxazin-4,1-cyclohexan]-6-yl)-2-thiophenecarbonitrile 1-(2-Amino-5-bromo-phenyl)cyclohexanol was prepared, according to the procedure of Example 1 using 2-amino-5-bromobenzoic acid and the Grignard reagent prepared from 1,5-dibromopentane, as a clear oil: $^1$H-NMR (DMSO-$d_6$) δ 7.07 (d, 1H, J=2.3 Hz), 7.03 (dd, 1H, J=8.4, 2.4 Hz), 6.55 (d, 1H, J=8.6 Hz), 5.49 (s, 2H, D$_2$O exchangeable), 5.00 (s, 1H, D$_2$O exchangeable), 2.01 (d, 2H, J=1.8 Hz), 1.66-1.77 (m, 2H), 1.44-1.61 (m, 4H), 1.16-1.34 (m, 2H); MS (ESI) m/z 270/272 ([M+H]$^+$, 98%/100%).

6-Bromo-spiro[4H-3,1-benzoxazine-4,1'-cyclohexane-2-(1H)-one] was prepared from 1-(2-amino-5-bromo-phenyl)cyclohexanol and carbonyl diimidazole according to the procedure of Example 2. The product was obtained as an off-white solid: mp 208-210° C.; $^1$H-NMR (DMSO-$d_6$) δ 10.26 (s, 1H), 7.45 (d, 1H, J=2.2 Hz), 7.39 (dd, 1H, J=8.2, 2.2 Hz), 6.81 (d, 1H, J=8.3 Hz), 1.90-1.97 (m, 2H), 1.80-1.85 (m, 5H), 1.25-1.35 (m, 1H); MS (APC1) m/z 296 ([M+H]$^+$, 68%).

Spiro-(4,1'-cyclohexane-1,4-dihydro-2-oxo-2H-3,1-benzoxazin-6-yl)boronic acid, prepared according to the procedure of Example 4 using 6-bromo-spiro[4H-3,1-benzoxazine-4,1'-cyclohexane]-2-(1H)-one, as an off-white solid: mp 223-225° C. $^1$H-NMR (DMSO-$d_6$) δ 10.17 (s, 1H, D$_2$O exchangeable), 7.92 (s, 2H, D$_2$O exchangeable), 7.67 (s, 1H), 7.63 (dd, 1H, J=8.0, 1.1 Hz), 6.81 (d, 1H, J=7.9 Hz), 1.96 (s, 1H), 1.93 (s, 1H), 1.57-1.88 (m, 7H), 1.24-1.34 (m, 1H); MS (ESI) m/z 262 (M+H)$^+$.

4-(1,2-Dihydro-2-oxospiro[4H-3,1-benzoxazine-4,1-cyclohexan]-6-yl)-2-thiophenecarbonitrile was prepared, according to the procedure of Example 5 from spiro-(4,1'-cyclohexane-1,4-dihydro-2-oxo-2H-3,1-benzoxazin-6-yl)boronic acid and 3-bromo-5-cyanothiophene, as white crystals: mp 230-232° C.; IR (KBr) 2200 cm$^{-1}$; $^1$H-NMR (DMSO-$d_6$) δ 10.29 (s, 1H), 8.49 (s, 1H), 8.33 (s, 1H), 7.69-7.63 (m, 2H), 6.93-6.91 (d, 1H, J=8.2 Hz), 1.99-1.87 (m, 4H), 1.73-1.64 (m, 5H), 1.38-1.31 (m, 1H); MS (+)APCI m/z 325 (M+H)$^+$; Anal. Calc. For C$_{18}$H$_{16}$N$_2$O$_2$S¼H$_2$O: C, 65.73; H, 5.06; N, 8.52. Found C, 65.55; H, 5.06; N, 8.22.

The title compound was prepared, according to the procedure of Example 16 using 4-(1,2-dihydro-2-oxospiro[4H-3,1-benzoxazine-4,1-cyclohexan]-6-yl)-2-thiophenecarbonitrile, as a yellow solid: mp 225-227° C.; $^1$H-NMR (CDCl$_3$) δ 8.98 (s, 1H), 7.83 (d, 1H, J=1.47 Hz), 7.63 (d, 1H, J=1.47 Hz), 7.46 (dd, 1H, J=8.2, 1.91 Hz), 7.32 (m, 1H), 6.86 (d, 1H, J=8.19 Hz), 2.28-2.29 (m, 2H), 2.06-2.01 (m, 2H), 1.83-1.70 (m, 5H), 1.37-1.3 (m, 1H); MS (ES) m/z 339 ([M−H]$^-$).

EXAMPLE 25

5-(4,4-Dimethyl-2-thioxo-1,4-dihydro-2H-3,1-benzoxaz-6-yl)-2-fluorobenzonitrile 3-(4,4-Dimethyl-2-oxo-1,4-dihydro-2H-benzo[d][1,3]oxazin-6-yl)-4-fluoro-benzonitrile was prepared, from (1,4-dihydro-4,4-dimethyl-2-oxo-2H-3,1-benzoxin-6-yl)boronic acid and 5-bromo-2-fluorobenzonitrile according to the procedure of Example 5, as a white solid: mp 229-230° C.; $^1$H-NMR (DMSO-$d_6$) δ 10.4 (s, 1H), 8.15 (dd, 1H, J=7.39, 2.12 Hz), 7.95-7.89 (m, 1H), 7.59-7.48 (m, 3H), 6.99 (d, 1H, J=8.1 Hz), 1.7 (s, 6H); MS (APCI) m/z 297 ([M+H]$^+$, 100%); Anal. Calcd. For C$_{17}$H$_{13}$FN$_2$O$_2$: C, 68.91; H, 4.42; N, 9.45. Found: C, 68.74; H, 4.83; N, 9.10.

The title compound was prepared, according to the procedure of Example 16 using 5-(4,4-dimethyl-2-oxo-1,4-dihydro-2H-benzo[d][1,3]oxazin-6-yl)-2-fluoro-benzonitrile, as a white solid: mp 258-259° C.; $^1$H-NMR (DMSO-$d_6$) δ 12.3 (s, 1H), 8.35-8.32 (m, 1H), 8.15-8.10 (m, 1H), 7.72-7.7 (m, 2H), 7.66-7.60 (m, 1H), 7.13 (d, 1H, J=8.07 Hz), 1.7 (s, 6H); LC/MS (ES) m/z 311 ([M+H]$^+$, 100%); Anal. Calcd. For C$_{17}$H$_{13}$FN$_2$OS: C, 64.99; H, 4.24; N, 8.66. Found: C, 64.7; H, 4.09; N, 8.66.

EXAMPLE 26

6-(5-Bromopyridin-3-yl)-4,4-dimethyl-1,4-dihydro-2H-3,1-benzoxazine-2-thione 6-(5-Bromo-pyridin-3-yl)-4,4-dimethyl-1,4-dihydro-benzo[d][1,3]oxazin-2-one, prepared from (1,4-dihydro-4,4-dimethyl-2-oxo-2H-3,1-benzoxazin-6-yl)boronic acid and 3,5-dibromopyridine according to the procedure of Example 6, as a white solid: mp 211-212° C.; $^1$H-NMR (DMSO-$d_6$) δ 10.4 (s, 1H), 8.92 (d, 1H, J=1.9 Hz), 8.66 (d, 1H, J=2.09 Hz), 8.40 (t, 1H, J=2.02 Hz), 7.72-7.68 (m, 2H), 6.99 (d, 1H, J=8.1 Hz), 1.7 (s, 6H); MS (APCI) m/z 333 ([M+H]$^+$, 100%), 335 ([M+H]$^+$, 100%); Anal. Calcd. For C$_{15}$H$_{13}$BrN$_2$O$_2$: C, 54.07; H, 3.93; N, 8.41. Found: C, 54.15; H, 3.89; N, 8.31.

The title compound was prepared, according to the procedure of Example 16 using 6-(5-bromo-pyridin-3-yl)-4,4-dimethyl-1,4-dihydro-benzo[d][1,3]oxazin-2-one, as a white solid: mp 252-253° C.; $^1$H-NMR (DMSO-$d_6$) δ 12.3 (s, 1H), 8.94 (s, 1H), 8.69 (s, 1H), 8.44 (s, 1H), 7.78-7.76 (m, 2H), 7.14 (d, 1H, J=8.8 Hz), 1.7 (s, 6H); LC/MS (ES) m/z 347/349 ([M−H]$^-$); Anal. Calcd. For C$_{15}$H$_{13}$BrN$_2$OS: C, 51.32; H, 3.79; N, 7.98. Found: C, 50.95; H, 3.56; N, 7.72.

EXAMPLE 27

6-(3-Chloro-5-fluorophenyl)-4,4-dimethyl-1,4-dihydro-2H-3,1-benzoxazine-2-thione 6-(3-Chloro-5-fluoro-phenyl)-4,4-dimethyl-1,4-dihydro-benzo[d][1,3]oxazin-2-one was prepared, from (1,4-dihydro-4,4-dimethyl-2-oxo-2H-3,1-benzoxin-6-yl)boronic acid and 1-bromo-3-chloro-5-fluorobenzene according to the procedure of Example 5, as a white solid: mp 193-194° C.; $^1$H-NMR (DMSO-$d_6$) δ 10.4 (s, 1H), 7.67-7.64 (m, 3H), 7.61-7.57 (m, 1H), 7.41-7.37 (m, 1H), 6.96 (d, 1H, J=8.72 Hz), 1.7 (s, 6H); MS (APCI) m/z 306 ([M+H]$^+$, 100%); Anal. Calcd. For C$_{16}$H$_{13}$ClFNO$_2$: C, 62.86; H, 4.29; N, 4.58. Found: C, 62.98; H, 4.1; N, 4.6.

The title compound was prepared, according to the procedure of Example 16, starting with 6-(3-chloro-5-fluoro-phenyl)-4,4-dimethyl-1,4-dihydro-benzo[d][1,3]oxazin-2-one: mp 204-205° C.; $^1$H-NMR (CDCl$_3$) δ 10.0 (s, 1H), 7.49 (m, 1H), 7.31 (bs, 2H), 7.15-7.08 (m, 2H), 7.01 (d, 1H, J=8.23 Hz), 1.9 (s, 6H); LC/MS (ES) m/z 320/322 ([M−H]$^−$).

EXAMPLE 28

6-(3-Bromo-5-methylphenyl)-4,4-dimethyl-1,4-dihydro-2H-3,1-benzoxazine-2-thione 6-(3-Bromo-5-methyl-phenyl)-4,4-dimethyl-1,4-dihydrobenzo-[d][1,3]oxazin-2-one was prepared, using (4,4-dimethyl-1,4-dihydro-2-oxo-2H-3,1-benzoxazin-6-yl)boronic acid and 3,5-dibromotoluene according to the procedure of Example 5, as a white solid: mp 231-233° C.; $^1$H-NMR (DMSO-d$_6$) δ 10.4 (s, 1H), 7.66 (s, 1H), 7.58-7.56 (m, 2H), 7.50 (s, 1H), 7.37 (s, 1H), 6.95 (d, 1H, J=8.67 Hz), 2.37 (s, 3H), 1.67 (s, 6H); MS (ESI) m/z 344/346 ([M−H]$^−$, 100%); Anal. Calcd. For C$_{17}$H$_{16}$BrNO$_2$: C, 58.98; H, 4.66; N, 4.05. Found: C, 58.82; H, 4.62; N, 3.94.

The title compound was prepared according to the procedure of Example 16, using 6-(3-Bromo-5-methyl-phenyl)-4,4-dimethyl-1,4-dihydro-benzo[d][1,3]oxazin-2-one, as a yellow solid: mp 183-184° C.; $^1$H-NMR (CDCl$_3$) δ 9.8 (s, 1H), 7.48-7.46 (m, 2H), 7.34-7.25 (m, 4H), 6.97 (d, 1H, J=8.2 Hz), 2.4 (s, 3H), 1.8 (s, 6H); MS (ES) m/z 360/362 ([M−H]$^−$).

EXAMPLE 29

6-(3-Bromo-5-trifluoromethoxyphenyl)-4,4-dimethyl-1,4-dihydro-2H-3,1-benzoxazine-2-thione 6-(3-Bromo-5-trifluoromethoxy-phenyl)-4,4-dimethyl-1,4-dihydrobenzo[d][1,3]-oxazin-2-one was prepared, using (4,4-dimethyl-1,4-dihydro-2-oxo-2H-3,1-benzoxazin-6-yl) boronic acid and 1,3-dibromo-5-trifluoromethoxybenzene according to the procedure of Example 5, as a white solid: mp 214-216° C.; $^1$H-NMR (DMSO-d$_6$) δ 10.4 (s, 1H), 7.99 (s, 1H), 7.73 (s, 1H), 7.68-7.62 (m, 3H), 6.97 (d, 1H, J=8.0 Hz), 1.68 (s, 6H); MS (ESI) m/z 414 ([M−H]$^−$, 100%); Anal. Calcd. For C$_{17}$H$_{13}$BrF$_3$NO$_3$: C, 49.06; H, 3.15; N, 3.37. Found: C, 49.16; H, 3.05; N, 3.30.

The title compound was prepared, according to the procedure of Example 16 starting with 6-(3-Bromo-5-trifluoromethoxy-phenyl)-4,4-dimethyl-1,4-dihydro-benzo[d][1,3]oxazin-2-one, as a yellow solid: mp 192-193° C.; $^1$H-NMR (CDCl$_3$) δ 9.4 (s, 1H), 7.61 (s, 1H), 7.49-7.46 (m, 1H), 7.40 (s, 1H), 7.30 (s, 2H), 6.96 (d, 1H, J=8.22 Hz) 1.9 (s, 6H); MS (ES) m/z 431/433 ([M−H]$^−$).

EXAMPLE 30

3-(1,2-Dihydro-2-thioxospiro[4H-3,1-benzoxazine-4,1-cyclohexan]-6-yl)-5-fluorobenzonitrile 3-(1,2-Dihydro-2-oxospiro[4H-3,1-benzoxazine-4,1-cyclohexan]-6-yl)-5-fluorobenzonitrile was prepared, according to the procedure of Example 5 from spiro-(4,1'-cyclohexane-1,4-dihydro-2-oxo-2H-3,1-benzoxazin-6-yl) boronic acid and 3-bromo-5-fluorobenzonitrile, as a white powder: mp 250-253° C.; IR (KBr) 2220 cm$^{−1}$; $^1$H-NMR (DMSO-d$_6$) δ 10.34 (s, 1H), 8.13 (s, 1H), 8.0 (d, 1H, J=10.6 Hz), 7.80-7.7 (m, 3H), 6.98-6.95 (d, 1H, J=8.1 Hz), 1.99-1.97 (m, 4H), 1.76-1.65 (m, 6H), 1.37-1.33 (m. 1H). MS (EI) m/z 336 (M$^+$); Anal. Calcd. For C$_{20}$H$_{17}$FN$_2$O$_2$.H$_2$O: C, 67.78; H, 5.40; N, 7.90. Found: C, 67.9; H, 4.93; N, 7.67.

The title compound was prepared according to the procedure of Example 16 using 3-(1,2-Dihydro-2-oxospiro[4H-3,1-benzoxazine-4,1-cyclohexan]-6-yl)-5-fluorobenzonitrile: mp 235-237° C.; $^1$H-NMR (CDCl$_3$) δ 10.0 (s, 1H), 7.76-7.69 (m, 2H), 7.50-7.33 (m, 3H), 7.03 (d, 1H, J=8.8 Hz), 2.3-1.26 (m, 10H); MS (ES) m/z 351 ([M−H]$^−$).

EXAMPLE 31

3-(4,4-Dimethyl-2-thioxo-1,4-dihydro-2H-3,1-benzoxazin-6-yl)-5-methylbenzonitrile 3-(4,4-Dimethyl-2-oxo-1,4-dihydro-2H-benzo[d][1,3]oxazin-6-yl)-5-methyl-benzonitrile was prepared, from 4,4-dimethyl-1,4-dihydro-2-oxo-2H-3,1-benzoxazin-6-yl)boronic acid and 3-bromo-5-methylbenzonitrile according to the procedure of Example 5, as a white solid: mp 256-258° C.; $^1$H-NMR (DMSO-d$_6$) δ 10.4 (s, 1H), 7.99 (s, 1H), 7.86 (s, 1H), 7.67-7.62 (m, 3H), 6.97 (d, 1H, J=8.11 Hz), 2.42 (s, 3H), 1.68 (s, 6H); MS (APCI) m/z 293 ([M+H]$^+$, 100%); Anal. Calcd. For C$_{18}$H$_{16}$N$_2$O$_2$: C, 73.96; H, 5.52; N, 9.58. Found: C, 73.26; H, 5.46; N, 9.24.

The title compound was prepared, according to the procedure for Example 16 starting with 6-(3-cyano-5-methyl-phenyl)-4,4-dimethyl-1,4-dihydro-benzo[d][1,3]oxazin-2-one: mp 230-231° C.; $^1$H-NMR (CDCl$_3$) δ 9.1 (s, 1H), 7.61 (s, 1H), 7.55 (s, 1H), 7.50-7.47 (m, 2H), 7.32-7.31 (m, 1H), 6.91 (d, 1H, J=8.2 Hz), 2.5 (s, 3H), 1.8 (s, 6H); MS (ES) m/z 307 ([M−H]$^−$).

EXAMPLE 32

6-(3,5-Dichlorophenyl)-4,4-dimethyl-1,4-dihydro-2H-3,1-benzoxazine-2-thione 6-(3,5-dichloro-phenyl)-4,4-dimethyl-1,4-dihydrobenzo-[d][1,3]oxazin-2-one was prepared, from 6-bromo-4,4-dimethyl-1,4-dihydro-benzo[d][1,3]oxazin-2-one and 3,5-dichlorophenyl boronic acid according to the procedure of Example 4, as a white solid: mp 245-246° C.; $^1$H-NMR (DMSO-d$_6$) δ 10.4 (s, 1H), 7.77 (m, 2H), 7.67-7.64 (m, 2H), 7.56 (bs, 1H), 6.96 (d, 1H, J=7.98 Hz), 1.7 (s, 6H); MS (EI) m/z 321 ([M+H]$^+$, 40%); Anal. Calcd. For C$_{16}$H$_{13}$Cl$_2$NO$_2$: C, 59.32; H, 4.11; N, 4.32. Found: C, 59.13; H, 4.29; N, 4.17.

The title compound was prepared, according to the procedure of Example 16 starting with 6-(3,5-Dichloro-phenyl)-4,4-dimethyl-1,4-dihydro-benzo[d][1,3]oxazin-2-one: mp 206-208° C.; $^1$H-NMR (CDCl$_3$) δ 9.5 (s, 1H), 7.49-7.45 (m, 1H), 7.40-7.36 (m, 3H), 7.3-7.29 (m, 1H), 6.95 (d, 1H, J=8.23 Hz), 1.8 (s, 6H); MS (ES) m/z 336/338 ([M−H]$^−$).

EXAMPLE 33

5-(4,4-Dimethyl-1,2-thioxo-1,4-dihydro-2H-3,1-benzoxazin-6-yl)isophthalonitrile 5-(4,4-Dimethyl-2-oxo-1,4-dihydro-2H-benzo[d][1,3]oxazin-6-yl)-isophthalonitrile was prepared from (1,4-dihydro-4,4-dimethyl-2-oxo-2H-3,1-benzoxin-6-yl)boronic acid and 5-bromoisophthalonitrile according to the procedure Example 5, as a white solid: mp 288-289° C.; $^1$H-NMR (DMSO-d$_6$) δ 10.4 (s, 1H), 8.58 (s, 2H), 8.40 (d, 1H, J=0.77 Hz), 7.80-7.75 (m, 2H), 6.99 (d, 1H, J=8.2 Hz), 1.7 (s, 6H); MS (EI) m/z 303 ([M$^+$], 20%); Anal. Calcd. For C$_{18}$H$_{13}$N$_3$O$_2$.1.65 H$_2$O: C, 64.92; H, 4.93; N, 12.62. Found: C, 64.74; H, 4.69; N, 12.32.

The title compound was prepared according to the procedure of Example 16 starting with 5-(4,4-Dimethyl-2-oxo-1,4-dihydro-2H-benzo[d][1,3]oxazin-6-yl)-isophthalonitrile: mp 240-242° C.; $^1$H-NMR (CDCl$_3$) δ 9.4 (s, 1H), 8.03 (d, 2H, J=1.25 Hz), 7.92 (s, 1H), 7.50 (dd, 1H, J=8.22, 1.89 Hz), 7.33 (d, 1H, J=1.8 Hz), 7.01 (d, 1H, J=8.24 Hz), 1.84 (s, 6H); MS (ES) m/z 318 ([M−H]$^−$).

EXAMPLE 34

5-(4,4-Dimethyl-2-thioxo-1,4-dihydro-2H-3,1-benzoxazin-6-yl)-2-furonitrile 5-(4,4-Dimethyl-2-oxo-1,4-dihydro-2H-benzo[d][1,3]oxazin-6-yl)-furan-2-carbonitrile was prepared, according to the procedure of Example 5 from 2-bromo-5-cyanofuran (1.0 g, 5.6 mmol) (J. Med. Chem. (1997), 40(23), 3804-3819) and (1,4-dihydro-4,4-dimethyl-2-oxo-2H-3,1-benzoxazin-6-yl) boronic acid (1.8 g, 8.18 mmol), as a white solid (0.39 g, 1.45 mmol, 17%): mp 257-260° C.; $^1$H-NMR (DMSO-$d_6$) δ 10.48 (s, 1H), 7.73-7.70 (m, 3H), 7.19 (d, 1H, J=3.8 Hz), 6.98 (d, 1H, J=8.9 Hz), 1.66 (s, 6H); MS ((+)-APCI) m/z=269 (M+H)$^+$.

The title compound was prepared according to the procedure of Example 16 using 5-(1,4-Dihydro-4,4-dimethyl-2-oxo-2H-3,1-benzoxazin-6-yl)-2-furancarbonitrile: mp 200° C. decomposes; $^1$H-NMR (CDCl$_3$) δ 9.1 (s, 1H), 7.63 (dd, 1H, J=8.26, 1.68 Hz), 7.53 (d, 1H, J=1.59 Hz), 7.19 (d, 1H, J=3.7 Hz), 6.89 (d, 1H, J=8.31 Hz), 6.71 (d, 1H, J=3.72 Hz), 1.8 (s, 6H); MS (ES) m/z 283 ([M−H]$^-$)

EXAMPLE 35

4,4-Diethyl-6-(3-nitrophenyl)-1,4-dihydro-2H-3,1-benzoxazine-2-thione 4,4-Diethyl-6-(3-nitrophenyl)-1,4-dihydrobenzo[d][1,3]oxazin-2-one was prepared, from 4,4-diethyl-6-iodo-1,4-dihydrobenzo[d][1,3]oxazin-2-one and 3-nitrophenyl boronic acid according to the procedure of Example 4, as an off-white solid: mp 193-194° C.; $^1$H-NMR (CDCl$_3$) δ 9.19 (s, 1H, D$_2$O exchangeable), 8.38 (t, 1H, J=1.9 Hz), 8.20 (m, 1H), 7.83 (m, 1H), 7.61 (t, 1H, J=8.0 Hz), 7.50 (dd, 1H, J=8.2, 2.0 Hz), 7.23 (d, 1H, J=1.7 Hz), 6.99 (d, 1H, J=8.3 Hz), 2.09 (q, 4H, J=7.4 Hz), 0.96 (t, 6H, J=8.3 Hz); MS (EI) m/z 325 ([M−H]$^-$, 100%). Anal. Calcd. For C$_{18}$H$_{18}$N$_2$O$_4$.0.3 H$_2$O: C, 65.17; H, 5.65; N, 8.44. Found: C, 65.31; H, 5.60; N, 8.10.

The title compound was prepared, according to the procedure of Example 16 starting with 4,4-Diethyl-6-(3-nitro-phenyl)-1,4-dihydro-benzo[d][1,3]oxazin-2-one, as a yellow solid: mp 180-181° C.; $^1$H-NMR (CDCl$_3$) δ 9.1 (s, 1H), 8.38 (t, 1H, J=1.94 Hz), 8.25-8.22 (m, 1H), 7.87-7.85 (m, 1H), 7.64 (t, 1H, J=7.99 Hz), 7.55 (dd, 1H, J=8.24, 1.89 Hz), 7.25 (d, 1H, J=1.71 Hz), 6.93 (d, 1H, J=8.25 Hz), 2.2-2.03 (m, 4H), 0.96 (t, 6H, J=7.33 Hz); MS (ES) m/z 341 ([M−H]$^-$).

EXAMPLE 36

6-(3-Chlorophenyl)-4-methyl-4-phenyl-1,4-dihydro-2H-3,1-benzoxazine-2-thione A mixture of 2-amino-5-bromo-N-methoxy-N-methyl-benzamide (7.78 g, 30 mmol), 3-chlorophenyl boronic acid (5.63 g, 36 mmol), tetrakis(triphenylphosphine)palladium (0) (1.73 g, 1.5 mmol), and sodium carbonate (7.63 g, 72 mmol) in a mixture of DME and water (150 mL/30 mL) was degassed to remove the oxygen and heated at 85° C. under nitrogen for 3 hours. The reaction mixture was cooled to room temperature and treated with brine (30 mL) and ethyl acetate (100 mL). The organic layer was separated and the aqueous layer was extracted with ethyl acetate (3×40 mL). The combined organic layers were washed with brine and dried with MgSO$_4$. After removal of the solvent, the residue was purified by a flash chromatography (silica gel, hexane:ethyl acetate/1:1) to give 5-(3-chlorophenyl)-N-methoxy-N-methylbenzamide as a brown oil (5 g, 57%). To a solution of this benzamide (5 g, 17.2 mmol) in anhydrous THF was added in a dropwise fashion a solution of methyllithium in ether (1.4M, 28.6 mL, 40 mL) at −78° C. under nitrogen. After stirring for 30 minutes, the reaction mixture was treated with a saturated aqueous ammonium chloride solution (50 mL) at −78° C. Ethyl acetate (100 mL) was added, organic layer was separated, and aqueous layer was extracted with ethyl acetate (3×20 mL). The combined organic layers were washed (brine) and dried (MgSO$_4$). After removal of the solvent, the residue was purified by a flash chromatography (silica gel, hexane:ethyl acetate/2:1) to afford 1-(4-amino-3'-chloro-biphenyl-3-yl)-ethanone as a yellow solid (2 g, 47%): mp 89-90° C.; $^1$H-NMR (CDCl$_3$) δ 7.89 (d, 1H, J=2.0 Hz), 7.51 (m, 2H), 7.25-7.40 (m, 3H), 6.73 (d, 1H, J=8.6 Hz), 6.38 (br, 2H), 2.65 (s, 3H); MS (EI) m/z 268 ([M+Na]$^+$, 60%); Anal. Calcd. For C$_{14}$H$_{12}$ClNO: C, 68.44; H, 4.92; N, 5.70. Found: C, 68.40; H, 4.89; N, 5.61.

6-(3-Chlorophenyl)-4-methyl-4-phenyl-1,4-dihydro-benzo[d][1,3]oxazin-2-one was prepared, from 1-(4-amino-3'-chloro-biphenyl-3-yl)-ethanone (0.2 g, 0.82 mmol) and phenylmagnesium bromide followed by treatment with CDI in THF, as a white solid: mp 179-180° C.; $^1$H-NMR (CDCl$_3$) δ 8.27 (s, 1H, D$_2$O exchangeable), 7.51-7.57 (m, 2H), 7.28-7.45 (m, 9H), 6.92 (d, 1H, J=8.4 Hz), 2.12 (s, 3H); MS (ESI) m/z 348 ([M−H]$^-$, 100%); Anal. Calcd. For C$_{21}$H$_{16}$C$_1$NO$_2$: C, 72.10; H, 4.61; N, 4.00. Found: C, 71.72; H, 4.86; N, 3.91.

The title compound was prepared, according to the procedure of Example 16 starting with 6-(3-chlorophenyl)-4-methyl-4-phenyl-1,4-dihydro-benzo[d][1,3]oxazin-2-one, as a white solid: mp 202-203° C.; $^1$H-NMR (CDCl$_3$) δ 8.9 (s, 1H), 7.59-7.56 (m, 2H), 7.49-7.30 (m, 9H), 6.91 (d, 1H, J=8.19 Hz), 2.2 (s, 3H); MS (ES) m/z 364 ([M−H]$^-$).

EXAMPLE 37

4-Allyl-6-(3-chlorophenyl)-4-methyl-1,4-dihydro-2H-3,1-benzoxazine-2-thione

To a solution of 1-(4-amino-3'-chloro-biphenyl-3-yl)-ethanone (0.2 g, 0.82 mmol) in anhydrous THF (10 mL) was added a solution of allylmagnesium bromide in ether (1.0 M, 3 mL, 3 mmol) at 0° C. under nitrogen. The reaction solution was slowly warmed to ambient temperature and stirred under nitrogen for 1 hour. A saturated aqueous ammonium chloride solution (10 mL) was added and was followed by addition of ethyl acetate (50 mL). The organic layer was separated and the aqueous layer was extracted with ethyl acetate (3×10 mL). The combined organic layers were washed with brine and dried with MgSO$_4$. After removal of solvent, the residue was purified by a flash chromatography (silica gel, hexane:ethyl acetate/3:1) to afford an amino carbinol intermediate which was used in next step without further purification.

To a solution of the above amino carbinol in anhydrous THF was added CDI (0.38 g, 2.3 mmol) at ambient temperature under nitrogen. The reaction solution was heated at 55° C. for 12 hours and then cooled to room temperature. The solvent was removed in vacuo and the residue was purified by a flash chromatography (silica gel, hexane:ethyl acetate/2:1) to yield 4-allyl-6-(3-chlorophenyl)-4-methyl-1,4-dihydro-benzo[d][1,3]oxazin-2-one as a white solid (130 mg, 52%): mp 128-129° C.; $^1$H-NMR (CDCl$_3$) δ 8.68 (s, 1H, D$_2$O exchangeable), 7.50 (s, 1H), 7.44 (dd, 1H, J=8.2, 1.9 Hz), 7.31-7.40 (m, 3H), 7.25 (d, 1H, J=1.6 Hz), 6.92 (d, 1H, J=8.2 Hz), 5.70-5.85 (m, 1H), 5.17 (m, 2H), 2.76 (m, 2H), 1.79 (s, 3H); MS (ESI) m/z 314 ([M+H]$^+$, 40%); Anal. Calcd. For C$_{18}$H$_{16}$ClNO$_2$: C, 68.90; H, 5.14; N, 4.46. Found: C, 68.90; H, 5.18; N, 4.43.

The title compound was prepared according to the procedure of Example 16 starting with 4-allyl-6-(3-chloro-phenyl)-4-methyl-1,4-dihydro-benzo[d][1,3]oxazin-2-one: mp 150-151° C.; $^1$H-NMR (CDCl$_3$) δ 8.9 (s, 1H), 7.50-7.47 (m, 2H), 7.40-7.35 (m, 3H), 7.27 (s, 1H), 6.87 (d, 1H, J=8.22 Hz), 5.81-5.72 (m, 1H), 5.19-5.13 (m, 2H), 2.78-2.75 (m, 2H), 1.82 (s, 3H); MS (ES) m/z 328 ([M−H]⁻).

EXAMPLE 38

3-Chloro-5-(4,4-dimethyl-2-thioxo-1,4-dihydro-2H-3,1-benzoxazin-6-yl)benzonitrile 3-Chloro-5-(4,4-dimethyl-2-oxo-1,4-dihydro-2H-benzo[d][1,3]oxazin-6-yl)-benzonitrile was prepared, from (1,4-dihydro-4,4-dimethyl-2-oxo-2H-3,1-benzoxin-6-yl)boronic acid and 1-bromo-3-chlorobenzonitrile according to the procedure of Example 5, as a white solid: mp 256-257° C.; $^1$H-NMR (DMSO-d$_6$) δ 10.4 (s, 1H), 8.22 (bs, 1H), 8.15 (bs, 1H), 7.98 (bs, 1H), 7.74-7.71 (m, 2H), 6.97 (d, 1H, J=8.09 Hz), 1.7 (s, 6H); MS (ESI) m/z 311 ([M−H]⁻, 100%); Anal. Calcd. For C$_{17}$H$_{13}$ClN$_2$O$_2$: C, 65.29, H, 4.19, N, 8.96. Found: C, 65.25, H, 3.92, N, 8.71.

The title compound was prepared according to the procedure of Example 16 starting with 3-chloro-5-(4,4-dimethyl-2-oxo-1,4-dihydro-2H-benzo[d][1,3]oxazin-6-yl)-benzonitrile: mp 249-251° C.; $^1$H-NMR (CDCl$_3$) δ 9.7 (s, 1H), 7.74-7.73 (m, 1H), 7.71-7.70 (m, 1H), 7.64-7.63 (m, 1H), 7.48 (dd, 1H, J=8.24, 1.86 Hz), 7.3 (d, 1H, J=1.73 Hz), 7.01 (d, 1H, J=8.24 Hz), 1.8 (s, 6H); MS (ES) m/z 327/329 ([M−H]⁻).

EXAMPLE 39

6-(3,5-Difluorophenyl)-4,4-dimethyl-1,4-dihydro-2H-3,1-benzoxazine-2-thione 6-(3,5-difluoro-phenyl)-4,4-dimethyl-1,4-dihydrobenzo[d][1,3]oxazin-2-one was prepared, according to the procedure of Example 5 from (4,4-dimethyl-1,4-dihydro-2-oxo-2H-3,1-benzoxazin-6-yl)boronic acid and 1-bromo-3,5-difluorobenzene, as a white solid: mp 218-219° C.; $^1$H-NMR (DMSO-d$_6$) δ 10.4 (s, 1H), 7.67-7.65 (m, 2H), 7.49 (d, 2H, J=7.73 Hz), 7.19 (t, 1H, J=9.29 Hz), 6.96 (d, 1H, J=8.88 Hz), 1.7 (s, 6H); MS (APCI) m/z 290 ([M+H]⁺, 100%); Anal. Calcd. For C$_{16}$H$_{13}$F$_2$NO$_2$: C, 66.43; H, 4.53; N, 4.84. Found: C, 66.01; H, 4.46; N, 4.67.

The title compound was prepared according to the procedure of Example 16 starting with 6-(3,5-Difluoro-phenyl)-4,4-dimethyl-1,4-dihydro-benzo[d][1,3]oxazin-2-one: mp 224-225° C.; $^1$H-NMR (CDCl$_3$) δ 9.7 (s, 1H), 7.48 (dd, 1H, J=8.16, 1.74 Hz), 7.31 (d, 1H, J=1.66 Hz), 7.08-7.03 (m, 2H), 6.98 (d, 1H, J=8.23 Hz), 6.85-6.78 (m, 1H), 1.8 (s, 6H); MS (ES) m/z 304 ([M−H]⁻).

EXAMPLE 40

6-(3-Fluoro-5-methoxyphenyl)-4,4-dimethyl-1,4-dihydro-2H-3,1-benzoxazine-2-thione 6-(3-Fluoro-5-methoxy-phenyl)-4,4-dimethyl-1,4-dihydro-benzo[d][1,3]oxazin-2-one was prepared, from (1,4-dihydro-4,4-dimethyl-2-oxo-2H-3,1-benzoxin-6-yl)boronic acid and 3-bromo-5-fluoroanisole according to the procedure of Example 5, as a white solid: mp 181-182° C.; $^1$H-NMR (DMSO-d$_6$) δ 10.4 (s, 1H), 7.62-7.59 (m, 2H), 7.13-7.06 (m, 2H), 6.97-6.94 (d, 1H, J=8.89 Hz), 6.80 (dt, 1H, J=10.95, 2.12 Hz), 3.8 (s, 3H), 1.7 (s, 6H); MS (ESI) m/z 302 ([M+H]⁺, 100%); Anal. Calcd. For C$_{17}$H$_{16}$FNO$_3$.0.1 H$_2$O: C, 67.36; H, 5.39; N, 4.62. Found: C, 67.11; H, 5.44; N, 4.48.

The title compound was prepared, according to the procedure of Example 16 starting with 6-(3-fluoro-5-methoxy-phenyl)-4,4-dimethyl-1,4-dihydro-benzo[d][1,3]oxazin-2-one, as a white solid: mp 170-171° C.; $^1$H-NMR (CDCl$_3$) δ 9.2 (s, 1H), 7.48 (dd, 1H, J=8.18, 1.84 Hz), 7.32 (d, 1H, J=1.66 Hz), 6.91 (d, 1H, J=8.23 Hz), 6.84 (d, 1H, J=2.11 Hz), 6.82-6.81 (m, 1H), 6.66-6.61 (m, 1H), 3.9 (s, 3H), 1.8 (s, 6H); MS (ES) m/z 316 ([M−H]⁻).

EXAMPLE 41

3-(4,4-Dimethyl-2-thioxo-1,4-dihydro-2H-3,1-benzoxazin-6-yl)-5-methoxybenzonitrile A mixture of (4,4-dimethyl-1,4-dihydro-2-oxo-2H-3,1-benzoxazin-6-yl)boronic acid (4.2 g, 19.0 mmol), 3-cyano-5-methoxybenzyltriflate (5.1 g, 19.0 mmol), tetrakis(triphenylphosphine)-palladium (0) (1.1 g, 0.95 mmol), sodium carbonate (4.0 g, 38.0 mmol), lithium bromide (5 g, 57 mmol) in DME (50 mL), and water (25 mL) under a blanket of nitrogen, was stirred for 15 minutes at 50° C. This solution was then was heated at 85° C. for 1 hour. The reaction mixture was cooled to room temperature and ethyl acetate (100 mL) was added. The organic layers were washed twice with aqueous ammonium chloride (100 mL) and once with brine (100 mL), dried over magnesium sulfate and concentrated. Purification via chromatography (silica gel, 40% ethyl acetate/hexane) gave 3-(4,4-dimethyl-2-oxo-1,4-dihydro-2H-benzo[d][1,3]oxazin-6-yl)-5-methoxy-benzonitrile as a white solid (0.69 g, 53%): mp 254-255° C.; $^1$H-NMR (DMSO-d$_6$) δ 10.4 (s, 1H), 7.84 (s, 1H), 7.67-7.61 (m, 2H), 7.55 (bs, 1H), 7.4 (bs 1H) 6.99 (d, 1H, J=7.94 Hz), 3.88 (s, 3H), 1.67 (s, 6H); MS (EI) m/z 308 ([M+H]⁺, 30%); Anal. Calcd. For C$_{18}$H$_{16}$N$_2$O$_3$: C, 68.13; H, 5.40; N, 8.83. Found: C, 68.03; H, 5.22; N, 8.46.

The title compound was prepared, according to the procedure of Example 16 starting with 3-(4,4-dimethyl-2-oxo-1,4-dihydro-2H-benzo[d][1,3]oxazin-6-yl)-5-methoxy-benzonitrile, as an off-white solid: mp 201-202° C.; $^1$H-NMR (CDCl$_3$) δ 9.1 (s, 1H), 7.48 (dd, 1H, J=8.16, 1.8 Hz), 7.41 (s, 1H), 7.31 (d, 1H, J=1.69 Hz), 7.27 (m, 1H), 7.14 (m, 1H), 6.92 (d, 1H, J=8.2 Hz), 3.9 (s, 3H), 1.8 (s, 6H); MS (ES) m/z 323 ([M−H]⁻).

EXAMPLE 42

6-(3-Fluorophenyl)-4,4-dimethyl-1,4-dihydro-2H-3,1-benzoxazine-2-thione 6-(3-Fluoro-phenyl)-4,4-dimethyl-1,4-dihydro-benzo[d][1,3]oxazin-2-one was prepared, from 6-bromo-4,4-dimethyl-1,4-dihydro-benzo[d][1,3]oxazin-2-one and 1-bromo-3-fluorobenzene according to the procedure of Example 4, as a light yellow solid: mp 181-182° C.; $^1$H-NMR (DMSO-d$_6$) δ 10.4 (s, 1H), 7.62-7.44 (m, 5H), 7.16 (t, 1H, J=2.22 Hz), 6.97 (d, 1H, J=8.83 Hz), 1.67 (s, 6H); MS (EI) m/z 271 ([M+H]⁺, 40%); Anal. Calcd. For C$_{16}$H$_{14}$FNO$_2$: C, 69.91; H, 5.3; N, 5.1. Found: C, 70.0; H, 5.32; N, 4.92.

The title compound was prepared, according to the procedure of Example 16 using 6-(3-Fluoro-phenyl)-4,4-dimethyl-1,4-dihydro-benzo[d][1,3]oxazin-2-one, as a white solid: mp 194-195° C.; $^1$H-NMR (CDCl$_3$) δ 8.9 (s, 1H), 7.50 (dd, 1H, J=8.15, 1.73 Hz), 7.46-7.38 (m, 1H), 7.34-7.30 (m, 2H), 7.25-7.21 (m, 1H), 7.10-7.04 (m, 1H), 6.89 (d, 1H, J=8.21 Hz), 1.8 (s, 6H); MS (ES) m/z 286 ([M−H]⁻).

EXAMPLE 43

6-[3-Fluoro-5-(trifluoromethyl)phenyl]-4,4-dimethyl-1,4-dihydro-2H-3,1-benzoxazine-2-thione 6-(3-Fluoro-5-trifluoromethyl-phenyl)-4,4-dimethyl-1,4-dihydro-benzo[d][1,3]oxazin-2-one was prepared from (1,4-dihydro-4,4-dimethyl-2-oxo-2H-3,1-benzoxin-6-yl)boronic acid and 1-bromo-3-fluoro-5-trifluoromethylbenzene according to the procedure of Example 5, as a white solid: mp 207-208° C.; $^1$H-NMR (DMSO-d$_6$) δ 10.4 (s, 1H), 7.94-7.9 (m, 2H), 7.73-7.7 (m, 2H), 7.63 (d, 1H, J=8.58 Hz), 6.99 (d, 1H, J=8.68 Hz), 1.7 (s, 6H); MS (EI) m/z 339 ([M+]$^-$, 60%); Anal. Calcd. For C$_{17}$H$_{13}$F$_4$NO$_2$: C, 60.18; H, 3.86; N, 4.13. Found: C, 59.9; H, 3.99; N, 4.06.

The title compound was prepared, according to the procedure of Example 16 starting with 6-(3-fluoro-5-trifluoromethyl-phenyl)-4,4-dimethyl-1,4-dihydro-benzo[d][1,3]oxazin-2-one, as a white solid: mp 204-206° C.; $^1$H-NMR (CDCl$_3$) δ 9.2 (s, 1H), 7.56 (s, 1H), 7.5 (dd, 1H, J=8.14, 1.97 Hz), 7.44-7.38 (m, 1H), 7.36-7.30 (m, 2H), 6.92 (d, 1H, J=8.14 Hz), 1.83 (s, 6H); MS (ES) m/z 354 ([M−H]$^-$).

EXAMPLE 44

6-(2-Fluorophenyl)-4,4-dimethyl-1,4-dihydro-2H-3,1-benzoxazine-2-thione 6-(2-Fluoro-phenyl)-4,4-dimethyl-1,4-dihydro-benzo[d][1,3]oxazin-2-one was prepared, according to the procedure of Example 5 from (1,4-dihydro-4,4-dimethyl-2-oxo-2H-3,1-benzoxin-6-yl)boronic acid and 1-bromo-2-fluorobenzene, as off-white crystals: mp 164-165° C.; $^1$H-NMR (DMSO-d$_6$) δ 10.33 (s, 1H), 7.56 (m, 1H), 7.25-7.45 (m, 4H), 6.98 (d, 1H, J=8.7 Hz), 1.64 (s, 6H).

The title compound was prepared, according to the procedure of Example 16 starting with 6-(2-fluoro-phenyl)-4,4-dimethyl-1,4-dihydro-benzo[d][1,3]oxazin-2-one, as a white solid: mp 171-173° C.; $^1$H-NMR (CDCl$_3$) δ 8.97 (s, 1H), 7.5-7.13 (m, 6H), 6.88 (d, 1H, J=8.14 Hz), 1.80 (s, 6H); MS (ES) m/z 286 ([M−H]$^-$).

EXAMPLE 45

6-(3,4-Difluorophenyl)-4,4-dimethyl-1,4-dihydro-2H-3,1-benzoxazine-2-thione 6-(3,4-Difluoro-phenyl)-4,4-dimethyl-1,4-dihydro-benzo[d][1,3]oxazin-2-one was prepared, according to the procedure of Example 5 from (1,4-dihydro-4,4-dimethyl-2-oxo-2H-3,1-benzoxin-6-yl)boronic acid and 1-bromo-3,4-difluorobenzene, as off-white crystals: mp 207-208° C.; $^1$H-NMR (DMSO-d$_6$) δ 10.35 (s, 1H), 7.79 (m, 1H), 7.40-7.63 (m, 4H), 6.95 (d, 1H, J=8.9 Hz), 1.62 (s, 6H).

The title compound was prepared, according to the procedure of Example 16 starting with 6-(3,4-difluoro-phenyl)-4,4-dimethyl-1,4-dihydro-benzo[d][1,3]oxazin-2-one, as a yellow solid: mp 209-211° C.; $^1$H-NMR (CDCl$_3$) δ 8.94 (s, 1H), 7.44 (dd, 1H, J=8.35, 1.98 Hz), 7.36-7.22 (m, 4H), 6.87 (d, 1H, J=8.35 Hz), 1.81 (s, 6H); MS (ES) m/z 304 ([M−H]$^-$).

EXAMPLE 46

6-(4-Fluorophenyl)-4,4-dimethyl-1,4-dihydro-2H-3,1-benzoxazine-2-thione 6-(4-Fluoro-phenyl)-4,4-dimethyl-1,4-dihydro-benzo[d][1,3]oxazin-2-one was prepared, according to the procedure of Example 5 from (1,4-dihydro-4,4-dimethyl-2-oxo-2H-3,1-benzoxin-6-yl)boronic acid and 1-bromo-4-fluorobenzene, as off-white crystals: mp 232-233° C.; $^1$H-NMR (DMSO-d$_6$) δ 10.3 (s, 1H), 7.74 (m, 2H), 7.53 (m, 2H), 7.28 (m, 2H), 6.96 (d, 1H, J=8.9 Hz), 1.63 (s, 6H).

The title compound was prepared, according to the procedure of Example 16 starting with 6-(4-fluoro-phenyl)-4,4-dimethyl-1,4-dihydro-benzo[d][1,3]oxazin-2-one, as a white solid: mp 221-223° C.; $^1$H-NMR (CDCl$_3$) δ 8.98 (s, 1H), 7.5-7.44 (m, 3H), 7.5 (m, 1H), 7.17-7.10 (m, 2H), 6.87 (d, 1H, J=8.14 Hz), 1.81 (s, 6H); MS (ES) m/z 286 ([M−H]$^-$).

EXAMPLE 47

3-(4,4-Dimethyl-2-thioxo-1,4-dihydro-2H-3,1-benzoxazin-6-yl)-4-fluorobenzonitrile 3-(4,4-Dimethyl-2-oxo-1,4-dihydro-2H-benzo[d][1,3]oxazin-6-yl)-4-fluoro-benzonitrile was prepared, from (1,4-dihydro-4,4-dimethyl-2-oxo-2H-3,1-benzoxin-6-yl)boronic acid and 5-bromo-2-fluorobenzonitrile according to the procedure of Example 5, as a white solid: mp 229-230° C.; $^1$H-NMR (DMSO-d$_6$) δ 10.4 (s, 1H), 8.15 (dd, 1H, J=7.39, 2.12 Hz), 7.95-7.89 (m, 1H), 7.59-7.48 (m, 3H), 6.99 (d, 1H, J=8.1 Hz), 1.7 (s, 6H); MS (APCI) m/z 297 ([M+H]$^+$, 100%); Anal. Calcd. For C$_{17}$H$_{13}$FN$_2$O$_2$: C, 68.91; H, 4.42; N, 9.45. Found: C, 68.74; H, 4.83; N, 9.10.

The title compound was prepared, according to the procedure of Example 16 starting with 3-(4,4-dimethyl-2-oxo-1,4-dihydro-2H-benzo[d][1,3]oxazin-6-yl)-4-fluoro-benzonitrile, as a yellow solid: mp 250-251° C.; $^1$H-NMR (CDCl$_3$) δ 8.83 (s, 1H), 7.73 (dd, 1H, J=8.34, 2.19 Hz), 7.68-7.64 (m, 1H), 7.48-7.44 (m, 1H), 7.32-7.28 (m, 2H), 6.9 (d, 1H, J=8.34 Hz), 1.81 (s, 6H); MS (ES) m/z 311 ([M−H]$^-$).

EXAMPLE 48

6-(2,3-Difluorophenyl)-4,4-dimethyl-1,4-dihydro-2H-3,1-benzoxazine-2-thione 6-(2,3-Difluoro-phenyl)-4,4-dimethyl-1,4-dihydro-benzo[d][1,3]oxazin-2-one was prepared, according to the procedure of Example 5 from (1,4-dihydro-4,4-dimethyl-2-oxo-2H-3,1-benzoxazin-6-yl)boronic acid and 2,3-difluorobenzyltriflate, as a yellow solid: mp 166-167° C.; $^1$H-NMR (DMSO-d$_6$) δ 10.4 (s, 1H), 7.5-7.2 (m, 5H), 7.0 (m, 1H), 1.7 (s, 6H); MS (EI) m/z 289 ([M+H]$^+$); Anal. Calcd. For C$_{16}$H$_{13}$F$_2$NO$_2$: C, 66.43; H, 4.53; N, 4.84. Found: C, 66.15; H, 4.37; N, 4.64.

The title compound was prepared, according to the procedure of Example 16 starting with 6-(2,3-difluoro-phenyl)-4,4-dimethyl-1,4-dihydro-benzo[d][1,3]oxazin-2-one, as a white solid: mp 197-198° C.; $^1$H-NMR (CDCl$_3$) δ 9.02 (s, 1H), 7.49-7.45 (m, 1H), 7.34 (s, 1H), 7.2-7.13 (m, 3H), 6.9 (d, 1H, J=8.14 Hz), 1.80 (s, 6H); MS (ES) m/z 304 ([M−H]$^-$).

EXAMPLE 49

3-(8-Bromo-4,4-dimethyl-2-thioxo-1,4-dihydro-2H-3,1-benzoxazin-6-yl)-5-fluorobenzonitrile To a mixture of 3-(4,4-dimethyl-2-oxo-1,4-dihydro-2H-3,1-benzoxazin-6-yl)-5-fluorobenzonitrile (0.5 g, 1.7 mmol) and sodium acetate (0.2 g, 2.4 mmol) in acetic acid (5 mL) was added, at room temperature under nitrogen, bromine (0.12 mL, 2.34 mmol). The reaction mixture was stirred for 20 hours and then poured into ice water (30 mL). The precipitate was collected on a filter and washed with water (3×5 mL) to yield 3-(8-bromo-4,4-dimethyl-2-oxo-1,4-dihydro-2H-3,1-benzoxazin-6-yl)-5-fluorobenzonitrile as an off-white solid (0.48 g, 75%): mp 216-217° C.; $^1$H-NMR (DMSO-d$_6$) δ 9.78 (s, 1H), 8.18 (t, 1H, J=1.6 Hz), 8.02-8.08 (m, 2H), 7.81 (m, 1H), 7.75 (d, 1H, J=1.8 Hz), 1.66 (s, 6H). MS (ESI) m/z 373, 375 [M−H]$^-$.

The title compound was prepared according to the procedure of Example 16 starting with 3-(8-bromo-4,4-dimethyl-2-oxo-1,4-dihydro-2H-3,1-benzoxazin-6-yl)-5-fluorobenzonitrile: mp 219-220° C.; $^1$H-NMR (CDCl$_3$) δ 9.05 (s, 1H), 7.70 (d, 1H, J=1.98 Hz), 7.6 (m, 1H), 7.48-7.44 (m, 1H), 7.4-7.36 (m, 1H), 7.26 (m, 1H), 1.80 (s, 6H); MS (ES) m/z 304 ([M−H]−).

EXAMPLE 50

4,4-Dimethyl-6-(3-nitrophenyl)-1,4-dihydro-2H-3,1-benzoxazine-2-thione 4,4-Dimethyl-6-(3-nitrophenyl)-1,4-dihydrobenzo[d][1,3]oxazin-2-one was prepared, from 6-iodo-4,4-dimethyl-1,4-dihydro-benzo[d][1,3]oxazin-2-one and 3-nitrophenyl boronic acid according to the procedure of Example 4, as a yellowish solid: mp 244-245° C.; $^1$H-NMR (DMSO-d$_6$) δ 10.38 (s, 1H, D$_2$O exchangeable), 8.47 (s, 1H), 8.14-8.20 (m, 2H), 7.70-7.76 (m, 3H), 7.01 (d, 1H, J=8.1 Hz), 1.68 (s, 6H); MS (EI) m/z 297 ([M−H]−, 100%); Anal. Calcd. For C$_{16}$H$_{14}$N$_2$O$_4$: C, 64.42; H, 4.73; N, 9.39. Found: C, 63.93; H, 4.91; N, 8.71.

The title compound was prepared, according to the procedure of Example 16 starting with 4,4-dimethyl-6-(3-nitrophenyl)-1,4-dihydro-benzo[d][1,3]oxazin-2-one, as a yellow solid: mp 224-226° C.; $^1$H-NMR (CDCl$_3$) δ 8.89 (s, 1H), 8.40 (s, 1H), 8.26-8.22 (m, 1H), 7.88-7.86 (m, 1H), 7.64 (t, 1H, J=7.97 Hz), 7.57 (dd, 1H, J=8.21, 1.3 Hz), 7.40 (m, 1H), 6.94 (d, 1H, J=8.22 Hz), 1.80 (s, 6H); MS (ES) m/z 313 ([M−H]−).

EXAMPLE 51

6-(3-Chlorophenyl)-4,4-diethyl-1,4-dihydro-2H-3,1-benzoxazine-2-thione 6-(3-Chlorophenyl)-4,4-diethyl-1,4-dihydrobenzo[d][1,3]oxazin-2-one was prepared, from 4,4-diethyl-6-iodo-1,4-dihydrobenzo[d][1,3]oxazin-2-one and 3-chlorophenyl boronic acid according to the procedure of Example 4, as a white solid: mp 150-151° C.; $^1$H-NMR (CDCl$_3$) δ 8.52 (s, 1H, D$_2$O exchangeable), 7.50 (s, 1H), 7.31-7.44 (m, 4H), 7.16 (d, 1H, J=1.5 Hz), 6.89 (d, 1H, J=8.2 Hz), 2.03 (m, 4H), 0.94 (t, 6H, J=7.4 Hz); MS (EI) m/z 315 (M+, 53%). Anal. Calcd. For C$_{18}$H$_{18}$ClNO$_2$: C, 68.46; H, 5.75; N, 4.44. Found: C, 68.16; H, 5.81; N, 4.32.

The title compound was prepared, according to the procedure of Example 16 starting with 6-(3-chloro-phenyl)-4,4-diethyl-1,4-dihydro-benzo[d][1,3]oxazin-2-one, as a white solid: mp 148-150° C.; $^1$H-NMR (CDCl$_3$) δ 9.27 (s, 1H), 7.50-7.45 (m, 2H), 7.40-7.34 (m, 3H), 7.17 (d, 1H, J=1.64 Hz), 6.94 (d, 1H, J=8.22 Hz), 2.18-2.01 (m, 4H), 0.94 (t, 6H, J=7.33 Hz); MS (ES) m/z 303/332 ([M−H]−).

EXAMPLE 52

6-(3-Methoxyphenyl)-4,4-dimethyl-1,4-dihydro-2H-3,1-benzoxazine-2-thione 6-(3-Methoxy-phenyl)-4,4-dimethyl-1,4-dihydro-benzo[d][1,3]oxazin-2-one was prepared, according to the procedure of Example 4 from 6-bromo-4,4-dimethyl-1,4-dihydrobenzo[d][1,3]oxazin-2-one and 3-methoxyphenyl boronic acid, as a yellow solid: mp 164-165° C.; $^1$H-NMR (DMSO-d$_6$) δ 10.3 (s, 1H), 7.56 (m, 2H), 7.36 (t, 1H, J=7.89 Hz), 7.20 (m, 2H), 6.96 (d, 1H, J=8.88 Hz), 6.91 (dd, 1H, J=8.13, 2.35 Hz), 3.8 (s, 3H), 1.7 (s, 6H); MS (ESI) m/z 284 ([M+H]+, 30%); Anal. Calcd. For C$_{17}$H$_{17}$NO$_3$: C, 72.07; H, 6.05; N, 4.94. Found: C, 70.58; H, 5.73; N, 4.67.

The title compound was prepared, according to the procedure of Example 16 starting with 6-(3-Methoxy-phenyl)-4,4-dimethyl-1,4-dihydro-benzo[d][1,3]oxazin-2-one, as a white solid: mp 142-143° C.; $^1$H-NMR (CDCl$_3$) δ 8.96 (s, 1H), 7.51 (dd, 1H, J=8.2, 1.84 Hz), 7.40-7.35 (m, 2H), 7.13-7.10 (m, 1H), 7.05 (t, 1H, J=2.21 Hz), 6.90 (dd, 1H, J=8.09, 2.46 Hz), 6.87 (d, 1H, J=8.2 Hz), 3.87 (s, 3H), 1.8 (s, 6H); MS (ES) m/z 298 ([M−H]−).

EXAMPLE 53

6-(2-Chlorophenyl)-4,4-dimethyl-1,4-dihydro-2H-3,1-benzoxazine-2-thione 6-(2-Chloro-phenyl)-4,4-dimethyl-1,4-dihydro-benzo[d][1,3]oxazin-2-one was prepared, according to the procedure of Example 4 from 6-bromo-4,4-dimethyl-1,4-dihydro-benzo[d][1,3]oxazin-2-one and 2-chlorophenyl boronic acid, as a white solid: mp 181-182° C.; MS (ESI) m/z 288 ([M+H]+, 70%); Anal. Calcd. For C$_{16}$H$_{14}$ClNO$_2$: C, 66.79; H, 4.90; N, 4.87. Found: C, 66.78; H, 4.82; N, 4.55.

The title compound was prepared, according to the procedure of Example 16 starting with 6-(2-chloro-phenyl)-4,4-dimethyl-1,4-dihydro-benzo[d][1,3]oxazin-2-one, as a white solid: mp 171-172° C.; $^1$H-NMR (CDCl$_3$) δ 8.95 (s, 1H), 7.51-7.47 (m, 1H), 7.40-7.27 (m, 5H), 6.87 (d, 1H, J=8.14 Hz), 1.79 (s, 6H); MS (ES) m/z 302/304 ([M−H]−).

EXAMPLE 54

4-Benzyl-6-(3-chlorophenyl)-4-methyl-1,4-dihydro-2H-3,1-benzoxazine-2-thione A mixture of 1-(4-amino-3-chloro-biphenyl-3-yl)-1-benzyl-ethanol (prepared from 1-(4-amino-3'-chloro-biphenyl-3-yl)-ethanone and benzylmagnesium bromide according to procedure described previously, 0.14 g, 0.42 mmol) and triphosgene (0.04 g, 0.14 mmol) in dry THF (10 mL) was stirred under a blanket of nitrogen for 10 minutes. THF was removed and the residue purified via flash chromatography (silica gel, 35% ethyl acetate/hexane) to give 4-benzyl-6-(3-chloro-phenyl)-4-methyl-1,4-dihydro-benzo[d][1,3]oxazin-2-one (0.045 g, 30%) as an off-white solid: mp 187-188° C.; $^1$H-NMR (DMSO-d$_6$) δ 10.1 (s, 1H), 7.70 (t, 1H, J=2.3 Hz), 7.6 (d, 1H, J=8.0 Hz), 7.58-7.53 (m, 2H), 7.46 (t, 1H, J=8.0 Hz), 7.38 (d, 1H, J=8.0 Hz), 7.22-7.17 (m, 3H), 7.06-7.0 (m, 2H), 6.84 (d, 1H, J=9.14 Hz), 3.24 (d, 1H, J=14.3 Hz), 3.06 (d, 1H, J=14.3 Hz), 1.68 (s, 3H); MS (ESI) m/z 364 ([M+H]+, 100%); Anal. Calcd. For C$_{22}$H$_{18}$C$_1$NO$_2$: C, 72.63; H, 4.99; N, 3.85. Found: C, 71.82; H, 5.09; N, 3.58.

The title compound was prepared, according to the procedure of Example 16 starting with 4-benzyl-6-(3-chloro-phenyl)-4-methyl-1,4-dihydro-benzo[d][1,3]oxazin-2-one, as a white solid: $^1$H-NMR (CDCl$_3$) δ 9.09 (s, 1H), 7.63 (dd, 1H, J=8.03, 1.83 Hz), 7.38-7.22 (m, 7H), 7.04-6.97 (m, 3H), 6.83 (d, 1H, J=8.22 Hz), 3.22 (s, 2H), 1.86 (s, 3H); MS (ES) m/z 378/380 ([M−H]−).

EXAMPLE 55

6-(3-Bromo-5-fluorophenyl)-4,4-dimethyl-1,4-dihydro-2H-3,1-benzoxazine-2-thione 6-(3-Bromo-5-fluorophenyl)-4,4-dimethyl-1,4-dihydrobenzo[d][1,3]oxazin-2-one was prepared, from (1,4-dihydro-4,4-dimethyl-2-oxo-2H-3,1-benzoxazin-6-yl)boronic acid and 1,3-dibromo-5-fluorobenzene following the procedure of Example 5, as a white solid: mp 182-183° C.; $^1$H-NMR (DMSO-d$_6$) δ 10.36 (s, 1H, D$_2$O exchangeable), 7.78 (s, 1H), 7.58-7.65 (m, 3H), 7.49 (dd, 1H, J=8.3, 1.8 Hz), 6.96 (d, 1H, J=8.5 Hz), 1.69 (s, 6H); $^{19}$F-NMR (DMSO-d$_6$) δ-112.46 (m, 1F); MS (CI) m/z 352 ([M+H]+, 78%), 350 ([M+H]+, 75%); Anal. Calcd. For C$_{16}$H$_{13}$BrFNO$_2$: C, 54.88; H, 3.74; N, 4.00. Found: C, 54.83; H, 3.82; N, 3.95.

The title compound was prepared, according to the procedure of Example 16 starting with 6-(3-bromo-5-fluoro-phenyl)-4,4-dimethyl-1,4-dihydro-benzo[d][1,3]oxazin-2-one, as a yellow solid: mp 221-222° C.; $^1$H-NMR (CDCl$_3$) δ 9.28 (s, 1H), 7.49-7.45 (m, 2H), 7.30 (d, 1H, J=1.71 Hz), 7.24 (t, 1H, J=2.07 Hz), 7.17 (dt, 1H, J=9.54, 1.99 Hz), 6.93 (d, 1H, J=8.25 Hz), 1.8 (s, 6H); MS (ES) m/z 364/366 ([M−H]$^−$).

EXAMPLE 56

5-(4,4-Dimethyl-2-thioxo-1,4-dihydro-2H-3,1-benzoxazin-6-yl) thiophene-2-carbonitrile 5-(4,4-Dimethyl-2-oxo-1,4-dihydro-2H-benzo[d][1,3]oxazin-6-yl)-thiophene-2-carbonitrile was prepared, according to the procedure of Example 5 using 5-bromo-2-thiophenecarbonitrile and (1,4-dihydro-4,4-dimethyl-2-oxo-2H-3,1-benzoxazin-6-yl)boronic acid, as an off-white solid: mp 264-266° C.; $^1$H-NMR (DMSO-d$_6$) δ 10.3 (s, 1H), 7.97 (d, 1H, J=7.9 Hz), 7.60-7.66 (m, 3H), 6.96 (d, 1H, J=8.1 Hz), 1.65 (s, 6H); MS (APCI) m/z 285 (M+H)$^+$, 302 (M+NH$_4$)$^+$. Anal. Calcd. For C$_{15}$H$_{12}$N$_2$O$_2$S: C, 63.36; H, 4.25; N, 9.85. Found: C, 63.01; H, 4.36; N, 9.39.

The title compound was prepared, according to the procedure of Example 16 using 5-(4,4-dimethyl-2-oxo-1,4-dihydro-2H-benzo[d][1,3]oxazin-6-yl)-thiophene-2-carbonitrile, as a yellow solid: mp 242-244° C.; $^1$H-NMR (CDCl$_3$) δ 9.05 (s, 1H), 7.61 (d, 1H, J=3.89 Hz), 7.54 (dd, 1H, J=8.23, 1.56 Hz), 7.35 (m, 1H), 7.24 (d, 1H, J=3.89 Hz), 6.88 (d, 1H, J=8.26 Hz), 1.8 (s, 6H); MS (ES) m/z 299 ([M−H]$^−$).

EXAMPLE 57

3-Fluoro-5-(8-fluoro-4,4-dimethyl-2-thioxo-1,4-dihydro-2H-3,1-benzoxazin-6-yl)benzonitrile N-(tert-Butoxycarbonylamino)-3-fluorobenzoic acid (Takagishi et al. *Synlett* 4, 360-2 (1992); mp 159-161° C.) was deprotected using trifluoroacetic acid to give o-amino benzoic acid, which was then treated with methylmagnesium bromide to afford o-amino dimethyl carbinol. The o-amino dimethyl carbinol (2.23 g, 13.2 mmol) was treated with 1,1-carbonyldiimidazole (2.8 g, 17.2 mmol) in THF (20 mL) at 50° C. for 12 hours. The solution was then cooled to room temperature and ethyl acetate (100 mL) was added. The organic layer was washed with 10% aqueous HCl solution (2×25 mL), dried over MgSO$_4$ and concentrated. The residue was purified via chromatography (silica gel, 10% ethyl acetate/hexane) to give 8-fluoro-4,4-dimethyl-dihydrobenzo[d][1,3]oxazin-2-one as a white solid (1.3 g, 50%): mp 127-128° C.; $^1$H-NMR (DMSO-d$_6$) ε 10.4 (s, 1H), 7.22-7.12 (m, 2H), 7.07-7.00 (m, 2H), 1.6 (s, 6H); MS (APCI) m/z 196 ([M+H]$^+$, 100%); Anal. Calcd. For C$_{10}$H$_{10}$FNO$_2$: C, 61.53; H, 5.16; N, 7.18. Found: C, 61.27; H, 5.37; N, 7.02.

8-Fluoro-(1,4-dihydro-4,4-dimethyl-2-oxo-2H-3,1-benzoxin-6-yl)boronic acid was prepared from 6-bromo-8-Fluoro-4,4-dimethyl-dihydro-benzo[d][1,3]oxazin-2-one using the procedure of Example 4.

3-Fluoro-5-(8-fluoro-4,4-dimethyl-2-oxo-1,4-dihydro-2H-benzo[d][1,3]oxazin-6-yl)-benzonitrile was prepared, from 8-fluoro-(1,4-dihydro-4,4-dimethyl-2-oxo-2H-3,1-benzoxin-6-yl)boronic acid and 5-bromo-3-fluorobenzonitrile according to the procedure of example 5, as a white solid: mp 256-257° C.; $^1$H-NMR (DMSO-d$_6$) δ 10.5 (s, 1H), 8.20 (bs, 1H), 8.06 (dt, 1H, J=10.48, 2.16 Hz), 7.85-7.82 (m, 1H), 7.77 (dd, 1H, J=11.89, 1.81 Hz), 7.63 (s, 1H), 1.7 (s, 6H); MS (EI) m/z 314 ([M$^+$], 60%).

The title compound was prepared, according to the procedure of Example 16 using 3-Fluoro-5-(8-fluoro-4,4-dimethyl-2-oxo-1,4-dihydro-2H-benzo[d][1,3]oxazin-6-yl)-benzonitrile, as a yellow solid: $^1$H-NMR (CDCl$_3$) δ 8.91 (s, 1H), 7.61 (d, 1H), 7.47 (dt, 1H, J=9.25, 2.0 Hz), 7.39 (m, 1H), 7.33-7.29 (m, 1H), 7.13 (s, 1H), 1.8 (s, 6H).

EXAMPLE 58

3-(1,2-Dihydro-2-thioxospiro[4H-3,1-benzoxazine-4,1-cyclohexan]-6-yl)benzonitrile 3-(1,2-Dihydro-2-oxospiro[4H-3,1-benzoxazine-4,1-cyclohexan]-6-yl)-benzonitrile was prepared, according to Procedure B from spiro-(4,1'-cyclohexane-1,4-dihydro-2-oxo-2H-3,1-benzoxazin-6-yl) boronic acid and 3-bromobenzonitrile, as a tan powder: mp 245-247° C.; $^1$H-NMR (DMSO-d$_6$) δ 10.31 (s, 1H), 8.21 (s, 1H), 8.02 (d, 1H, J=8.0 Hz), 7.78 (d, 1H, J=7.7 Hz), 7.68-7.61 (m, 3H), 6.97 (d, 1H, J=8.2 Hz), 1.98-1.96 (m, 4H), 1.75-1.64 (m, 5H), 1.40-1.32 (m, 1H); MS (EI) m/z 318 [M$^+$]; Anal. Calcd. For C$_{20}$H$_{18}$N$_2$O$_2$.½ H$_2$O: C, 73.38; H, 5.85; N, 8.56. Found: C, 73.86; H, 5.81; N, 8.22.

The title compound was prepared, according to the procedure of Example 16 starting with 3-(1,2-dihydro-2-oxospiro[4H-3,1-benzoxazine-4,1-cyclohexan]-6-yl)benzonitrile, as a white solid: mp 222-224° C.; $^1$H-NMR (CDCl$_3$) δ 9.08 (s, 1H), 7.86-7.81 (m, 1H), 7.77 (dt, 1H, J=7.79, 1.35 Hz), 7.67-7.64 (m, 1H), 7.58 (d, 1H, J=7.77 Hz), 7.48 (dd, 1H, J=8.2, 1.93 Hz), 7.35 (d, 1H, J=1.78 Hz), 6.91 (d, 1H, J=8.2 Hz), 2.30-2.26 (m, 2H), 2.07-1.98 (m, 2H), 1.90-1.70 (m, 4H), 0.39-1.24 (m, 2H); MS (ES) m/z 333 ([M−H]$^−$).

EXAMPLE 59

5-(1,2-Dihydro-2-thioxospiro[4H-3,1-benzoxazine-4,1-cyclohexan]-6-yl)-4-methyl-2-thiophenecarbonitrile 5-(1,2-Dihydro-2-oxospiro[4H-3,1-benzoxazine-4,1-cyclohexan]-6-yl)-4-methyl-2-thiophenecarbonitrile was prepared, according to Procedure B from spiro-(4,1'-cyclohexane-1,4-dihydro-2-oxo-2H-3,1-benzoxazin-6-yl) boronic acid and 2-bromo-3-methyl-5-cyanothiophene, as a white powder: mp 200-203° C.; $^1$H-NMR (DMSO-d$_6$) ε 10.4 (s, 1H), 7.85 (s, 1H), 7.43-7.40 (m, 2H), 7.0 (d, 1H, J=8.8 Hz), 2.27 (s, 3H), 2.00-1.62 (m, 9H), 1.42-1.23 (m, 1H); MS (EI) m/z 338 (M$^+$); Anal. Calcd. For C$_{19}$H$_{18}$N$_2$O$_2$S: C, 67.43; H, 5.36, N, 8.28. Found: C, 67.12; H, 5.45; N, 8.05.

The title compound was prepared, according to the procedure for Example 16 starting with 5-(1,2-Dihydro-2-oxospiro[4H-3,1-benzoxazine-4,1-cyclohexan]-6-yl)-4-methyl-2-thiophenecarbonitrile, as a yellow solid: mp 199-201° C.; $^1$H-NMR (CDCl$_3$) δ 8.92 (s, 1H), 7.5 (s, 1H), 7.36 (dd, 1H, J=8.17, 1.9 Hz), 7.23 (d, 1H, J=1.7 Hz), 6.87 (d, 1H, J=8.18 Hz), 2.3 (s, 3H), 2.05-1.70 (m, 7H), 1.36-1.25 (m, 3H); MS (ES) m/z 353 ([M−H]$^−$).

EXAMPLE 60

5-(1,2-Dihydro-2-thioxospiro[4H-3,1-benzoxazine-4,1-cyclohexan]-6-yl)-2-thiophenecarbonitrile 5-(1,2-Dihydro-2-oxospiro[4H-3,1-benzoxazine-4,1-cyclohexan]-6-yl)-2-thiophenecarbonitrile was prepared, according to Procedure B from spiro-(4,1'-cyclohexane-1,4-dihydro-2-oxo-2H-3,1-benzoxazin-6-yl) boronic acid and 2-bromo-5-cyanothiophene, as a tan powder: mp 243-245° C.; $^1$H-NMR (DMSO-d$_6$) δ 10.41 (s, 1H), 7.98-7.97 (d, 1H, J=3.9 Hz), 7.67-7.60 (m, 3H), 6.97-6.94 (d, 1H, J=8.3 Hz), 1.98-1.92 (m, 4H), 1.74-1.64 (m, 5H), 1.45-1.21 (m, 1H); MS (EI) m/z 324 (M$^+$). Anal. Calcd. For C$_{18}$H$_{16}$N$_2$O$_2$S ½ H$_2$O: C, 65.08; H, 5.04; N, 8.18. Found: C, 64.84; H, 8.40.

The title compound was prepared, according to the procedure for Example 16 starting with 5-(1,2-Dihydro-2-oxospiro [4H-3,1-benzoxazine-4,1-cyclohexan]-6-yl)-2-thiophenecarbonitrile, as a yellow solid: mp 232-233° C.; $^1$H-NMR (CDCl$_3$) δ 8.90 (s, 1H), 7.6 (d, 1H, J=3.93 Hz), 7.36 (d, 1H, J=1.8 Hz), 7.24-7.20 (m, 1H), 6.85 (d, 1H, J=8.25 Hz), 2.28-2.23 (m, 2H), 2.11-1.96 (m, 2H), 1.90-1.70 (m, 5H), 1.38-1.33 (m, 2H); MS (ES) m/z 339 ([M−H]$^-$).

EXAMPLE 61

6-(3-Chloro-4-fluorophenyl)-4,4-dimethyl-1,4-dihydro-2H-3,1-benzoxazin-2-thione 6-(3-Chloro-4-fluoro-phenyl)-4,4-dimethyl-1,4-dihydro-benzo[d][1,3]oxazin-2-one was prepared, from 6-bromo-4,4-dimethyl-1,4-dihydro-benzo[d][1,3]oxazin-2-one and 1-bromo-3-chloro-4-fluorobenzene according to Procedure A, as a white solid: mp 211-212° C.; $^1$H-NMR (DMSO-d$_6$) δ 10.4 (s, 1H), 7.92 (dd, 1H, J=7.13, 2.19 Hz), 7.71-7.66 (m, 1H), 7.60-7.57 (m, 2H), 7.49 (t, 1H, J=8.95 Hz), 6.96 (d, 1H, J=8.01 Hz), 1.67 (s, 6H); MS (EI) m/z 305 ([M+H]$^+$, 20%); Anal. Calcd. For C$_{16}$H$_{13}$ClFNO$_2$: C, 62.86; H, 4.29; N, 4.58. Found: C, 62.52; H, 4.45; N, 4.42.

The title compound was prepared, according to the procedure for Example 16 starting with 6-(3-Chloro-4-fluoro-phenyl)-4,4-dimethyl-1,4-dihydro-benzo[d][1,3]oxazin-2-one, as a white solid: mp 196-197° C.; $^1$H-NMR (CDCl$_3$) δ 9.29 (s, 1H), 7.55 (dd, 1H, J=6.89, 2.28 Hz), 7.45 (dd, 1H, J=8.21, 1.91 Hz), 7.41-7.27 (m, 1H), 7.28-7.27 (m, 1H), 7.22 (t, 1H, J=8.66 Hz), 6.92 (d, 1H, J=8.22 Hz), 1.81 (s, 6H); MS (ES) m/z 320 ([M−H]$^-$).

EXAMPLE 62

5-(4,4-Dimethyl-2-thioxo-1,4-dihydro-2H-3,1-benzoxazin-6-yl)-4-propylthiophene-2-carbonitrile 5-(4,4-Dimethyl-2-oxo-1,4-dihydro-2H-benzo[d][1,3]oxazin-6-yl)-4-n-propyl-thiophene-2-carbonitrile was prepared according to Procedure B from spiro-(4,1'-cyclohexane-1,4-dihydro-2-oxo-2H-3,1-benzoxazin-6-yl) boronic acid and 2-bromo-3-n-propyl-5-thiophenecarbonitrile. White crystals: mp 160-162° C.; IR (KBr) 2220 cm$^{-1}$; $^1$H-NMR (DMSO-d$_6$) δ 10.47 (s, 1H), 7.93 (s, 1H), 7.38-7.36 (m, 2H), 7.01 (d, 1H, J=8.7 Hz), 2.59-2.48 (m, 2H), 1.64-1.51 (m, 2H), 0.85 (t, 3H, J=7.3 Hz). MS (-ESI) m/z [M−H]$^-$ 325; Anal. Calcd. For C$_{18}$H$_{18}$N$_2$O$_2$S.¾H$_2$O: C, 63.60; H, 5.78; N, 8.24. Found: C, 63.48; H, 5.59; N, 8.04.

The title compound was prepared according to the procedure for Example 16 starting with 5-(4,4-Dimethyl-2-oxo-1,4-dihydro-2H-benzo[d][1,3]oxazin-6-yl)-4-propyl-thiophene-2-carbonitrile. A yellow solid: mp 174-175° C.; $^1$H-NMR (CDCl$_3$) δ 9.43 (s, 1H), 7.49 (s, 1H), 7.35 (dd, 1H, J=8.17, 1.8 Hz), 7.19 (d, 1H, J=1.62 Hz), 6.95 (d, 1H, J=8.18 Hz), 2.56 (t, 2H, J=7.53 Hz), 1.79 (s, 6H), 1.60 (m, 2H, J=7.56 Hz), 0.92 (t, 3H, J=7.3 Hz); MS (ES) m/z 341 ([M−H]$^-$).

EXAMPLE 63

4-(4,4-Dimethyl-2-thioxo-1,4-dihydro-2H-3,1-benzoxazin-6-yl)-2-furonitrile 4-(4,4-Dimethyl-2-oxo-1,4-dihydro-2H-benzo[d][1,3]oxazin-6-yl)-furan-2-carbonitrile was prepared from (1,4-dihydro-4,4-dimethyl-2-oxo-2H-3,1-benzoxazin-6-yl)boronic acid and 4-bromo-2-furancarbonitrile according to Procedure B. Off-white solid: mp 255-256° C. $^1$H-NMR (DMSO-d$_6$) δ 10.32 (s, 1H, D$_2$O exchangeable), 8.57 (s, 1H), 8.15 (s, 1H), 7.61 (s, 1H), 7.55 (dd, 1H, J=8.3, 1.5 Hz), 6.92 (d, 1H, J=8.2 Hz), 1.65 (s, 6H); MS (ESI) m/z 269 (M+H, 72%). Anal. Calcd. For C$_{15}$H$_{12}$N$_2$O$_3$: C, 67.16, H, 4.51, N, 10.44. Found: C, 67.14, H, 4.59, N, 10.07.

The title compound was prepared according to the procedure for Example 16 starting with 4-(4,4-dimethyl-2-oxo-1,4-dihydro-2H-benzo[d][1,3]oxazin-6-yl)-furan-2-carbonitrile. An off-white solid: mp 214-216° C.; $^1$H-NMR (CDCl$_3$) δ 8.93 (s, 1H), 7.83 (s, 1H), 7.39 (dd, 1H, J=8.2, 1.87 Hz), 7.35 (s, 1H), 7.22-7.21 (m, 1H), 6.86 (d, 1H, J=8.2 Hz), 1.79 (s, 6H); MS (ES) m/z 283 ([M−H]$^-$).

EXAMPLE 64

4-Butyl-5-(4,4-dimethyl-2-thioxo-1,4-dihydro-2H-3,1-benzoxazin-6-yl)thiophene-2-carbonitrile 5-(4,4-Dimethyl-2-oxo-1,4-dihydro-2H-benzo[d][1,3]oxazin-6-yl)-4-n-butyl-thiophene-2-carbonitrile was prepared according to Procedure B from spiro-(4,1'-cyclohexane-1,4-dihydro-2-oxo-2H-3,1-benzoxazin-6-yl) boronic acid and 2-bromo-3-n-butyl-5-thiophenecarbonitrile. White crystals: mp 167-168° C.; $^1$H-NMR (DMSO-d$_6$) δ 10.46 (s, 1H), 7.93 (s, 1H), 7.38-7.36 (m, 2H), 7.01 (d, 1H, J=8.7 Hz), 2.59 (t, 2H, J=8.1 Hz), 1.63 (s, 6H), 1.58-1.51 (m, 2H), 1.48-1.17 (m, 2H), 0.82 (t, 3H, J=7.4 Hz). MS (-ESI) m/z [M−H]$^-$ 339. Anal. Calcd. For C$_{19}$H$_{20}$N$_2$O$_2$S. ¼H$_2$O: C, 66.16; H, 5.99; N, 8.12. Found: C, 66.33; H, 5.92; N, 7.85.

The title compound was prepared according to the procedure for Example 16 starting with 4-Butyl-5-(4,4-dimethyl-2-oxo-1,4-dihydro-2H-benzo[d][1,3]oxazin-6-yl)-thiophene-2-carbonitrile. A yellow solid: mp 174-175° C.; $^1$H-NMR (CDCl$_3$) δ 9.58 (s, 1H), 7.50 (s, 1H), 7.35 (dd, 1H, J=8.19, 1.84 Hz), 7.19 (d, 1H, J=1.7 Hz), 6.96 (d, 1H, J=8.18 Hz), 2.58 (t, 2H, J=7.61 Hz), 1.80 (s, 6H), 1.61-1.54 (m, 2H), 1.35-1.25 (m, 2H), 0.88 (t, 3H, J=7.29 Hz); MS (ES) m/z 355 ([M−H]$^-$).

EXAMPLE 65

6-(3-Bromophenyl)-4,4-dimethyl-1,4-dihydro-2H-3,1-benzoxazine-2-thione 6-(3-Bromo-phenyl)-4,4-dimethyl-1,4-dihydro-benzo[d][1,3]oxazin-2-one was prepared from (1,4-dihydro-4,4-dimethyl-2-oxo-2H-3,1-benzoxin-6-yl)boronic acid and 1,3-dibromobenzene according to procedure B. A white solid: mp 174-175° C.; $^1$H-NMR (DMSO-d$_6$) δ 10.35 (s, 1H), 7.88 (bs, 1H), 7.68 (d, 1H, J=7.5 Hz), 7.6-7.51 (m, 3H), 7.4 (t, 1H, J=7.5 Hz), 6.97 (d, 1H, J=8.57 Hz), 1.64 (s, 6H); MS (EI) m/z 331 ([M$^+$], 60%), 333 ([M$^+$], 60%); Anal. Calcd. For C$_{16}$H$_{14}$BrNO$_2$: C, 57.85, H, 4.25, N, 4.22. Found: C, 57.7, H, 4.36, N, 4.09.

A mixture of 6-(3-bromo-phenyl)-4,4-dimethyl-1,4-dihydro-benzo[d][1,3]oxazin-2-one (3 g, 9.04 mmol) and Lawesson's Reagent (1.83 g, 4.51 mmol) in toluene (30 mL) was heated to 110° C. for 24 hours. The reaction was cooled, the toluene removed in vacuo and the residue purified via flash chromatography (silica gel, 20% ethyl acetate/hexane) to give 6-(3-bromophenyl)-4,4-dimethyl-1,4-dihydro-2H-3,1-benzoxazine-2-thione (1.93 g, 61%) as a yellow solid: mp 191-193° C.; $^1$H-NMR (DMSO-d$_6$) (12.3 (s, 1H), 7.92 (s, 1H), 7.72-7.65 (m, 3H), 7.57-7.54 (m, 1H), 7.45-7.39 (m, 1H), 7.14-7.11 (m, 1H), 1.7 (s, 6H); MS (ES) m/z 347 ([M−H]$^-$, 100%); Anal. Calcd. For $C_{16}H_{14}BrNOS$: C, 55.18; H, 4.05; N, 4.02. Found: C, 55.17; H, 3.93; N, 3.97.

EXAMPLE 66

2-(4,4-Dimethyl-2-thioxo-1,4-dihydro-2H-3,1-benzoxazin-6-yl)thiophene-3-carbonitrile 2-(4,4-Dimethyl-2-oxo-1,4-dihydro-2H-benzo[d][1,3]oxazin-6-yl)-thiophene-3-carbonitrile was prepared according to procedure B from (1,4-dihydro-4,4-dimethyl-2-oxo-2H-3,1-benzoxin-6-yl)boronic acid and 2-bromo-3-thiophenecarbonitrile. An off-white solid: mp 200-202° C.; $^1$H-NMR (DMSO-$d_6$) δ 10.49 (s, 1H), 7.75 (m, 1H), 7.63 (d, 1H, J=2.2 Hz), 7.59 (m, 1H), 7.50 (m, 1H), 7.02 (d, 1H, J=8.1 Hz), 1.63 (s, 6H); MS (-ESI) m/z 283 (M−H)$^-$.

The title compound was prepared according to the procedure for Example 16 starting with 2-(4,4-Dimethyl-2-oxo-1,4-dihydro-2H-benzo[d][1,3]oxazin-6-yl)-thiophene-3-carbonitrile. A yellow solid: mp 194-195° C.; $^1$H-NMR (CDCl$_3$) δ 9.56 (s, 1H), 7.67-7.62 (m, 2H), 7.35 (d, 1H, J=5.39 Hz), 7.30 (d, 1H, J=5.33 Hz), 6.98 (d, 1H, J=8.18 Hz), 1.80 (s, 6H); MS (ES) m/z 299 ([M−H]$^-$).

All publications cited in this specification are incorporated herein by referred herein. While the invention has been described with reference to a particularly preferred embodiment, it will be appreciated that modifications can be made without departing from the spirit of the invention. Such modifications are intended to fall within the scope of the appended claims.

What is claimed:

1. A method for providing hormone replacement therapy comprising delivering to a female a composition comprising a compound of formula I and an estrogen receptor agonist or progesterone receptor antagonist to said female, wherein formula I is:

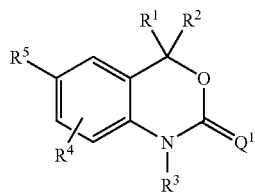

wherein:
$R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, COR$^A$, and NR$^B$COR$^A$;

$R^A$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, amino, $C_1$ to $C_3$ aminoalkyl, and substituted $C_1$ to $C_3$ aminoalkyl;

$R^B$ is H, $C_1$ to $C_3$ alkyl, or substituted $C_1$ to $C_3$ alkyl;

$R^3$ is H, OH, NH$_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, substituted alkynyl, or COR$^C$;

$R^C$ is selected from the group consisting of H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;

$R^4$ is selected from the group consisting of H, halogen, CN, NO$_2$, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, and substituted $C_1$ to $C_6$ aminoalkyl;

$R^5$ is a five or six membered heterocyclic ring having in its backbone 1, 2, or 3 heteroatoms selected from the group consisting of O, S, S(O), S(O$_2$), and NR$^6$ and containing one or two independent substituents selected from the group consisting of H, halogen, CN, NO$_2$, $C_1$ to $C_3$ alkyl, $C_1$ to $C_3$ alkoxy, $C_1$ to $C_3$ aminoalkyl, $C_1$ to $C_3$ perfluoroalkyl, 5 membered heterocyclic ring having in its backbone 1 to 3 heteroatoms, $C_1$ to $C_3$ thioalkoxy, COR$^F$, and NR$^G$COR$^F$;

$R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^G$ is H, $C_1$ to $C_3$ alkyl, or substituted $C_1$ to $C_3$ alkyl;

$R^6$ is H or $C_1$ to $C_3$ alkyl;

$Q^1$ is S, NR$^7$, or CR$^8$R$^9$;

$R^7$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, SO$_2$CF$_3$, OR$^{11}$ and NR$^{11}$R$^{12}$;

$R^8$ and $R^9$ are independent substituents selected from the group consisting of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, NO$_2$, CN, and CO$_2$R$^{10}$;

$R^{10}$ is $C_1$ to $C_3$ alkyl;

or CR$^8$R$^9$ comprise a six membered ring as shown by the structure below:

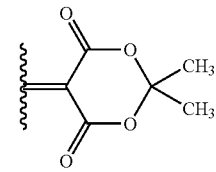

$R^{11}$ and $R^{12}$ are independently selected from the group consisting of H, $C_1$ to $C_6$ alkyl, substituted $C_1$ to $C_6$ alkyl, aryl, substituted aryl, heteroaryl, substituted heteroaryl, acyl, and sulfonyl;

or a tautomer or a pharmaceutically acceptable salt thereof.

2. The method according to claim 1, wherein:
$R^4$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^5$ is substituted by one or two substituents selected from the group consisting of H, halogen, CN, NO$_2$, $C_1$ to $C_3$ alkyl, and $C_1$ to $C_3$ alkoxy;

$Q^1$ is S.

3. The method according to claim 1, wherein:
$R^1$ and $R^2$ are $C_1$ to $C_3$ alkyl;
$R^3$ is H;

$R^4$ is H, halogen, $NO_2$, $C_1$ to $C_3$ alkyl, or substituted $C_1$ to $C_3$ alkyl;

$R^5$ is the five-membered ring b) of the structure:

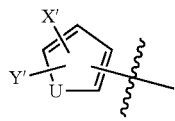

X' is selected from the group consisting of halogen, CN, $C_1$ to $C_3$ alkoxy, $C_1$ to $C_3$ alkyl, $NO_2$, $C_1$ to $C_3$ perfluoroalkyl, 5 membered heterocyclic ring containing in its backbone 1 to 3 heteroatoms, and $C_1$ to $C_3$ thioalkoxy;

Y' is selected from the group consisting of H, halogen, CN, $NO_2$, $C_1$ to $C_3$ alkoxy, $C_1$ to $C_3$ alkyl, and $C_1$ to $C_3$ thioalkoxy;

U is O, S, or $NR^6$; and $Q^1$ is S.

4. The method according to claim 1, wherein:

$R^1$ and $R^2$ are $C_1$ to $C_3$ alkyl;

$R^3$ is H;

$R^4$ is H, halogen, $NO_2$, $C_1$ to $C_3$ alkyl, or substituted $C_1$ to $C_3$ alkyl;

$R^5$ is of the structure:

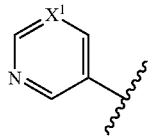

$X^1$ is $CX^2$;

$X^2$ is halogen, CN, or $NO_2$; and $Q^1$ is S.

5. The method according to claim 1, wherein the compound is selected from the group consisting of:

4-(4,4-Dimethyl-2-thioxo-1,4-dihydro-2H-benzo[d][1,3]oxazin-6-yl)-thiophene-2-carbonitrile;

5-(4,4-Dimethyl-2-thioxo-1,4-dihydro-2H-3,1-benzoxazin-6-yl-1-methyl-1H-pyrrole-2-carbonitrile;

5-(4,4-Dimethyl-2-thioxo-1,4-dihydro-2H-3,1-benzoxazin-6-yl)-4-methylthiophene-2-carbonitrile;

5-(4,4-Dimethyl-2-thioxo-1,4-dihydro-2H-3,1-benzoxazin-6-yl)-1H-pyrrole-2-carbonitrile;

tert-Butyl-2-cyano-5-(4,4-dimethyl-2-thioxo-1,4-dihydro-2H-3,1-benzoxazin-6-yl)-1H-pyrrole-1-carboxylate;

[6-(4,4-dimethyl-2-thioxo-1,4-dihydro-2H-3,1-benzoxazin-6-yl)pyridin-2-yl]acetonitrile;

5-(4,4-Dimethyl-2-thioxo-1,4-dihydro-2H-benzo[d][1,3]oxazin-6-yl)thiophene-3-carbonitrile;

5-(4,4-dimethyl-2-thioxo-1,4-dihydro-2H-3,1-benzoxazin-6-yl)-1-ethyl-1H-pyrrole-2-carbonitrile;

5-(4,4-Dimethyl-2-thioxo-1,4-dihydro-2H-3,1-benzoxazin-6-yl)-2-fluorobenzonitrile;

6-(5-Bromopyridin-3-yl)-4,4-dimethyl-1,4-dihydro-2H-3,1-benzoxazine-2-thione;

5-(4,4-Dimethyl-2-thioxo-1,4-dihydro-2H-3,1-benzoxazin-6-yl)-2-furonitrile;

5-(4,4-Dimethyl-2-thioxo-1,4-dihydro-2H-3,1-benzoxazin-6-yl)thiophene-2-carbonitrile;

5-(4,4-Dimethyl-2-thioxo-1,4-dihydro-2H-3,1-benzoxazin-6-yl)-4-propylthiophene-2-carbonitrile;

4-(4,4-Dimethyl-2-thioxo-1,4-dihydro-2H-3,1-benzoxazin-6-yl)-2-furonitrile 2-(4,4-Dimethyl-2-thioxo-1,4-dihydro-2H-3,1-benzoxazin-6-yl)thiophene-3-carbonitrile; and a pharmaceutically acceptable salt thereof.

6. The method according to claim 1, wherein $R^1$ and $R^2$ are $C_1$ to $C_6$ alkyl.

7. The method according to claim 1, wherein:

$R^5$ is containing one or two substituents selected from the group consisting of H, halogen, CN, $NO_2$, $C_1$ to $C_3$ alkyl, and $C_1$ to $C_3$ alkoxy; and $Q^1$ is S.

8. The method according to claim 1, wherein $R^1$ and $R^2$ are $CH_3$.

9. The method according to claim 1, wherein:

$R^1$ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$;

$R^2$ is H, $C_1$ to $C_6$ alkyl, substituted $C_1$ to $C_6$ alkyl, $C_2$ to $C_6$ alkenyl, substituted $C_2$ to $C_6$ alkenyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$;

$R^4$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^5$ is substituted by containing one or two substituents selected from the group consisting of H, halogen, CN, $NO_2$, $C_1$ to $C_3$ alkyl, and $C_1$ to $C_3$ alkoxy;

$R^7$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, and $SO_2CF_3$.

* * * * *

UNITED STATES PATENT AND TRADEMARK OFFICE
CERTIFICATE OF CORRECTION

PATENT NO. : 7,569,564 B2
APPLICATION NO. : 11/351002
DATED : August 4, 2009
INVENTOR(S) : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 593 days.

Signed and Sealed this

Seventh Day of September, 2010

David J. Kappos
*Director of the United States Patent and Trademark Office*